(12) United States Patent
Gonzalvo

(10) Patent No.: US 8,121,861 B2
(45) Date of Patent: Feb. 21, 2012

(54) SERVICE FOR MANAGING MEDICATIONS

(76) Inventor: Sol A. Gonzalvo, Salinas, CA (US)

( * ) Notice: Subject to any disclaimer, the term of this patent is extended or adjusted under 35 U.S.C. 154(b) by 96 days.

(21) Appl. No.: 12/589,691

(22) Filed: Oct. 26, 2009

(65) Prior Publication Data

US 2010/0088120 A1    Apr. 8, 2010

Related U.S. Application Data

(63) Continuation-in-part of application No. 12/283,007, filed on Sep. 8, 2008.

(60) Provisional application No. 60/919,695, filed on Mar. 23, 2007, provisional application No. 61/069,077, filed on Mar. 11, 2008.

(51) Int. Cl.
*G06Q 10/00* (2006.01)
*G06Q 50/00* (2006.01)
(52) U.S. Cl. ................................ 705/2; 705/3
(58) Field of Classification Search .................. 705/2–3
See application file for complete search history.

(56) References Cited

U.S. PATENT DOCUMENTS

| | | | | |
|---|---|---|---|---|
| 5,845,255 | A | * | 12/1998 | Mayaud ............................ 705/3 |
| 6,039,688 | A | * | 3/2000 | Douglas et al. ................ 600/300 |
| 2003/0158754 | A1 | * | 8/2003 | Elkind ............................. 705/3 |
| 2004/0039604 | A1 | * | 2/2004 | Tallal, Jr. ......................... 705/2 |

* cited by examiner

*Primary Examiner* — Sheetal R Rangrej

(57) ABSTRACT

A health management system includes a computerized management site having one or more servers executing software from coupled computer-readable media, and a data repository storing information regarding a plurality of enrolled persons, including at least medications and medication schedules for individual ones of the persons, and storing information regarding a plurality of associate or partner entities comprising at least physicians. In this system persons, in enrollment, enter personal data and medication data, the service stores the data in the repository associated with each enrolling person entering the data, associates the person with one or more physicians and other partner entities whom also enter data in enrollment, and enables enrolled persons to share their individual medication data with associated physicians and other partner entities.

20 Claims, 32 Drawing Sheets

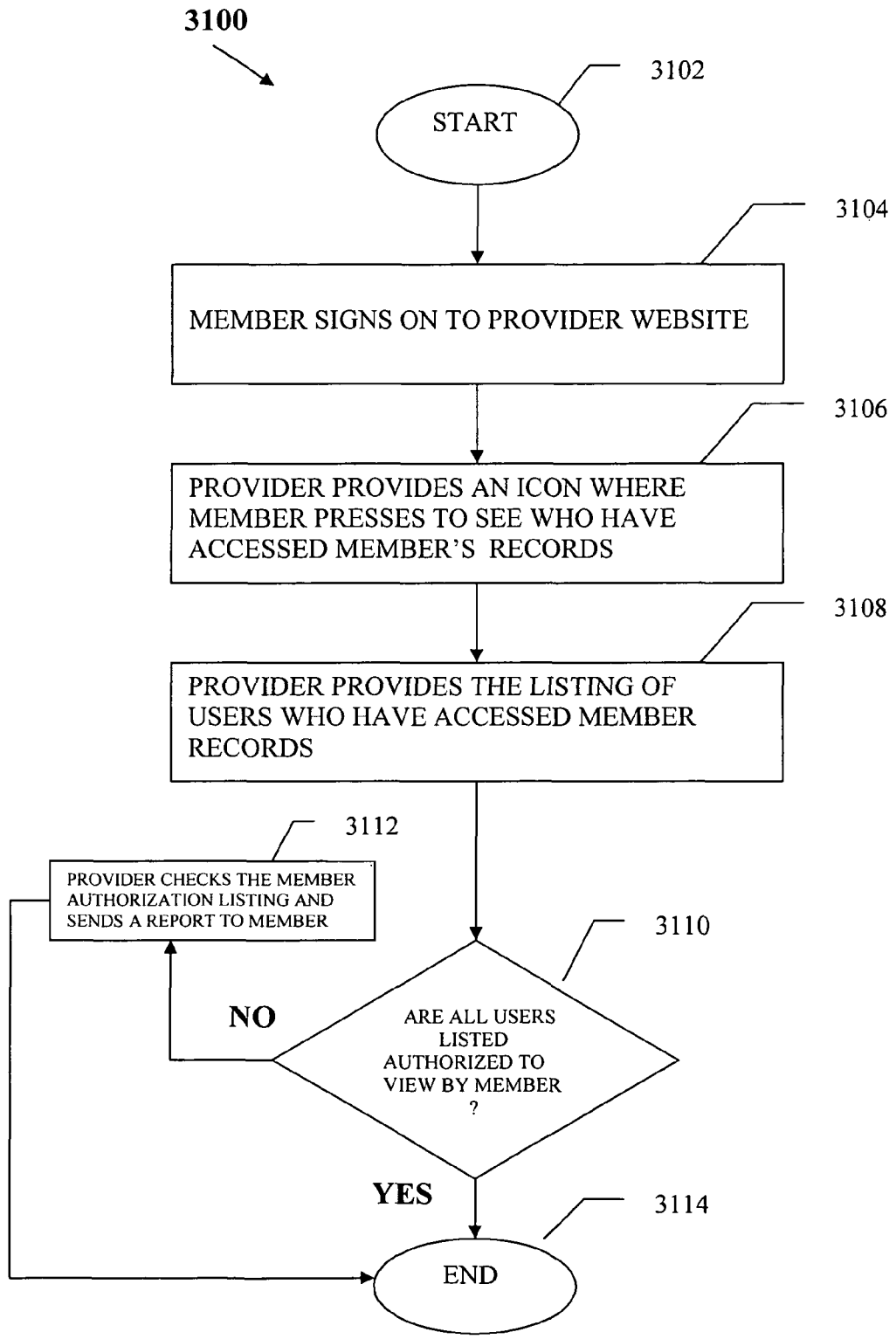

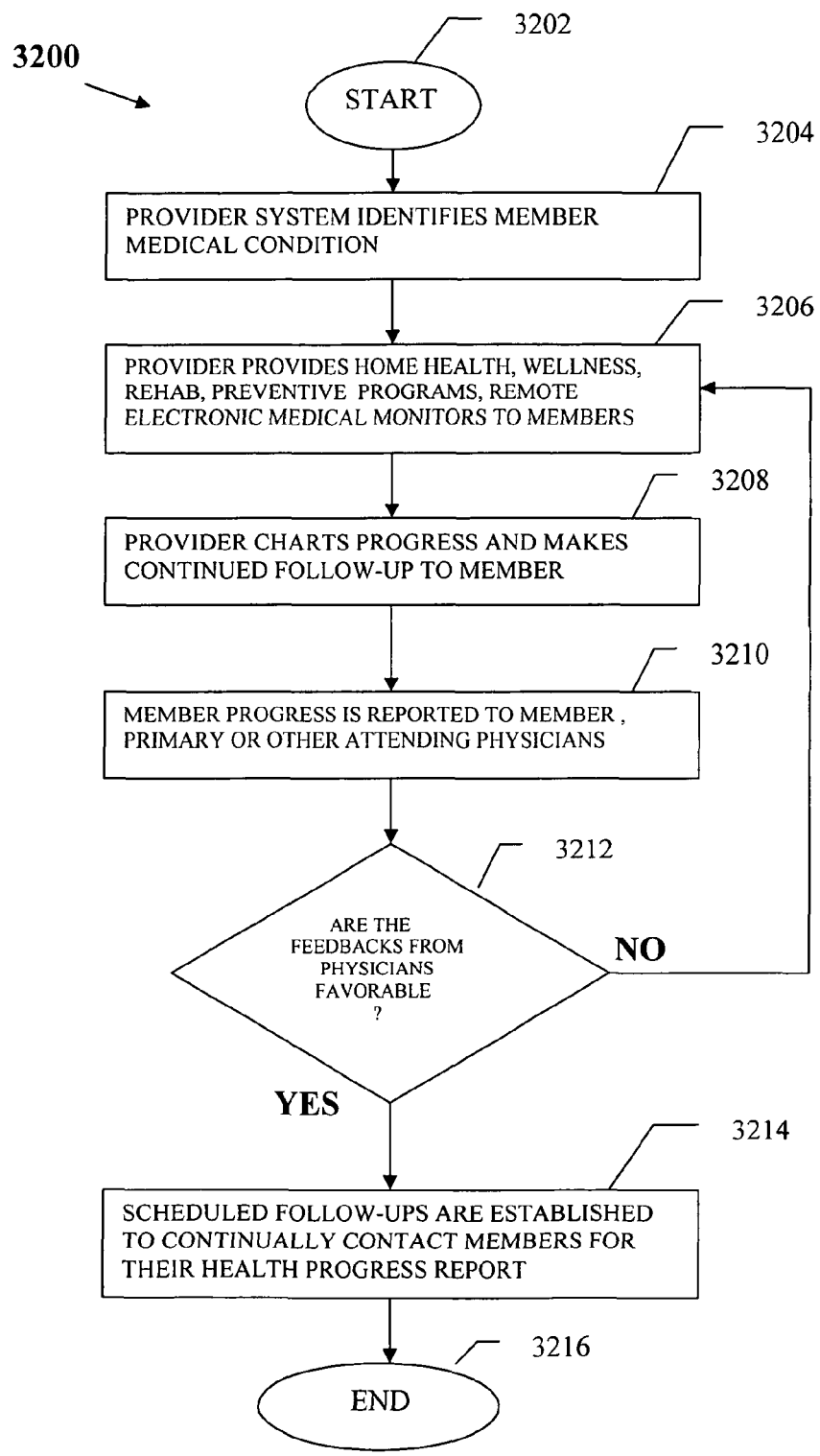

SERVICE FOR MANAGING MEDICATIONS

CROSS-REFERENCE TO RELATED APPLICATIONS

This application is a continuation-in-part of U.S. Non Provisional application entitled "Service for Managing Medications", Ser. No. 12/283,007 filed on Sep. 8, 2008, which claims the benefit of provisional application 60/919,695 filed on Mar. 23, 2007, and claims the benefit of provisional application 61/069,077 filed on Mar. 11, 2008 in the name of the present inventor. The entire contents of these prior applications are hereby incorporated by reference in its entirety at least by reference.

BACKGROUND OF THE INVENTION

1. Field of the Invention

This invention is in the broad field of internet-connected services, and other personalized direct services that pertains more particularly to a service for providing with medication management, home health services, wellness and rehabilitation programs to the members.

2. Description of Related Art

It is well-known that millions of persons worldwide take one or more medications regularly, typically prescribed by physicians, for managing medical conditions. Many people, especially older people, take multiple medications daily, and the particular regimen for a person that medicates may change regularly as well, as medical conditions get worse or better, and the prescribing doctors adjust medication levels, and change medications for the same medical conditions for their patients. It often happens as well that new conditions are discovered and diagnosed for patients, and new medications are added to the mix that a patient may regularly ingest.

Because of the wide-spread use of medications, and the frequent changes in dosage and medications for individual patients, keeping track of what medications and dosage is a frequent problem for individuals dependent on multiple medications. It is less well-known that there also may be many chemical reactions among different medications, creating chemical situations in a human body that may have completely unintended consequences. Another problem in this entire mix is related to the fact of increasing specialization in the medical field. It is often the case that one individual may be consulting one specialist for one condition, and another specialist for another condition, and the different specialists seldom have an opportunity to consult with one another.

Based on the above-described situation in general, what is clearly needed in the art is a service for medicated persons where all of the medications for a person may be listed and monitored, and which the person may depend upon for information about medications, combinations, expected side effects and the like, and where doctors prescribing medications for the person may also interact, and where the abnormal test results reported by members are followed up and bring back to its normal ranges through home health, wellness and/or rehabilitation programs.

BRIEF SUMMARY OF THE INVENTION

The present inventor, being very familiar with procedures and processes in the field of medicine, interactions between persons needing medication, and physicians and hospitals providing medicinal services, has long been aware of many problems in that field. As a result the inventor has developed a service that can solve many of the problems.

In one embodiment of the present invention a health management service is provided, comprising a computerized management site having one or more servers executing software from coupled computer-readable media, and a data repository storing information regarding a plurality of enrolled persons, including at least medications and medication schedules for individual ones of the persons, and storing information regarding a plurality of associate or partner entities comprising at least physicians. Persons, in enrollment, enter personal data and medication data, the service stores the data in the repository associated with each enrolling person entering the data, associates the person with one or more physicians and other partner entities, whom also enter data in enrollment, and enables enrolled persons to share their individual medication data with associated physicians and other partner entities.

In various embodiments a variety of services are provided, such as:

physicians associated with enrolled persons are enabled to edit and alter medications and medication schedules for individual enrolled persons with whom they are associated in the service, and alterations will be published by the service, subject to authorization by the enrolled person, with other physicians and associate and partner entities each also associated with the enrolled person.

persons are enabled to enter allergies in general and allergies to medications, as well as medication data, other medication data that should not be prescribed.

in any transaction changing medication data for an enrolled person, allergy data is consulted, and participants are alerted to any potential problem.

the data repository stores information regarding potential interactions between medications and between medications and common foods and beverages, and, in any transaction changing medication data for an enrolled person, the potential interaction data is consulted, and participants are alerted to any potential problem, stores pictures of both the trade and generic medications and the official medication description, provides listing of medications that should be avoided based on enrolled person's medication condition.

new persons enrolling in the service, after entering their medication data, are informed of potential interactions between medications and potential effects of such interactions.

enrolled persons are enabled to publish their medication data to third-parties, whether partner/associates of the service, or not.

a mechanism is provided, including interactive interface, for a enrolled persons to purchase medications, products and services from enrolled partner firms.

enrolled persons are afforded discounts for purchases from enrolled partner firms.

the service provides email service to enrolled persons and partners and associates.

enrollment provides membership requiring a periodic membership fee, and discounts on the membership fee are afforded to enrolled persons as reward for exceeding pre-set thresholds in purchasing medications, products and services from enrolled partner firms.

the service seeks sources for medications, products and services from other than enrolled partners and associates.

the service seeks sources for generic versions of medications.

information regarding best times and circumstances for taking medications is stored, and provided to enrolled persons according to the enrolled person's medication data.

the service provides accounting and billing services for enrolled persons in the purchase of medications, products and services. And the service provides interactions with members through the use of internet, telephone, personal visits and electronic medical monitoring.

BRIEF DESCRIPTION OF THE SEVERAL VIEWS OF THE DRAWINGS

FIG. 31 is the flow diagram that depicts a feature of providing an icon where the member can click for the listing of users of have accessed and/or viewed their medical records.

FIG. 32 is the flow diagram that illustrates the process of providing members various ways for which continued rehabilitation, prevention and wellness programs are provided to members.

DETAILED DESCRIPTION OF THE INVENTION

Figure 1:
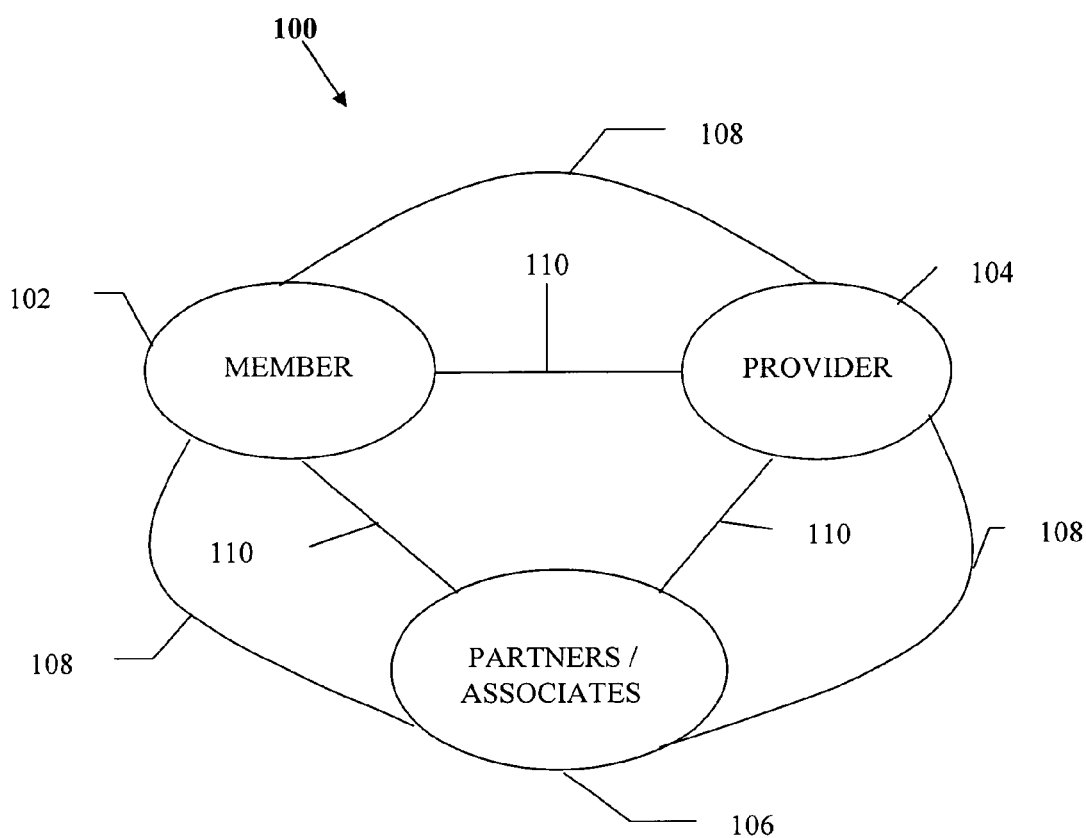
FIG. 1 is a diagram of elements of a service in an embodiment of the present invention.

FIG. 1 is a diagram of elements of a service 100 in an embodiment of the present invention. The service depicted is a and method for providing members of the service an ability to enter information and print information from home of medications being taken, and to receive purchase discounts for medication purchases according to various embodiments described herein. As used herein, the term "enter and print" shall refer to entering of several categories of information for a member, such as medications that have been prescribed or may be prescribed by a licensed medical practitioner, over the counter medications, herbal supplements, member allergies, medical history, and some other personal information. The personal information may include but not be limited to addresses, telephone numbers of families, friends, business acquaintances or the like; into a provider's website 104, and printing the same off of provider's website.

As used herein, the term "purchase discounts" shall refer to any commercial goods or professional health care services that members may purchase from any partner/associate 106. As used herein, the term "medical history" refers to historical medical information about a member that may include but is not limited to diagnoses, procedures, medications taken, doctor visits, hospital visits, surgeries done, x-ray pictures taken and allergies, to name a few. Examples of such commercial goods include over the-counter medications, health care supplies, health care equipment, prescription drugs or the like. An example of professional health care services include any health care practitioner services that may include physical therapies, respiratory therapies, laboratories, x-ray, MRI, CT Scan or the like, and the invention is not limited to any particular type of commercial goods nor health care practitioner's type.

According to one embodiment, a member 102 my enter over link 108 a listing of medications being taken from home, which may be simply termed "home meds", and allergies which may be from food or medications or the like, which are stored associated with that member in a provider's member's database over link 108. Member 102 may be defined as a person without any affiliation to any particular group that may include, but is not limited to an insurance company or the like, whether a non-profit or for-profit, or a person who is affiliated with or a member of a group represented by an insurance company or the like, that could be classified as a non profit or a for-profit operation.

Link 108 may be of any medium for transferring data between member 102, providers 104 and/or partner/associates 106, and the invention is not limited to any particular medium. Examples of link 108 include, without limitation, a network such as a local area network (LAN), a wide-area network (WAN) or the Internet, a telecommunications link, a wire or optical link or a wireless connection. Partner/associates 106 may be centralized or distributed depending upon the requirements of a particular application, and may include but are not limited to, hospitals, doctors offices, licensed physicians, pharmacy stores, licensed therapeutic clinics, outpatient clinics, wholly owned subsidiaries, discount stores that sell prescribed or over the counter medications, insurance companies and employer's private or public to name a few.

In a situation where a member 102 gets admitted into a partner 106, being for example, a hospital, the hospital may be asking the member 102 the home meds listing needed for medication reconciliation, the purpose of which is for medication safety. For example, a treating physician is required to compare member 102 existing medications with medications that may be ordered during admission, transfer or discharge of member 102.

One of the ways in which member 102 may provide home meds listing to the partner/associate 106 would be via delivery channel 110. Delivery channel 110 may be implemented by any mechanism or medium that provides for the transfer of a copy of home meds listing from provider 104 database to partners/associates 106 and the invention is not limited to any particular type of delivery channel. Examples of delivery channel 110 include, without limitation, hand delivery by member 102, mail delivery, courier delivery, delivery using a delivery agent, or printing a copy over the internet to partner/associate 106 Internet printer.

Provider 104 in one embodiment is a single provider of the services alluded to in embodiments of the present invention, while member 102 and Partner/Associates 106 may be a varied plurality. That is, there may be many members of the service, that is clients of or subscribers to the service, and there may likewise be a broad variety of partners and associates according to the description above.

Figure 2:
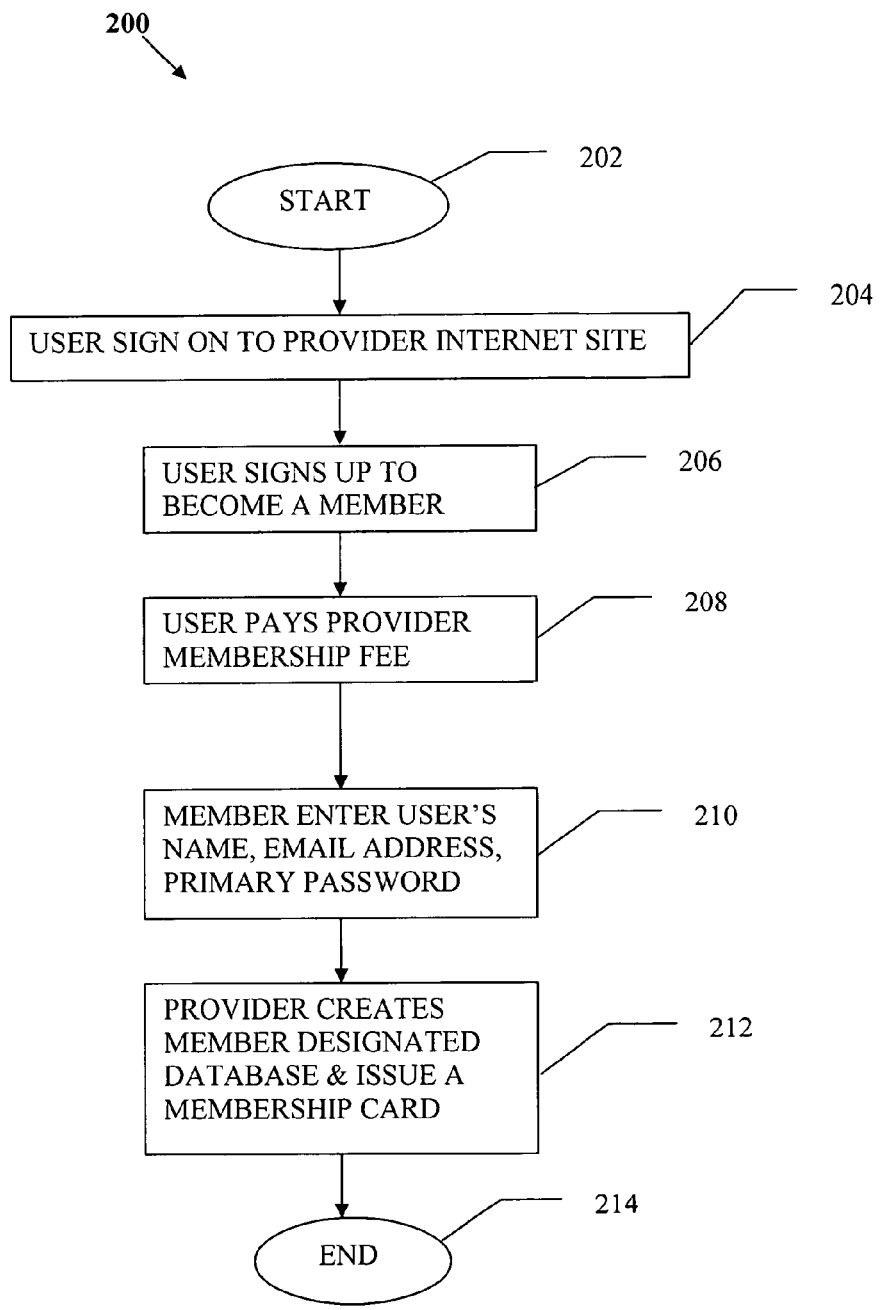
FIG. 2 is a flow diagram depicting member sign-up for the service of FIG. 1.

FIG. 2 is a flow diagram 200 illustrating how an individual member signs up for the service in one embodiment of the invention. Starting from step 202, in step 204, member 102 logs on to provider 104 web site. In step 206, member 102 signs up to become a member by agreeing to the terms and conditions set forth by provider 104. As used herein, the term "terms and conditions" refer to member 102 to pay a membership fee and provider 104 to provide the necessary secured database, delivery, purchase discounts from partners/associates 106, and secure the member 102 information entered into provider 104 web-based computer. In step 208, member 102 pays provider 104 a membership fee which could be a monthly, semi-annual or annual fee. As described previously, the purchase discount received by member 102 by purchasing commercial goods or professional services from partners/associates 106 may on an annual basis. In some situations, member 102 membership fee could be refunded if certain conditions are met. Member 102 may even receive purchase discounts whose total value may even exceed the annual membership fee resulting in a free membership. In particular, purchase discounts have no limitation as far as the purchase discount amount is concerned, and only are limited my member 102 purchases from partners/associates 106. In step 210, member 102 enters user's name, date of birth, email address and primary password, then in step 212, provider 104 sets up a secured database data record, that may include but is not limited to fields like name of member, date of birth, email address, name of medication, dose, route, frequency, date prescribed, name of doctor, date medication was started, date medication was stopped, reason for the medication, pictures of x-ray taken, or the like. At step 212 the service prepares and issues a membership card to the new member. The card may be called a "Medicard". When either member 102 or any partner/associate wants to print member 102's "home meds", the listing may be printed with the primary sort of active meds (active medications first, followed by stopped medications) then followed by the date when medication was prescribed, at least two names and telephone numbers of member 102 next of kin or authorized representatives, which could then be contacted in case of an emergency, and then the process is complete in step 214.

"Medicard" can be described as a printed membership card, being of a wallet size, having the provider 104 name and logo, the address, telephone number, the member 102 membership ID number, member address, telephone number and next of kin name and telephone number that may be printed at a front page, and the allergies and "home meds" may be printed at a back page of said "Medicard".

Figure 3:
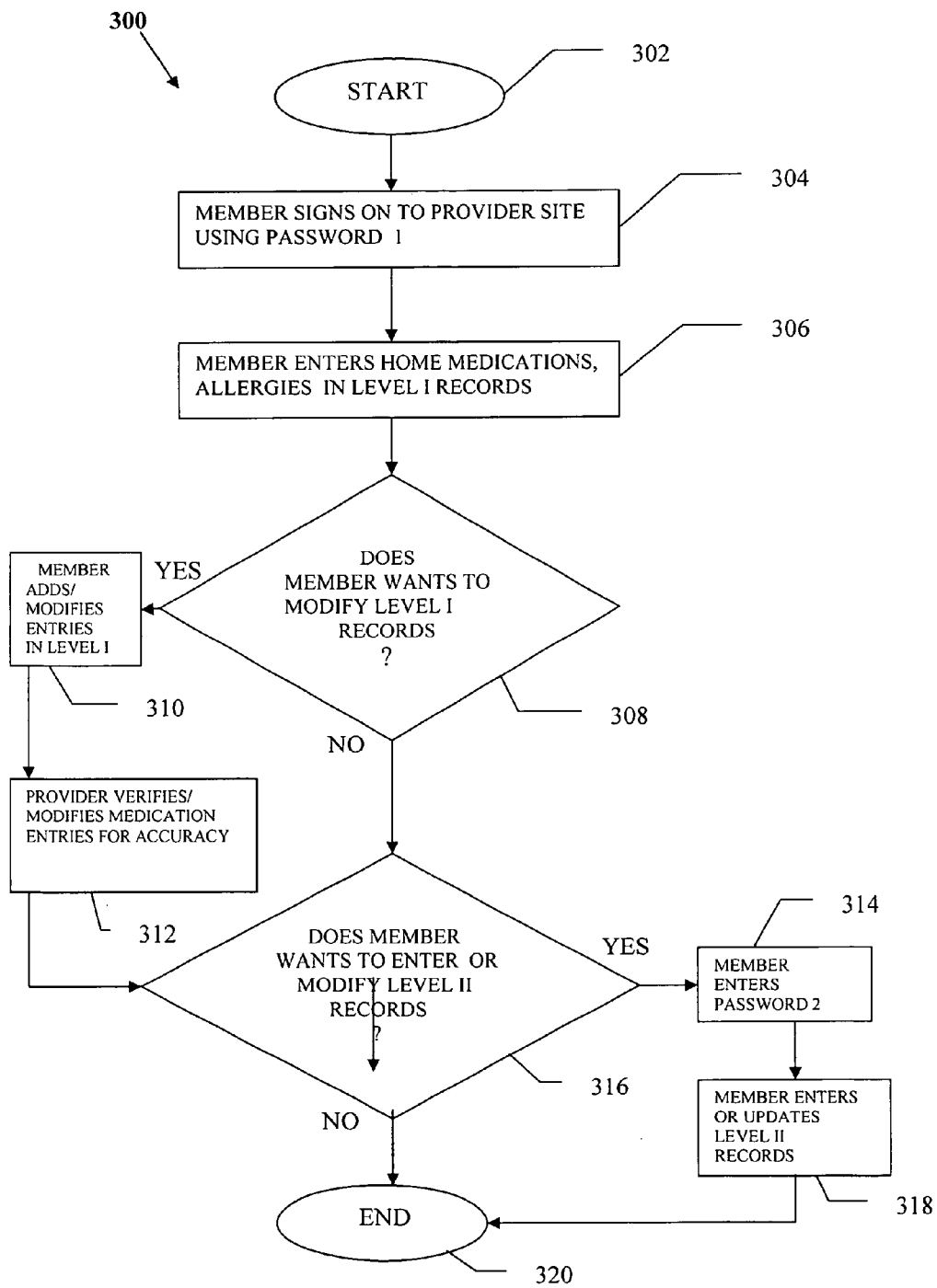
FIG. 3 is a flow diagram illustrating how a member enters or modifies information in embodiments of the invention.

FIG. 3 is a flow diagram 300 depicting a method by which a member a member enters or modifies allergies, "home meds" and other data. Starting from step 302, member 102 signs on to provider 104 web site using password 1 as shown in step 304. Then in step 306, member 102 opens up a Level I Database and enters the medications being taken from home "home meds", allergies which may include but not limited to food allergies, medication allergies, substance allergies or any drug allergy interactions. Level I Database as shown in step 306 may be implemented by provider 104 by building database records that comprise fields that identify a specific member that may include without limitation, the name of the member, last four digits of social security number, date of birth, EMR (electronic medical record) number, telephone number, email address, sex, "home meds" listing, name/names of next of kin and their respective telephone numbers or the like.

As described previously herein, the listing of medications being taken from home or simply called "home meds", in which corresponding database records need to be created by provider 104 in Level I Database may comprise field names that may include without limitation, name of doctor, the date medication was prescribed, name of medication, dose, route, frequency, reason for the medication, name of vendor, quantity, cost of each medication, date the medication was started, date the medication was stopped, and the like. In step 308, a determination is made whether the member 102 wants to modify existing records in Level I Database. If so, member 102 add/modifies entries in Level I Database. In step 310, member 102 enters new medications or modifies existing medication list being taken from home, allergies which may include but not limited to food allergies, medication allergies, substance allergies or any drug allergy interactions, then in step 312, the provider 104 verifies the accuracy of the medication entries entered by member 102, and makes necessary corrections if needed, and in step 316 a determination is made whether member 102 wants to enter or modify other data in Level II Database, in addition to "home meds" listing that may include without limitation, names, addresses, telephone numbers, anniversary dates, birth dates of relatives and friends, recipes or anything that may be of importance to a member 102 or the like. If not, the process is then complete in step 320.

If, however, member 102 decides to add other data to the Level II Database, then member 102 clicks on an icon specifically for Level II Database and enter member 102 password 2 in step 314. In step 318 member 102 enters/updates (Level II Database) and the process is then complete in step 320.

Figure 4:
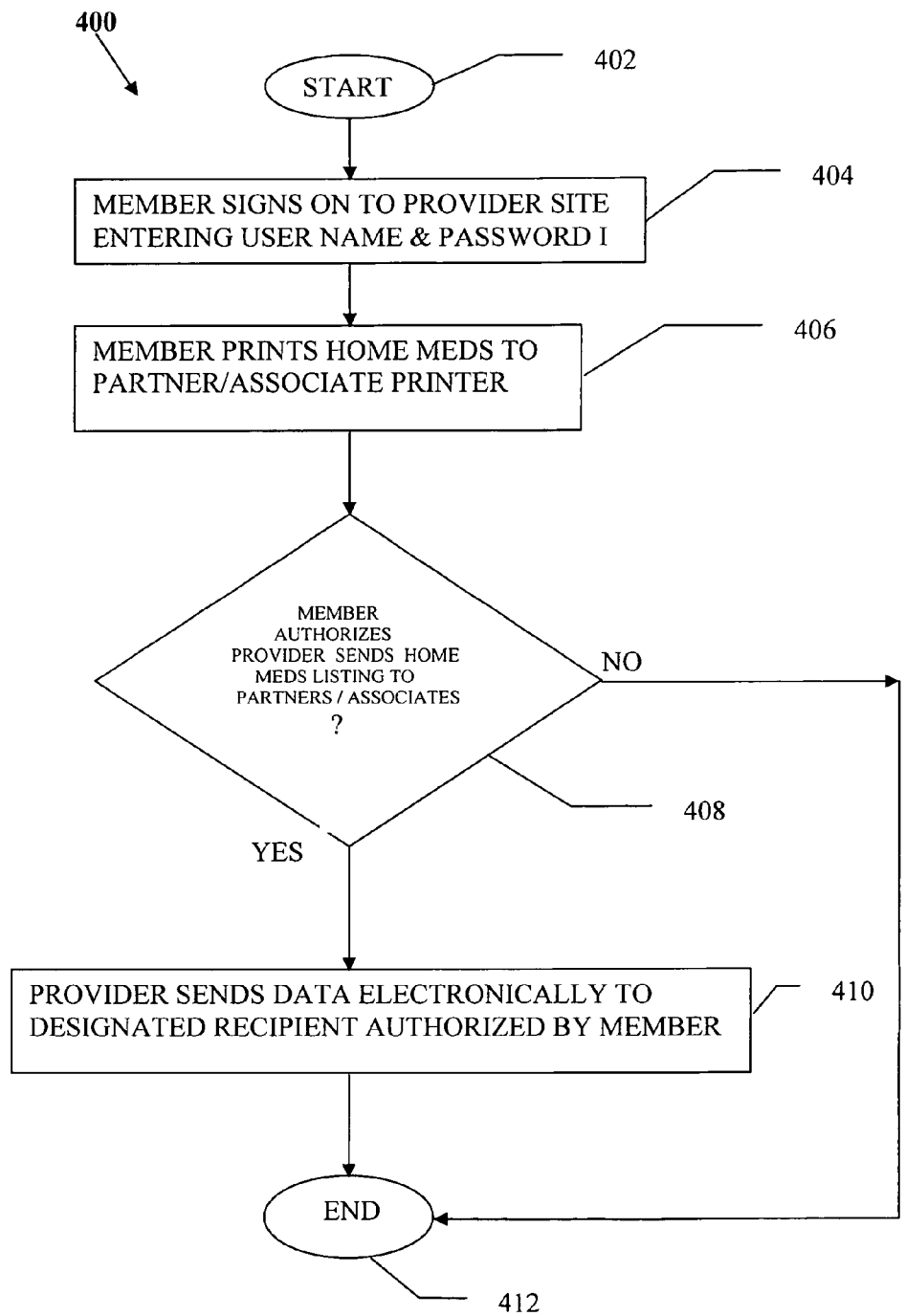
FIG. 4 is a flow diagram illustrating a method for a member may authorize a provider to send medications listings to any partner/associate or others in an embodiment of the invention.

FIG. 4 is a flow diagram 400 showing a process by which a member 102 may authorize provider 104 to send a medication listing to any partner/associate, or whomever member 102 wants a list of allergies and "home meds" delivered to. After starting from step 402, in step 404 member 102 signs on by logging into a web site associated with provider 104, over link 108, which may be secured or unsecured depending upon the requirement of a particular application, by entering a user name and password 1. This process opens up the Level I Database specifically assigned to member 102 by provider 104, and in step 406, member 102 has options without limitation of printing member 102 allergies and "home meds" to his or her home printer, or print allergies and "home meds" to a partner/associate printer, or to any printer that member 102 so desires over link 108. The member may alternatively or also cause a file of the information to be delivered electronically to any connected party.

In step 408, a determination is made whether member 102 authorizes provider 104 to send member 102's allergies and "home meds" to any partner/associate. If not, then the process is complete in step 412. If, however, member 102 authorizes provider 104 to send the data to any partner/associate over link 108 or delivery channel 110, in which case step 410 is implemented, and then the process is complete in step 412.

Figure 5:
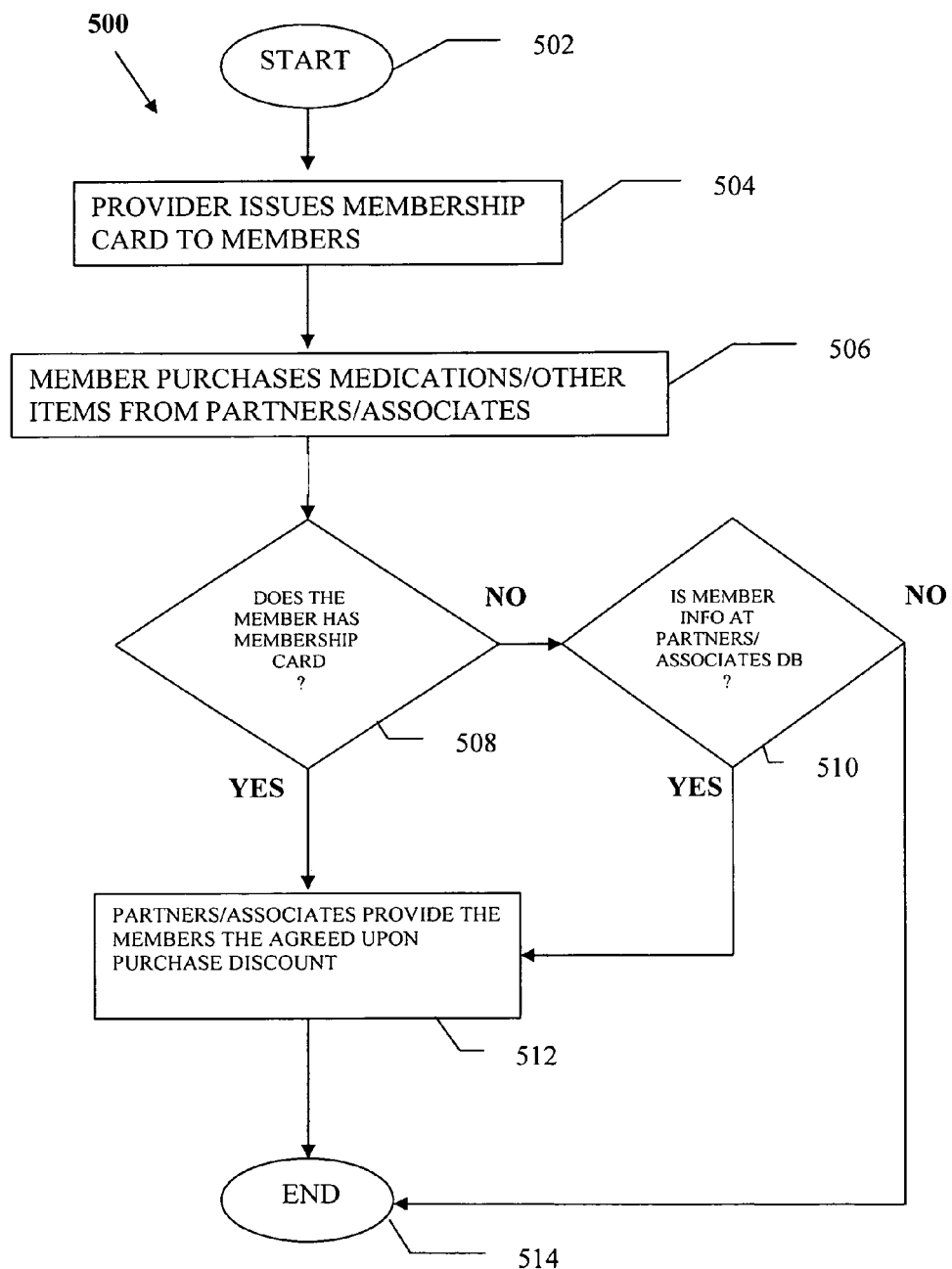
FIG. 5 is a flow diagram that illustrates a method for providing purchase discounts to members in an embodiment of the invention.

FIG. 5 is a flow diagram 500 that illustrates a method for providing purchase discounts to member 102 for medication or other commercial products purchases from any partner/associate 106 as may have been agreed upon between partner/associate 106 and provider 104. After starting in step 502, in step 504, provider 104 issues a membership card to member 102. In step 506, member 102 may purchase the medication or other commercial products and may be entitled to purchase discounts that are based upon the previous agreements between partners/associates 106 and provider 104. Such purchase discount may range from 1 percent to any percentage that was agreed upon between the partners/associates and the provider. As an example, a 10 percent purchase discount will apply to all medication purchases and/or a 5 percent purchase discount to all other commercial products sold by any partner/associate 106. In step 508, a determination is made as whether the membership card is with the member 102 at time of purchase, and if the response is yes, then at step 512 the discount is implemented whereby the partner/associate 106 sells the products or services to member 102, deducting the agreed-upon purchase discount with provider 104, and the process is complete in step 514. However, if in step 508 member 102 does not have the membership card at the time of purchase, but the member 102 information is at partner/associate 106 database records, then step 510 is implemented, followed by step 512 in which the partner/associate sells the products deducting the agreed-upon purchase discount and the process is complete in step 514.

In a situation where customer 102 does not have the membership card at the time of purchase, and if in step 510 the member 102 membership information is not at the partner/associate 106 database base, then the process is complete in step 514 resulting of not being able to accommodate providing purchase discount to customer 102.

Figure 6:
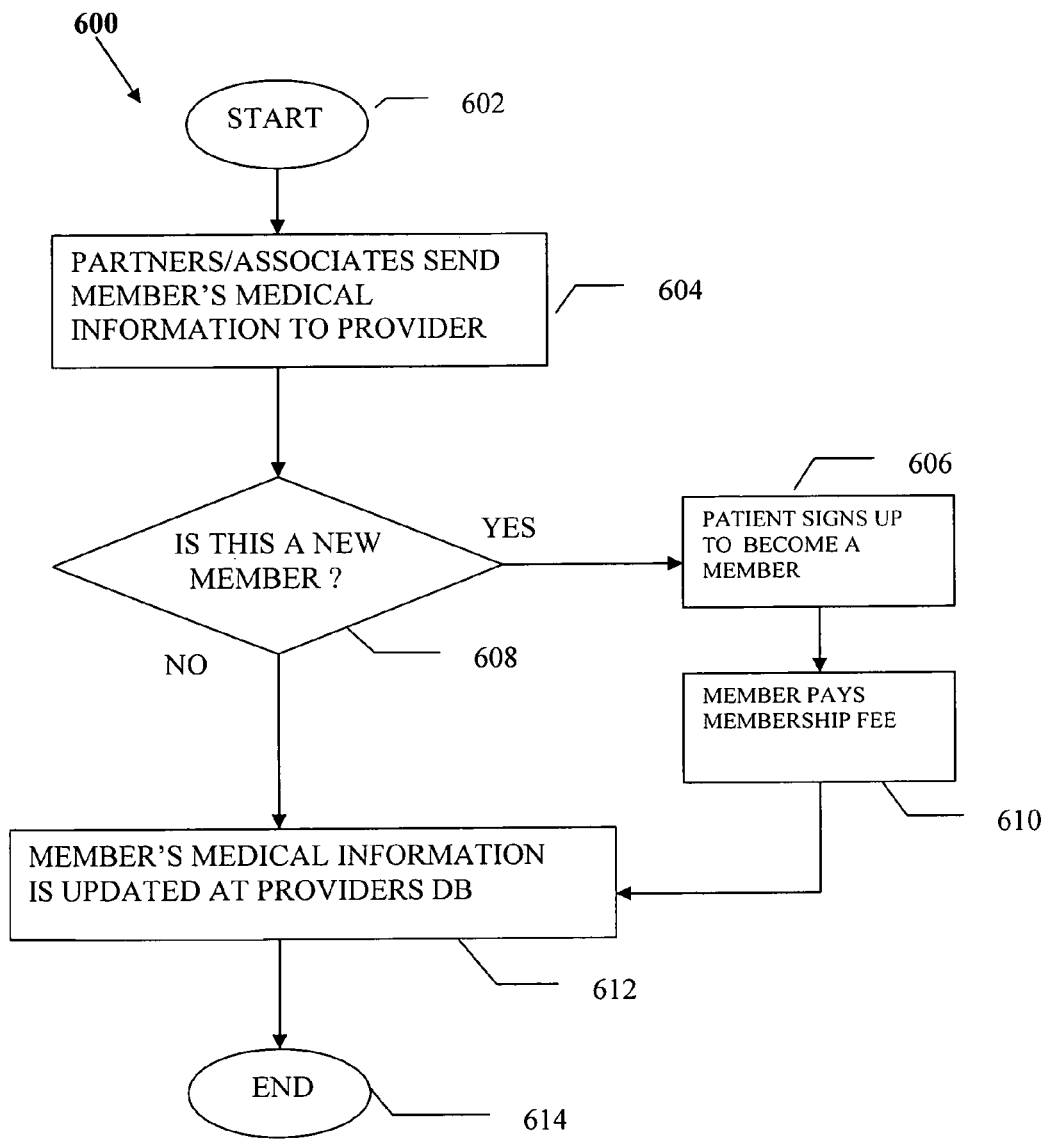
FIG. 6 is a flow diagram that illustrates a method by which partner/associates may send members medical information in an embodiment of the invention.

FIG. 6 is a flow diagram 600 that illustrates a method by which partner/associates 106 send member 102 medical information which may include, but is not limited to new medication prescriptions, new allergies, new drug reaction to certain medications or the like to provider 104 database over link 108 or delivery channel 110. After starting in step 602, at step 604 provider 104 updates the member 102 data records in Level I Database. In step 608 a determination is made as to whether member 102 is a new member, and if not, then provider 104 updates member 102 medical information that may include but is not limited to adding new medications, allergies, drug reactions or the like in step 612, and the process is then complete in step 614. If, however, member 102 is a new member, then step 606 is implemented, signing up the new member, and then in step 610 the new member 102 pays provider 104 the membership fee and the process is then complete in step 614.

Figure 7:
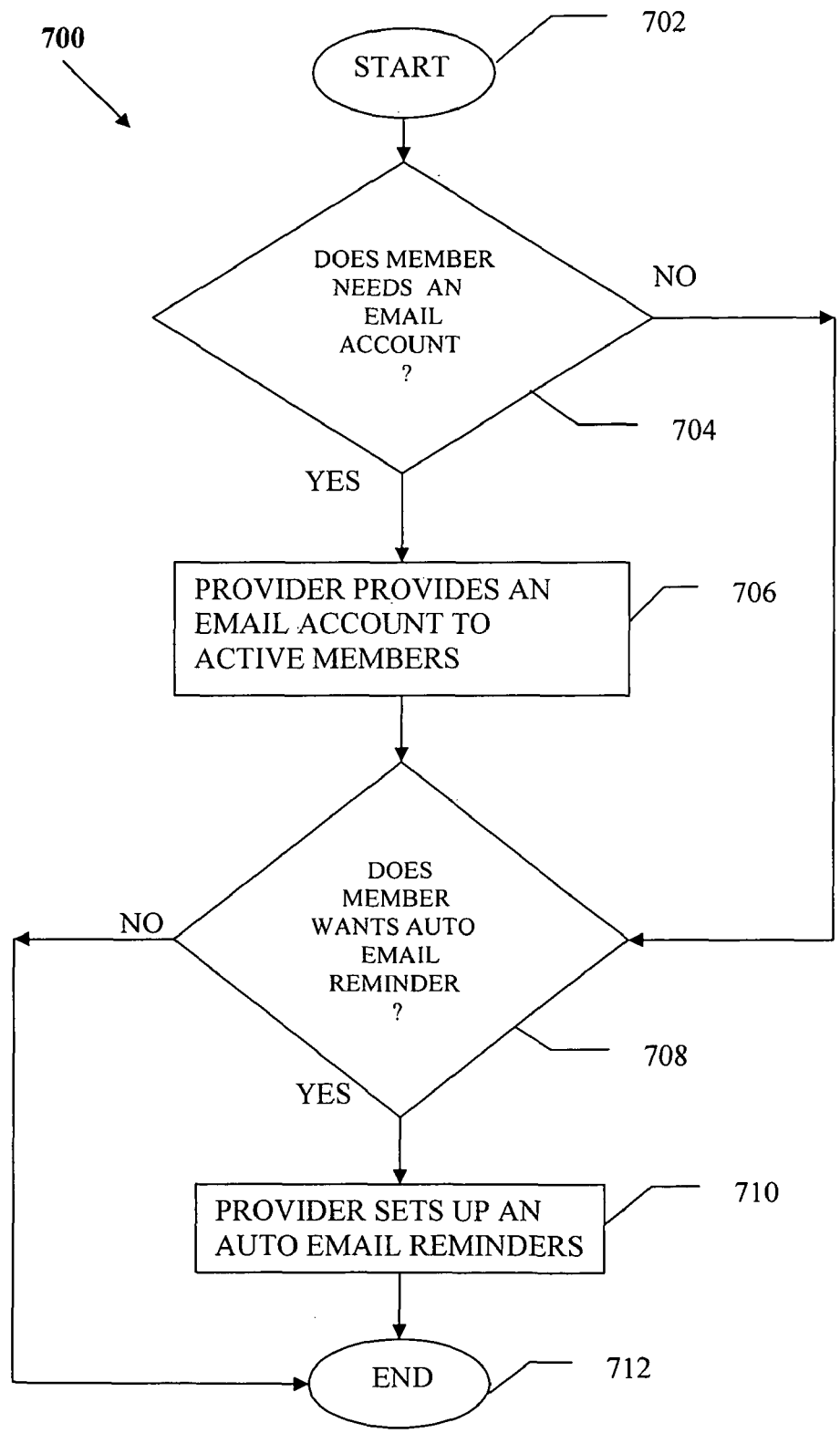
FIG. 7 is a flow diagram that illustrates the use of electronic mail in an embodiment of the invention.

FIG. 7 is a flow diagram 700 that illustrates use of electronic mail that may include without limitation the member 102, provider 104 and/or partners/associates 106. After starting in step 702, in step 704 a determination is made as to whether member 102 needs an electronic mail account, and if needed, then in step 706 provider 104 creates an electronic mail for member 102. Then in step 708 a determination is made as to whether member 102 needs an email reminder, which may include but is not limited to doctor's appointment, hospital visit, therapist visit, an anniversary date, a birth date or the like, and then in step 710 the provider 104 sets up automatic electronic reminders to be sent for those specified dates that have been requested by member 102, and the process is complete in step 712.

If, in a situation where a determination is made that member 102 in step 704 does not need an electronic mail account, then the control moves to step 708, where a determination is made as to whether member 102 needs an electronic mail reminder, which may include but is not limited to doctor's appointment, hospital visit, therapist visit, an anniversary date, a birth date or the like. Then in step 710 provider 104 sets up automatic electronic mail reminders to be sent for those specified dates that have been requested by member 102, and the process is complete in step 712.

If, however, after determining that member 102 does not need an automatic electronic mail reminder in step 708, then the process is complete in step 712.

Figure 8:
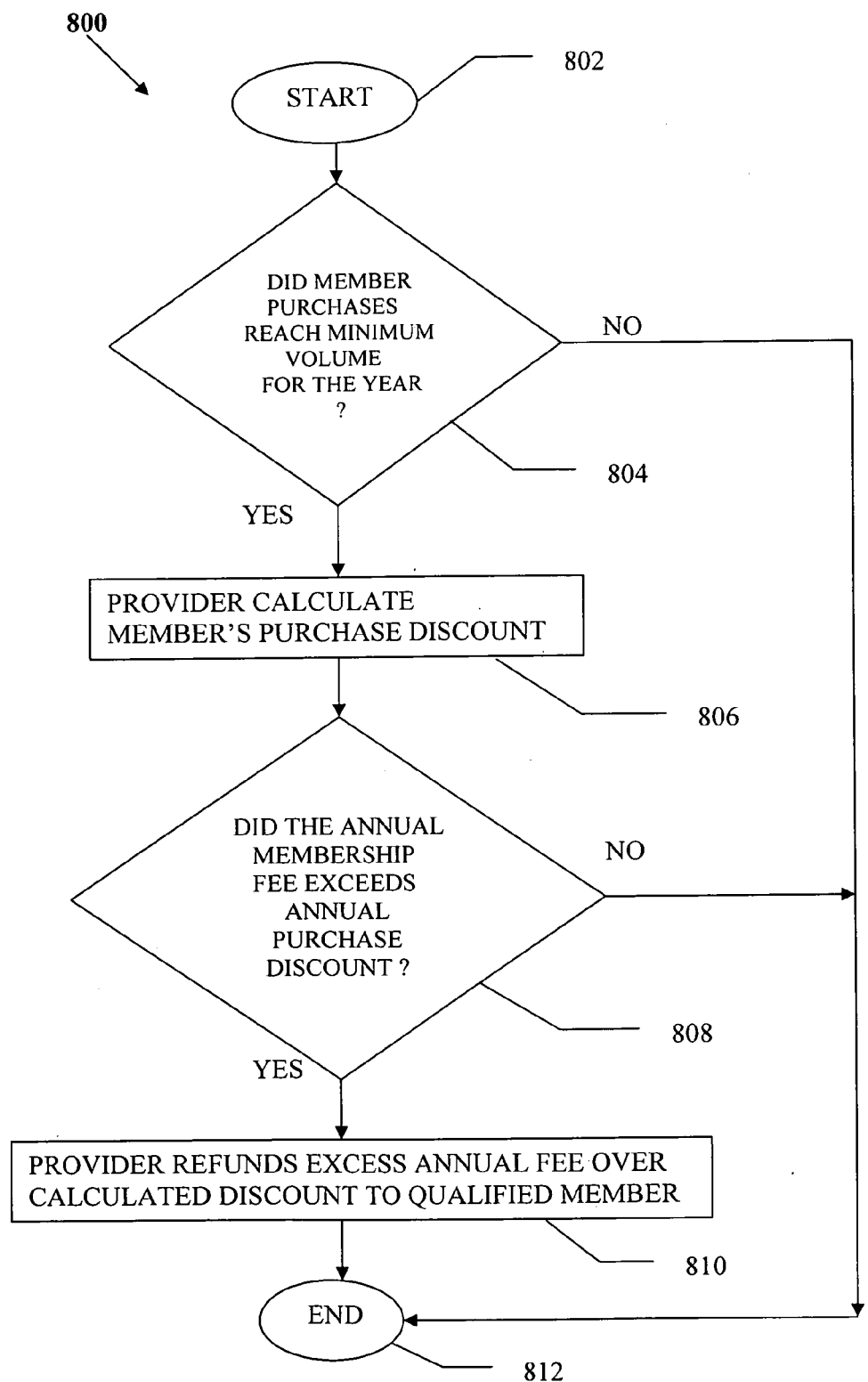
FIG. 8 is a flow diagram depicting free membership for a member if certain minimum purchase requirements are met within a defined period in embodiments of the invention.

FIG. 8 is a flow diagram 800 depicting free membership for a member if certain minimum purchase requirements are met within a defined "membership period". As used herein, the term "membership period" refers, for example, to any twelve month period that begins at the first day of the member 102 signed up and ends at the last of day of the twelve month anniversary of signed up date. Other membership periods may pertain, however.

After starting in step 802, in step 804 a determination is made as to whether the member 102 has reached the minimum purchased amount for a membership period. The minimum purchased amount may include without limitation any amount of money that will be agreed upon by and between member 102 and provider 104. For example, one thousand dollars, five hundred dollars or any set amount that may be agreed upon by and between the member and the provider. If so, then in step 806, provider 104 tabulates all member 102 purchase discounts received from partners/associates 106. Then in step 808 another determination is made as to whether the annual membership fee paid by member 102 to provider 104 exceeds the member 102 total purchase discounts received for the membership period, and if it does, then it triggers step 810 where provider 104 refunds the excess membership over the total purchase discount for the year, and then the process is complete in step 812.

However, if in step 804, after determining that the member 102 did not reach the minimum volume amount for the year, then the process is complete in step 812. If however, if in step 808 after determining that the membership fee did not exceed the total purchase discounts received for the year, then the process is complete in step 812.

Figure 9:
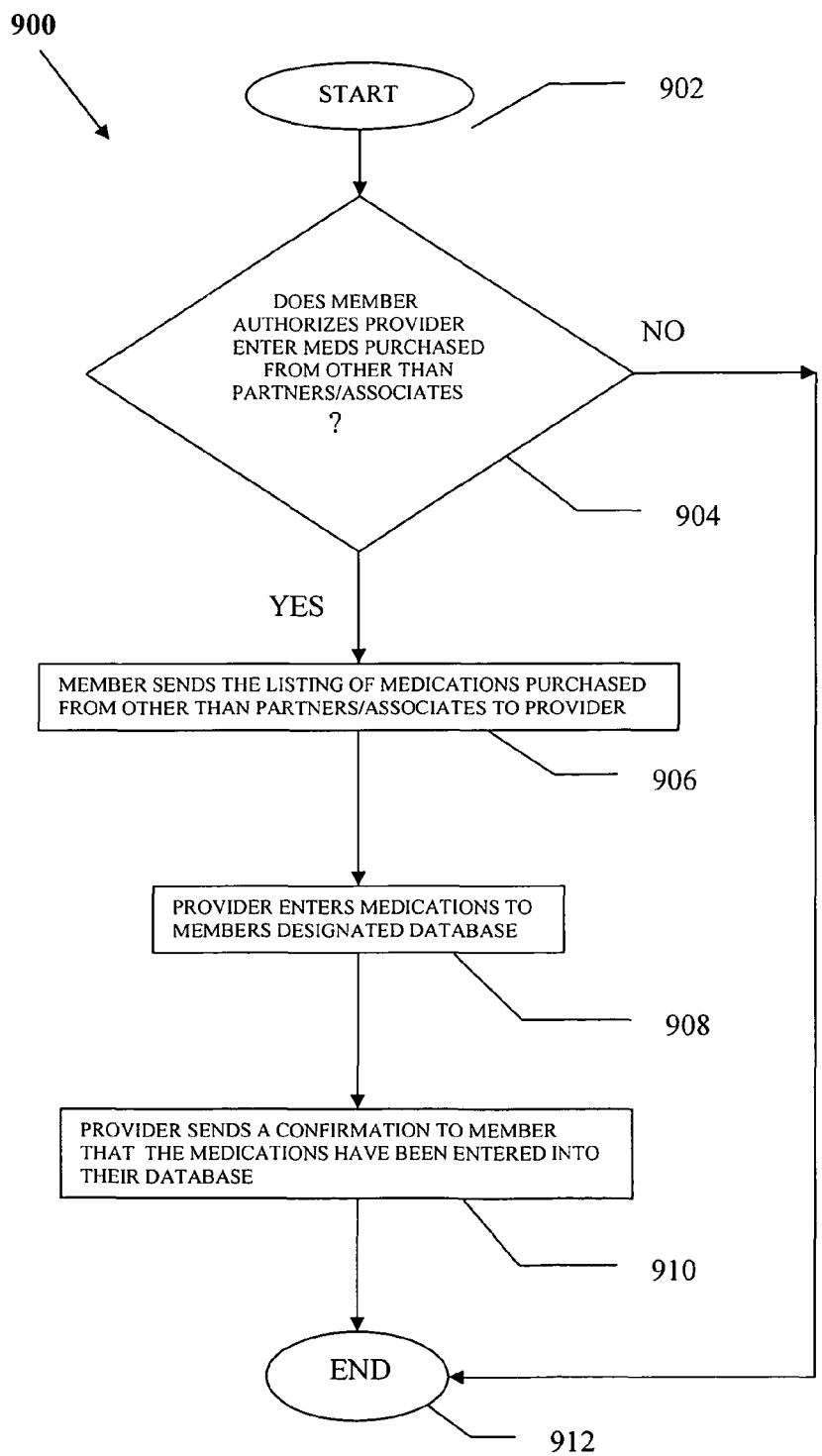
FIG. 9 is a flow diagram that illustrates a process for members to authorize providers to enter medication purchases from other than partners/associates in embodiments of the invention.

FIG. 9 is a flow diagram 900 that illustrates a process of member 102 authorizing provider 104 to enter medication purchases from other than partners/associates 106, which may be defined as "other medications". After starting in step 902, in step 904, a determination is made as to whether member 102 wants provider 104 to enter and add "other medications" to provider 104 database, if so, then in step 906, member 102 sends the listing of "other medications" to provider 104. Then in step 908, the provider 104 enters the "other medications" to member 102 designated database, and in step 910, provider 104 sends a confirmation to member 102 either over the link 108 or the delivery channel 110, and the process is then complete in step 912.

If however, in step 904, after determining that member 102 does not want to send the listing of "other medications" to provider 104, then the process is complete in step 912. For purposes of calculating the member 102 purchase volume for the year as shown in step 804, the value of "other medications" does not qualify as a purchase and therefore cannot be added to member 102 total purchase volume for the year. "Other medications" are being added to member 102 list of medications at provider 104 database for the purpose of member 102 medication safety, and to continue building member 102 medical history. Specifically, a doctor at any partner hospital 106 or any doctor whether a partner/associate 106 or not, needs to know the present medications that member 102 is currently taking from home "home meds" so as not to have a possible complication with the introduction of newer medications that the attending doctor or other doctor will be prescribing to member 102. More specifically, certain drug combinations can be deadly and should be avoided at all costs.

Figure 10:
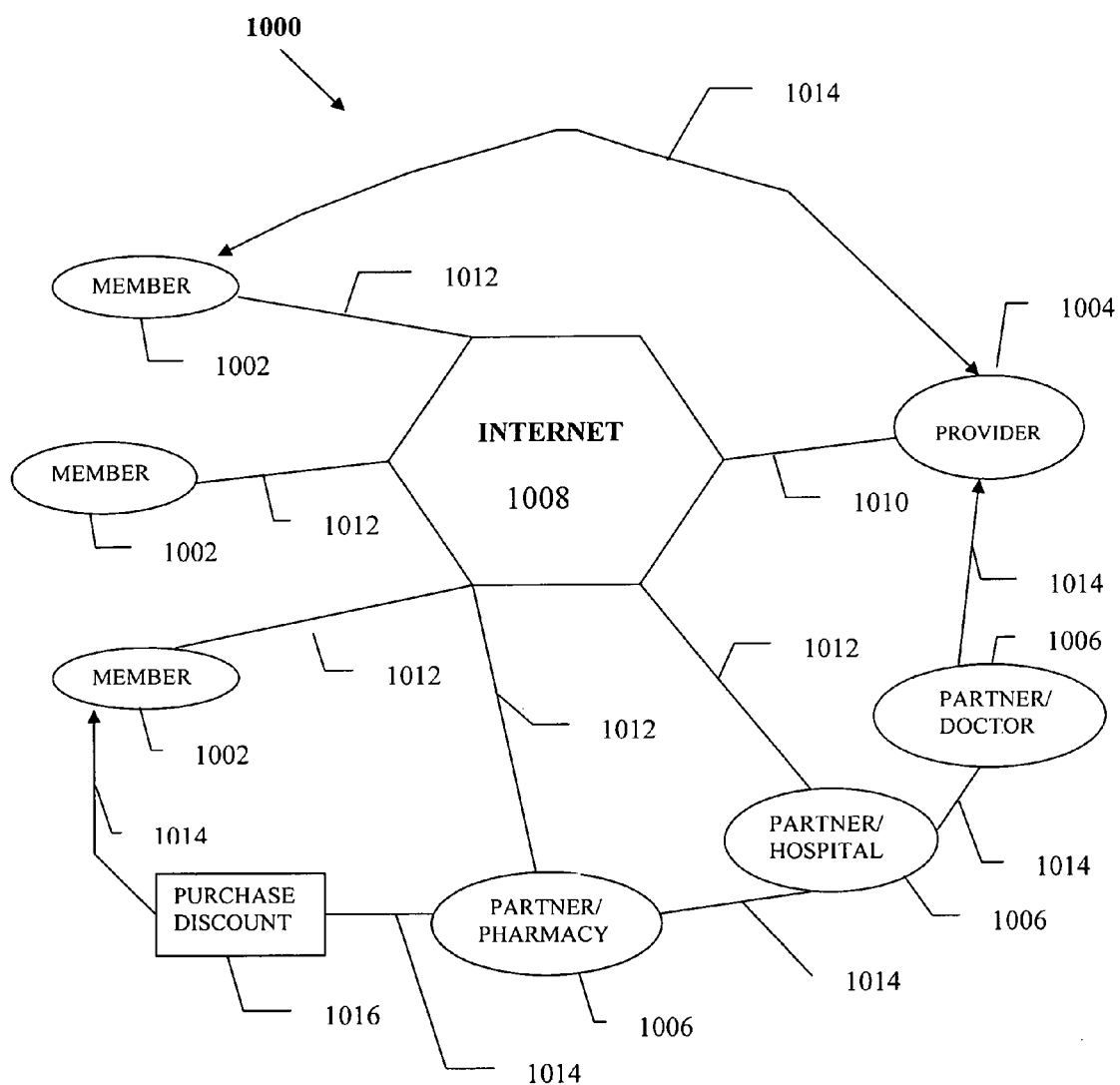
FIG. 10 is a diagram that depicts a way for members to enter listings of medications from home or home medications into a provider site.

FIG. 10 is a flow diagram 1000 that depicts a process whereby a set of members 1002 may enter their respective listing of medications from home or "home meds" into provider web site 1004. Member 1002 communicates with provider 1004 over links 1012, the global packet-switched network referred to as the "Internet" 1008 and a link 1010. Internet 1008 may be hard-wired or wirelessly connected. Links 1010 and 1012 may be any medium for transferring data between members 1002 and the Internet 1008, and between the Internet 1008 and the provider 1004, and between the Internet 1008 and partners/associates 1006, which may include a doctor, a hospital, a pharmacy or the like, and the invention is not limited to any particular medium. In the present example, links 1010 and 1012 may be connections provided by one or more Internet Service Providers (ISPs) and members 1002 and partners like doctors, hospitals, pharmacies 1006 or the like may be configured with generic internet web browsers. Links 1010 and 1012 may be secured or unsecured depending upon the requirements of a particular application.

In accordance with an embodiment, member 1002 signs up to become a member with provider 1004, and to enter the medications from home or "home meds" onto provider 1004 exclusive member-designated database, and to be afforded purchase discounts on medication purchases, health care professional services rendered or provided by any partner/associate 1006. For example, as previously described herein, "purchase discount" may apply without limitation to any commercial goods in addition to medication purchases from any partner pharmacy 1006, discounts on hospital charges from any partner hospital 1006, or discounts on professional health care services from any partner laboratory, radiology, physical therapy, home health providers 1006 or the like.

The invention is not limited to any particular approach for entering into membership agreement. For example, members 1002 and provider 1004 may enter into a membership agreement by mail, by telephone or over the internet, by members 1002 logging onto a web site associated with provider 1004 and using a graphical user interface (GUI). Members 1002 enter "home meds" listing unto provider 1004 designated member Level I database over links 1010 and 1012, and the Internet 1008 and using (GUI). Members 1002 may, as an option, send the listing of their respective medications from home or "home meds" to provider 1004 by mail, personal carriers, fax machines or the like. In turn, provider 1004 enters and adds the "home meds" into members 1002 designated Level I Database.

Members 1002 may, as another option, open up a secondary Level II Database by entering a secondary password onto provider 1004 web site over links 1010 and 1012 and the Internet 1008 and using GUI. In Level II database, members 1002 may enter without limitation, for example, addresses of family members, telephone numbers, anniversary dates, birthdates, recipes, bank accounts or the like. Members 1002 Level II Database records are confidential, and would only be editable and viewable by the member 1002 via entering the said secondary password. As described previously herein, Level I database can be accessed by any partner/associates 1006 if so authorized by member 1002, and that is for members 1002 medication safety in avoiding any accidental medication complications which may run the gamut from upset stomach to coma, or even death. Physicians have now recognized that some medications do not mix well with others. With the advent of ever-increasing array of prescription and over-the-counter medications and herbal supplements, the patients and doctors find themselves facing a growing problem of too many patients unwittingly taking dangerous combinations of drugs.

Members 1002 may also authorize, for example, a partner/doctor 1006 to send member 1002 a list of new medications or prescriptions to provider 1004 by delivery channel 1014, which may include but is not limited to the mail, telephone, personal carrier or the like. A partner/associate 1006 may also, by logging onto a web site associated with provider 1004 over links 1010 and 1012 and the internet 1008 and using a graphical user interface, transfer member 1002's list of medications or prescription over to provider 1004 Level I database. Other mediums for transferring member 1002 list of medications or prescriptions to provider 1004 may include, but is not limited to an FTP, an upload from partner/associate 1006 server to provider 1004 server. Partner/associate 1006 is illustrated as a single entity for purposes of description only. Partner/associate 1006 may be centralized or distributed depending upon the requirements of a particular application. For example, a partner/pharmacy 1006 may operate in one location. Alternatively, a partner/pharmacy 1006 may be implemented by a network of locations that may even include locations located in another state or another country.

Partner/doctor 1006 in some situations may be able to communicate the new listing of medications of member 1002 to a partner/pharmacy 1006 by delivery channel 1014, which may include, but is not limited to encrypted e-mail, telephone, personal carrier, server-to-server link, a member delivering to any partner or the like. A partner/doctor 1006 may also, by logging onto a web site associated with provider 1004 over links 1010 and 1012 and the Internet 1008, and using a graphical user interface, transfer the list of medications or prescription over to partner/pharmacy 1006. Other mediums for transferring member 1002 list of medications or prescriptions from partner/doctor 1006 to partner/pharmacy 1006 may include, but is not limited to an FTP, an upload from partner/doctor 1006 server to partner/pharmacy 1006 server. For authentication purposes, member 1002 may be required to show some form of identification to partner/pharmacy 1006 before the delivery of medications to member 1002 is completed. Some form of identification may include without limitation an identification card that bears the picture of the member 1002 that may include for example, a valid driver's license, a membership card called "medicard" as previously described above, that is issued by provider 1004, a valid passport or the like. In other situations member 1002 may even send an authorized representative to pay for and receive the new medications from partner/pharmacy 1006.

According to one embodiment, purchase discount 1016 may be implemented for example, by an agreement between provider 1004 and partner/pharmacy 1006 by granting member 1002 certain purchase discounts 1016 on purchases of medications from partner/pharmacy 1006. Provider 1004 will deliver the list of eligible members 1002 to a partner/pharmacy 1006 by delivery channel 1014 which may include, but is not limited to encrypted e-mail, telephone, personal carrier, member delivering to any partner or the like.

Provider 1004 may also by logging onto a web site associated with provider 1004 over links 1010 and 1012 and the Internet 1008 and using a graphical user interface transfer the list of eligible members 1002 over to partner/pharmacy 1006. Other mediums for transferring active member 1002 listing from provider 1004 to partner/pharmacy 1006 may include, but is not limited to an FTP, an upload from provider 1004 server to partner/pharmacy 1006 server. In situations where a partner/pharmacy 1006 needs to verify for an eligibility for purchase discount 1016 of a member 1002, partner/pharmacy 1006 may have the option of using the delivery channel 1014, for example, for quick response a telephone call to provider 1004 will be sufficient, and for some that require non-urgent action, then another delivery channel 1014 like e-mail, personal carrier or the like will suffice.

The purchase discount 1016 may be in a form of a percentage of the selling price of the medication. Purchase discount 1016 may include, but is not limited to purchases of medications, prescriptions, or any other commercial products that a partner/associate 1006 may sell or services that may be provided by partner/associate 1006 to member 1002. An example of a purchase discount may include, but is not limited to a range of percentages like 1% to 90% of the selling price of medications or other commercial items, but may also apply to whole dollar discount like $5.00 for medication purchases totaling $50.00 to $75.00, or $10.00 purchase discount may be applied to perhaps equipment purchases that are valued between $75.00 to $100.00.

Figure 11:
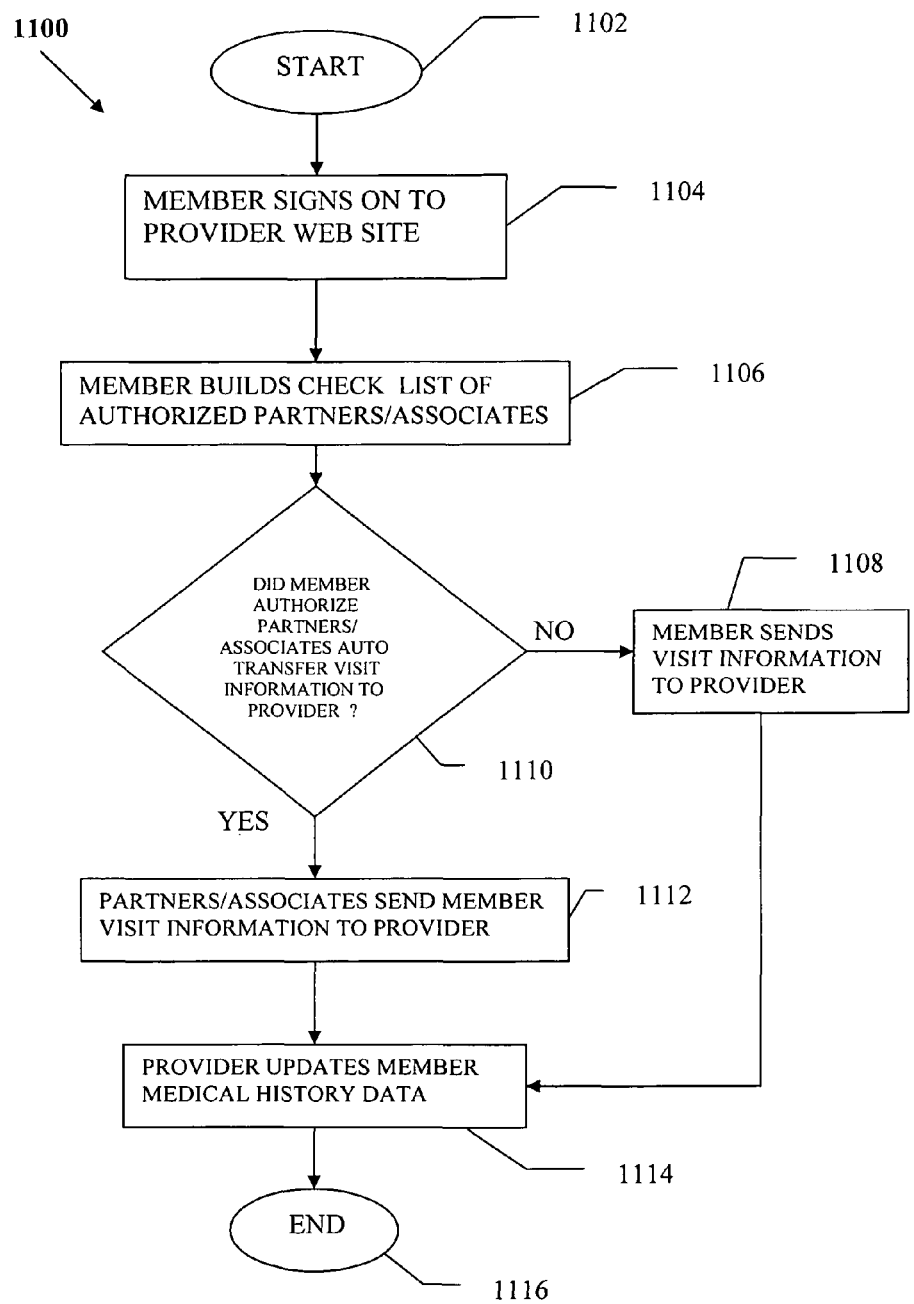
FIG. 11 is a flow diagram that illustrates the process of building up a medical history for a member in an embodiment of the invention.

FIG. 11 is a flow diagram 1100 that illustrates a process of building up a medical history for member 1002. Medical history may include, but is not limited to compilation of all medical diagnoses, procedures done, allergies, medications taken previously, medications presently being taken, vaccinations, x-ray taken or the like. After starting from step 1102, in step 1104, member 1002 signs up onto the provider 1004 web site entering password 1 over links 1010 and 1012 and the Internet 1008, and using a graphical user interface to access member 1002 Level I database. In step 1106 member 1002 enters the names of an authorized partner/associate 1006 who could send member 1002 medical information to provider 1004. In step 1110, a determination is made whether partner/associate 1006 is authorized to auto-transfer member 1002 medical information directly into provider 1004 server over links 1010 and 1012 and the Internet 1008, and using the GUI, and if so, then in step 1112 the transfer of member 1002 medical information data is sent by member/associate 1006 to member 1002 Level I database at provider 1004 web site. If however, in step 1110, the member 1002 did not authorize the partner/associate 1006 auto transfer of medical information to provider 1004, then in step 1108 member 1002 becomes responsible in sending member 1002 medical information to provider 1004 and in step 1114 provider 1004 provider updates member medical records and the process is then complete in step 1116.

Member 1002 may have the option of using delivery channel 1014, which may include, but is not limited to an email, postal mail, personal carrier, member delivering to any partner or the like in sending the medical information to provider 1004, and then in step 1114 provider 1004 updates member 1002 Level I database, and the process of building/updating member 1002 medical history file is then complete in step 1116.

The approach described herein for a members to be able to enter lists of their medications being taken from home and receive purchase discounts on purchases of medications, services or any other commercial products and print, transfer their respective listing of medications, are particularly well suited for Internet-based membership. The invention may be implemented in hardware circuitry, in computer software, or a combination of hardware circuitry and computer software and is not limited to a particular hardware or software implementation.

Figure 12:
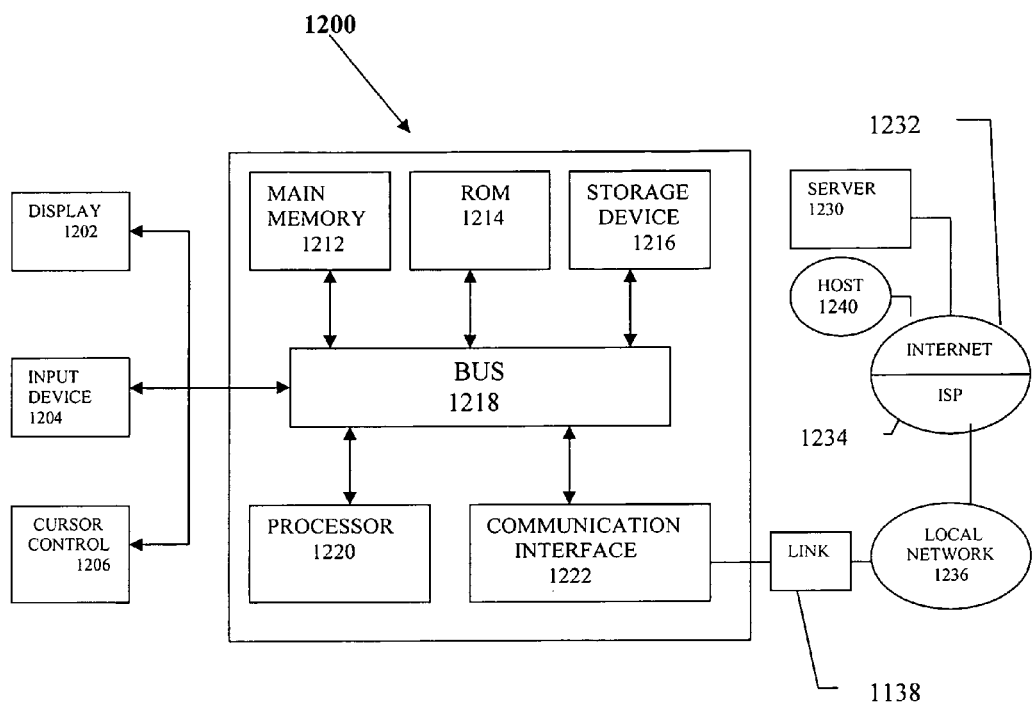
FIG. 12 is a block diagram that illustrates a computer upon which an embodiment of the present invention may be implemented.

FIG. 12 is a block diagram that illustrates a computer 1200 upon which an embodiment of the invention may be implemented. Computer 1200 includes a bus 1218 or other communication mechanism for communicating information, and a processor 1220 coupled with bus 1218 for processing information. Computer 1200 also includes a main memory 1212, which may include a random access memory (RAM) or any other dynamic storage device, coupled to bus 1218 for storing information and instructions to be executed by processor 1220. Main memory 1212 also may be used for storing temporary variables or other intermediate information during execution of instructions to be executed by processor 1220. Computer 1200 further includes a read only memory (ROM) 1214 or other static storage device coupled to bus 1218 for storing static information and instructions for processor 1220. A storage device 1216, which may include a magnetic disk or optical disk, is provided and coupled to bus 1218 for storing information and instructions.

Computer 1200 may be coupled via bus 1218 to a display 1202, such as a cathode ray tube (CRT), for displaying information to a computer user. An input device 1204, including alphanumeric and other keys, is coupled to bus 1218 for communicating information and command selections to processor 1220. Another type of user input device is cursor control 1206, such as a mouse, a trackball, or cursor direction keys for communicating direction information and command selections to processor 1220 and for controlling cursor movement on display 1202. This input device typically has two degrees of freedom in two axes, a first axis (e.g., x) and a second axis (e.g., y), that allows the device to specify positions in a plane.

The invention is related to the use of computer 1200 for members to enter the list of their medications, allergies, personal information and be able to print, transfer such listing of medications, allergies, personal information and receive purchase discounts on purchases of medications or any other commercial products. According to one embodiment of the invention, the entering, printing, transferring of members' medications as well as the receiving of purchase discount, is provided by computer 1200 in response to processor 1220 executing one or more sequence of one or more instructions contained in main memory 1212. Such instructions may be read into main memory 1212 from another computer-readable medium, such as storage device 1216. Execution of the sequence of instructions contained in main memory 1212 causes processor 1220 to perform the process steps described herein. One or more processors in a multi-processing arrangement may also be employed to execute the sequences of instructions contained in main memory 1212. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 1220 for execution. Such a medium may take many forms, including, but not limited to non-volatile media, volatile media, and transmission media. Non-volatile media includes, for example, optical or magnetic disks, such as storage device 1216. Volatile media includes dynamic memory, such as main memory 1212. Transmission media includes coaxial cables, copper wire and fiber optics, including the wires that comprise bus 1218. Transmission media can also take the form of acoustic or light waves, such as those generated during radio wave and infrared data communications.

Common forms of computer-readable media include, for example, a floppy disk, hard disk, a flexible drive, a flash drive, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 1220 for execution. For example, the instructions may initially be carried on a magnetic disk of a remote computer. The remote computer can load the instructions into its dynamic memory and send the instructions over a telephone line using a modem. A modem local to computer 1200 can receive the data on the telephone line and use an infrared transmitter to convert the data to an infrared signal. An infrared detector coupled to bus 1218 can received the data carried in the infrared signal and place the data on bus 1218, from which processor 1220 retrieves and executes the instructions. The instruction received by main memory 1212 may optionally be stored on storage device 1216 either before or after execution by processor 1220.

Computer 1200 also include a communication interface 1222 coupled to bus 1218. Communication interface 1222 provides a two-way data communication coupling to a network link 1138 that is connected to a local network 1236. For example, communication interface 1222 may be an integrated services digital network (ISDN) card or a modem to provide a data link communication connection to a corresponding type of telephone line. As another example, communication interface 1222 may be a local area network (LAN) card to provide a data communication connection to a compatible LAN. Wireless links may also be implemented. In any such implementation, communication interface 1222 sends and receives electrical, electromagnetic or optical signals that carry digital data streams representing various types of information.

Network link 1138 typically provides data communication through one or more networks to other data devices. For example, network link 1138 may provide a connection through local network 1236 to a host computer 1240 or to data equipment operated by an Internet Service Provider (ISP) 1234. ISP 1234 in turn provides data communication services through the world wide packet data communication network now commonly referred to as the "Internet" 1232. Local network 1236 and Internet 1232 both use electrical, electromagnetic or optical signals that carry digital data streams. The signal through the various networks and the signals on network link 1138 and through communication interface 1222, which carry the digital data to and from computer 1200, are exemplary forms of carrier waves transporting the information.

Computer 1200 can send messages and receive data, including program code through the networks, network link 1138 and communication interface 1222. In the Internet example a server 1230 may transmit a requested code for an application program through Internet 1232, ISP 1234, local network 1236 and communication interface 1222. In accordance with this invention, one such downloaded application provides for the member to enter the list of their medications as described herein.

The received code may be executed by processor 1220 as it is received, and/or stored in the storage device 1216, or other non-volatile storage for later execution. In this manner, the computer 1200 may obtain application code in the form of a carrier wave.

Figure 13:
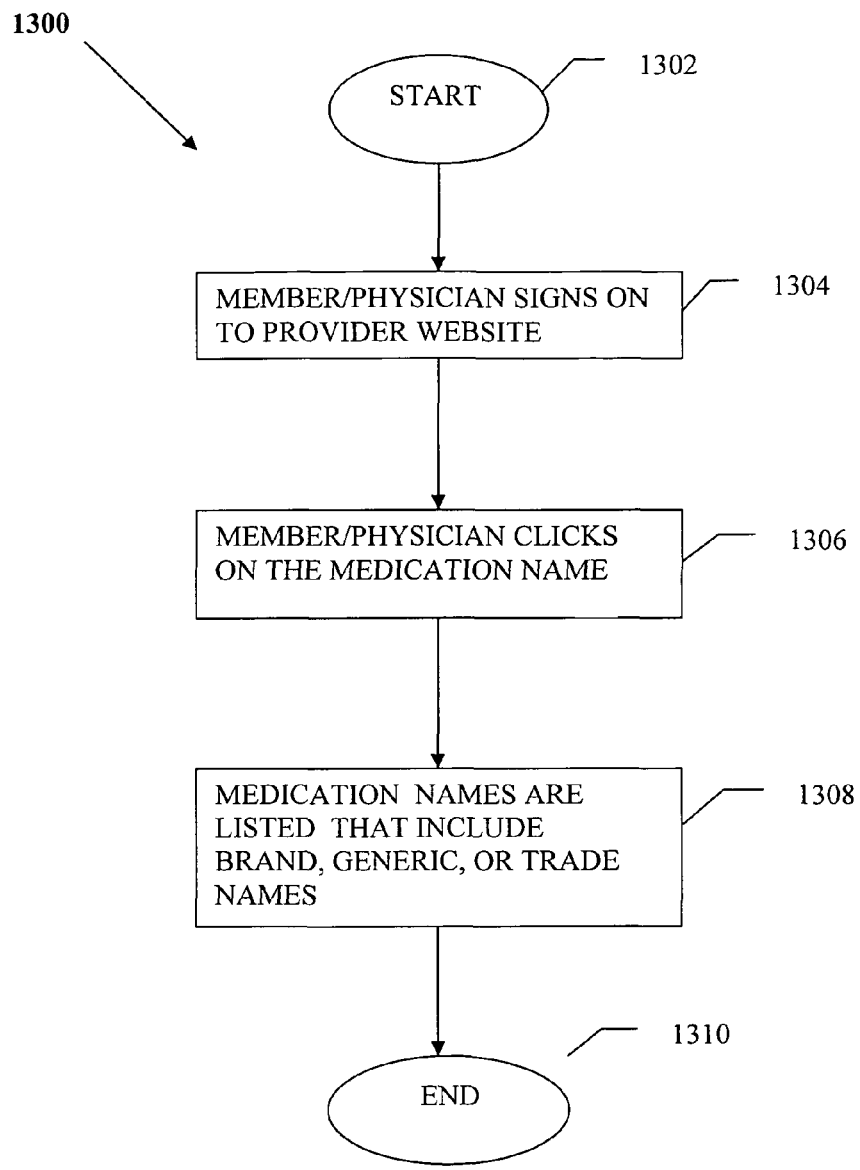
FIG. 13 is a look-up flow diagram to find a name for "other medications" in an embodiment of the present invention.

FIG. 13 is a flow diagram depicting look up for other medication's name 1300. After starting from step 1302, in step 1304, member 102 or the partner/associate/physician 106 signs on to provider 104 web site. Then in step 1306, according to another embodiment, the member or the physician then enters the drug or medication name or some other naming convention that may include but not limited to the drug or medication mnemonic which can be formed as an alphabetic, alphanumeric or some other acceptable abbreviations that can be stored in a database. An example would be in a form of a "Drug Dictionary". A drug dictionary can be defined as a listing of various medication fields that may contain but not limited to a drug mnemonic, a description, trade name, brand name, generic equivalent, side effects, purpose of medication, drug class, drug sub-class grouping, when is the best time to take this medication, the manufacturer, ingredients, drug type, control medication, restrictions, medication group names and/or any other relevant medication information. A medication group name field can be defined as a common field or two or more fields that will link one drug to another drug by way of an identifying code.

An identifying code for example, may be the first field of the drug dictionary which may contain a drug mnemonic that when selected a secondary selection may be provided with or without limitation, such as listing the other names of the drug. For example, when in use as shown in step 1308, when the member 102 or partner/associates 106 enters a mnemonic of "atoriota" the trade name "lipitor" along with the generic name of "atorvastatin" are displayed. On the other hand, when the member or partner/associate enter the trade name "lipitor" then the mnemonic of "atoriota" and generic name of "atorvastatin" are displayed or if the member or partner/associate enters the generic name of "atorvastatin", then mnemonic of "atoriota" and trade name "lipitor" are displayed. By providing the member the necessary tool to question the doctor for possible drug duplication or for the doctor to avoid prescribing duplicate medication of a drug by knowing exactly the drugs that the member 102 is currently taking will eliminate the chances of drug overdosing.

In addition to the above, when drugs lipitor and atorvastatin are prescribed at the same time to a member 102 further illustrates that overdosing can occur in incapacitation of member 102, which could have been prevented by adopting an effective warning protocol of MedTrack and the process is then complete in step 1310.

Figure 14:
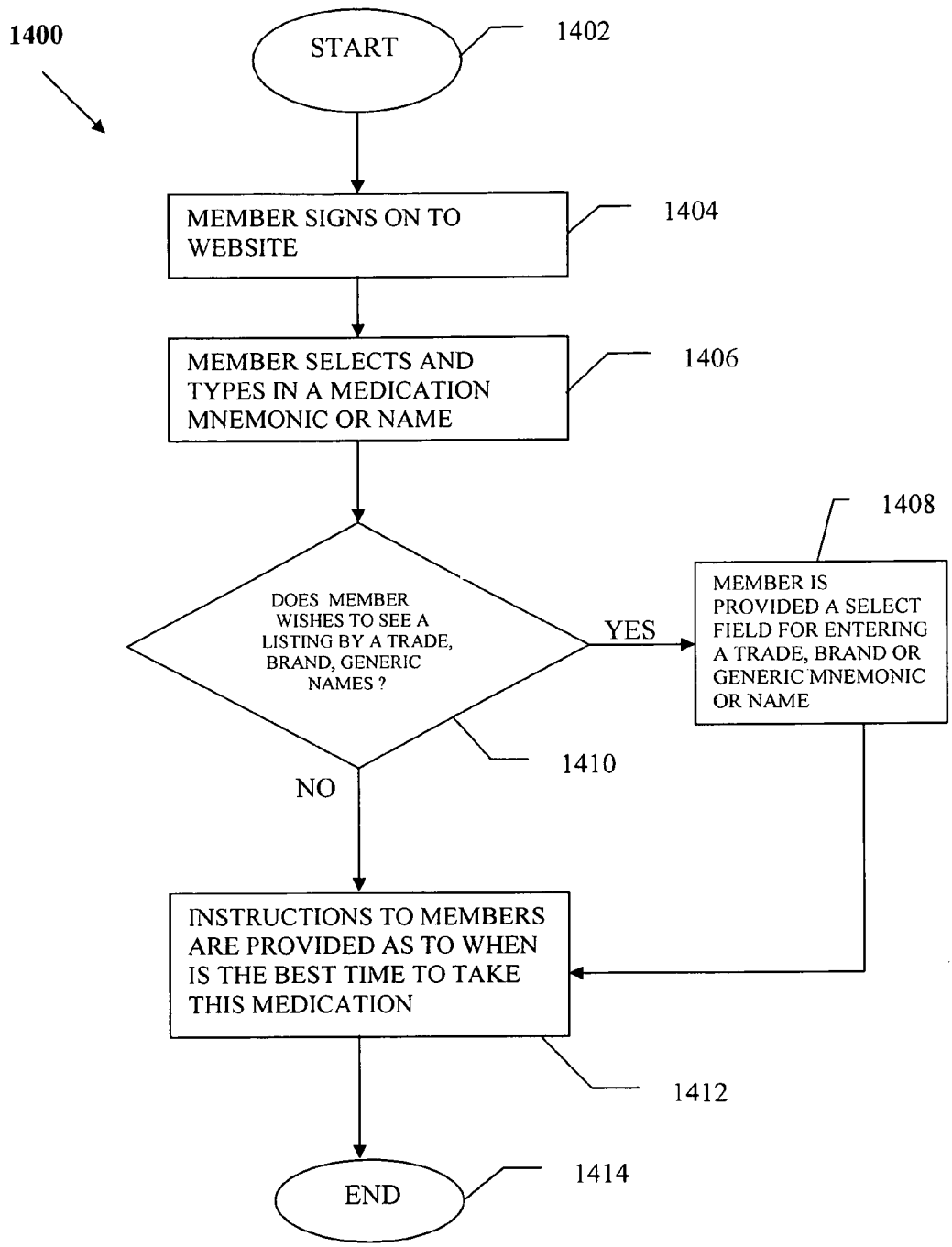
FIG. 14 is a flow diagram that illustrates a method for informing a member as to when is the best time to take a medication.

FIG. 14 is a flow diagram 1400 that illustrates to member 102 as to when is the best time to take a medication. After starting in step 1402, in step 1404, the member 102 signs on to provider 104 web site. According to one embodiment, in step 1406, the member decides, selects and enter the medication mnemonic or name into the provider (provider 104 patients database MedTrack via the interne or link 108) that will provide the member the instructions as to when is the best time to take a specific medication. The best time to take a medication can be defined as taking the medication at its most potent time for the medication to be fully effective. For example, some medications may be more effective if taken before a meal or some would be more effective if taken after a meal or if taken with an empty stomach. In step 1410, a determination is made whether the member wishes to see the listing either by trade or generic names, then in step 1408, the member is given the option of selecting a field that could be either a trade or generic name and the member 102 in step 1412 is provided with the instructions as to when is the best time to take such medication selected thus the process is complete in step 1414.

If however, in step 1410, the member does not want to be provided a select field for either trade or generic, then step 1412 prints the instructions as to the best time to take such medication as selected in step 1406, and the process is complete in step 1414.

Figure 15:
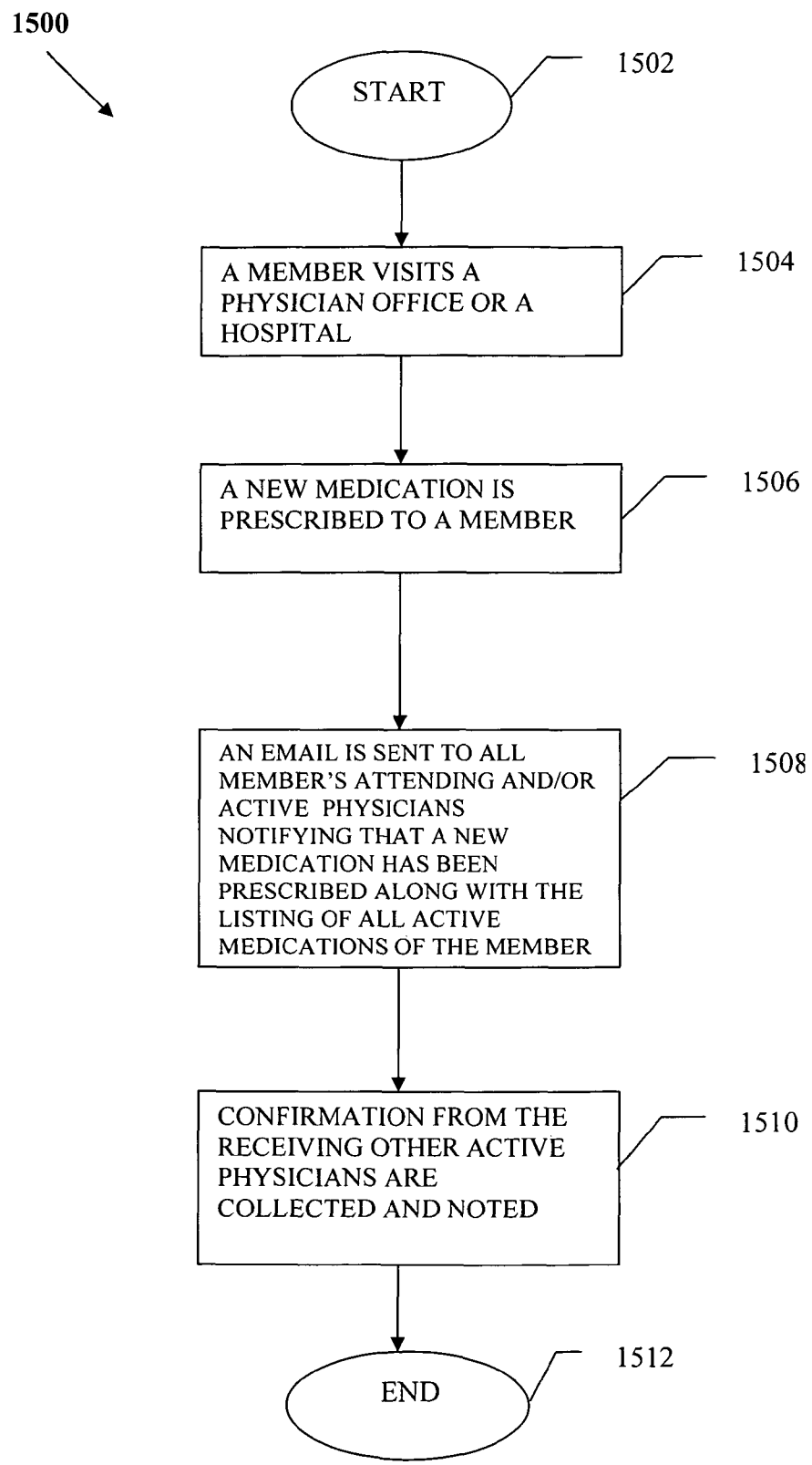
FIG. 15 is a flow diagram that depicts a feature for automatically sending an email to other active physicians of the member if a new medication is prescribed.

FIG. 15 is a flow diagram 1500 that illustrates a process for automatically sending an email to other active physicians of the member 102 if a new medication is prescribed. After starting in step 1502, in step 1504 the member visits a physician's office or a hospital. According to another embodiment, in step 1506, in situations where the member visits a physician's office and after a thorough medical examination of member 102, the physician decides to prescribe a new medication for the member, then in step 1508, the issuance of such new medication triggers an automatic sending of an email to all active members attending physicians along with the current listing of all active medications being taken by said member, and the member's medications database MedTrack is updated. The prescription of new medication may be sent by the prescribing physician via delivery channel 110 which may include, but is not limited to an automated electronic prescription to provider 104 wholly owned subsidiary medication depot, or to any partner/associate 106. The e-prescription provided will incorporate and meets the requirements of HIPAA act of 1996 in regards to "Security Standards for the Protection of Electronic Protected Health Information" which may include, but is not limited to privacy rule, electronic transaction and code sets rule, national identifier requirements for providers and health plans, security rule and other rules that may apply. For example, the e-prescription will authenticate the prescription order by certain member 102 like the first plus last four digits of member 102 social security number and/or physician 106 first initial plus first four digits of last name, can be used as the combination code to authenticate each prescription order. This order will then be sent via secured multi-layered encryptions for additional security and protection which can be via an INTERNET 1008 or any other medium of transmission, in other situations where the member 102 gets admitted to a hospital either as an inpatient or as an outpatient. Upon member 102 discharge from said hospital, the member's medication database located at provider 104 MedTrack is updated reflecting the addition of new medications. In step 1510, confirmations of receipts of auto-email for the issuance of new medication sent to active physicians are collected and noted, then the process is complete in step 1512.

Figure 16:
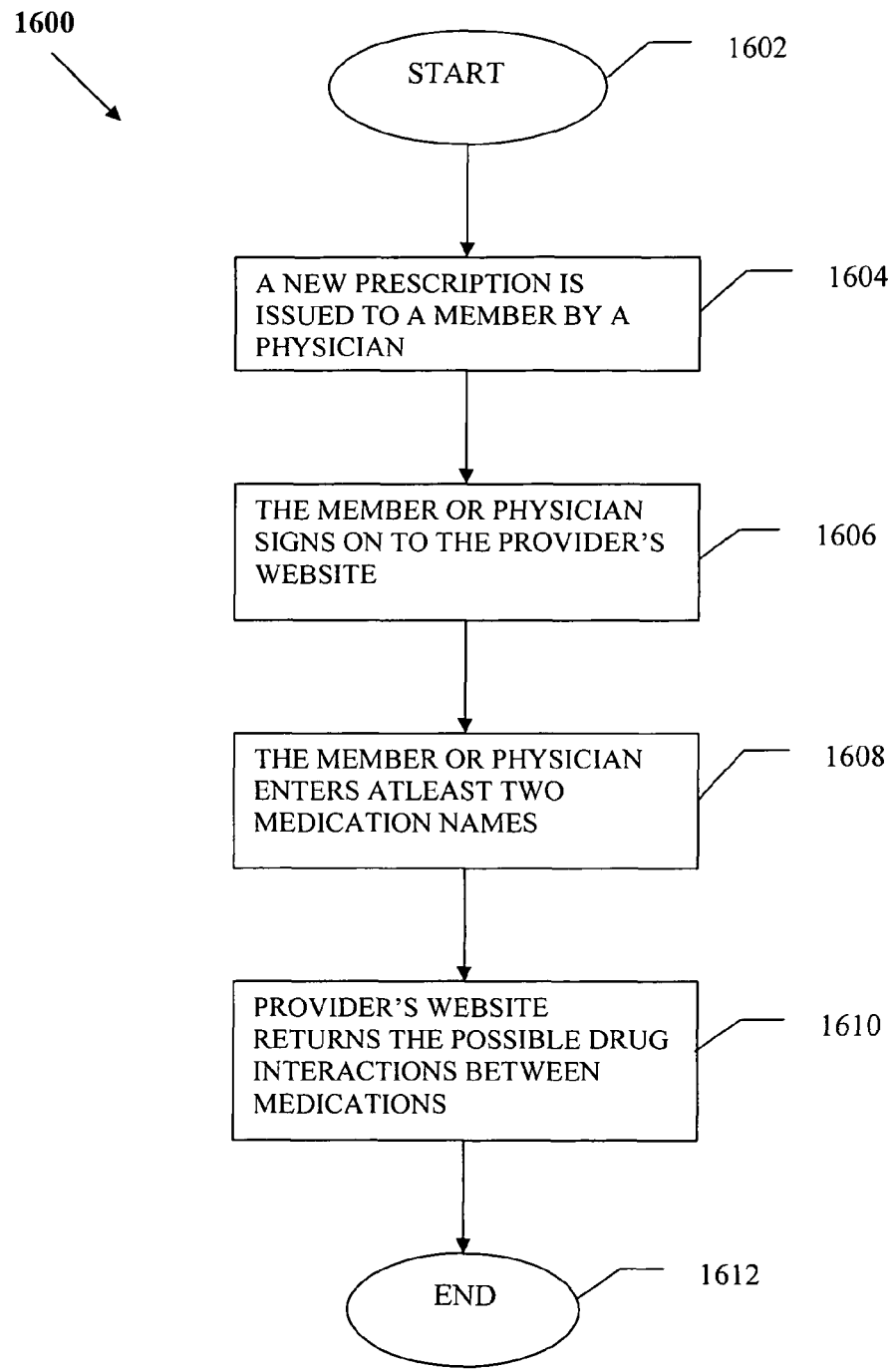
FIG. 16 is a flow diagram that illustrates a process for listing of possible drug interactions between two or more medications if taken together at same time or same day.

FIG. 16 is a flow diagram 1600 that illustrates a process that provides a listing of possible drug interactions between two or more medications if taken together at same time or same day. After starting in step 1602, when a new prescription is issued to a member 102 by a physician 106 as shown in step 1604, and in step 1606, member 102 or physician 106, then signs on to provider 104 web site. In step 1608, once the member 102 or the physician 106 has signed on into provider 104 web site, the member or the physician has to enter the mnemonic or the name of the new medication that was just prescribed. The MedTrack in step 1610, then automatically checks and prints the food and/or drug interactions of the new medication with that and all of the active medications that member 102 is currently taking. For example, if the new medication name is "lipitor" and one of the current active medication name is "clarithromycin" and with a "drug to drug" interaction the simultaneous taking of prescription drugs "lipitor and "clarithromcycin" may elevate the plasma concentrations of "HMG-CoA" reductase inhibitors that are metabolized by the isoenzyme resulting in the development of severe myopathy. As another example, the MedTrack may provide member 102 and/or physician 104 food interaction of the new medication. Member 102 receiving therapy with "atorvastatin" or "lovastatin" should be advised to avoid the regular consumption of large amounts of grapefruits and grapefruit juice which could cause an unexplained muscle pain, tenderness or weakness. Provider 104 web site then returns the possible drug to drug or food to drug interactions that could be viewed on the computer screen, or prints them out to any attached printer and then the process is complete in step 1612.

Figure 17:
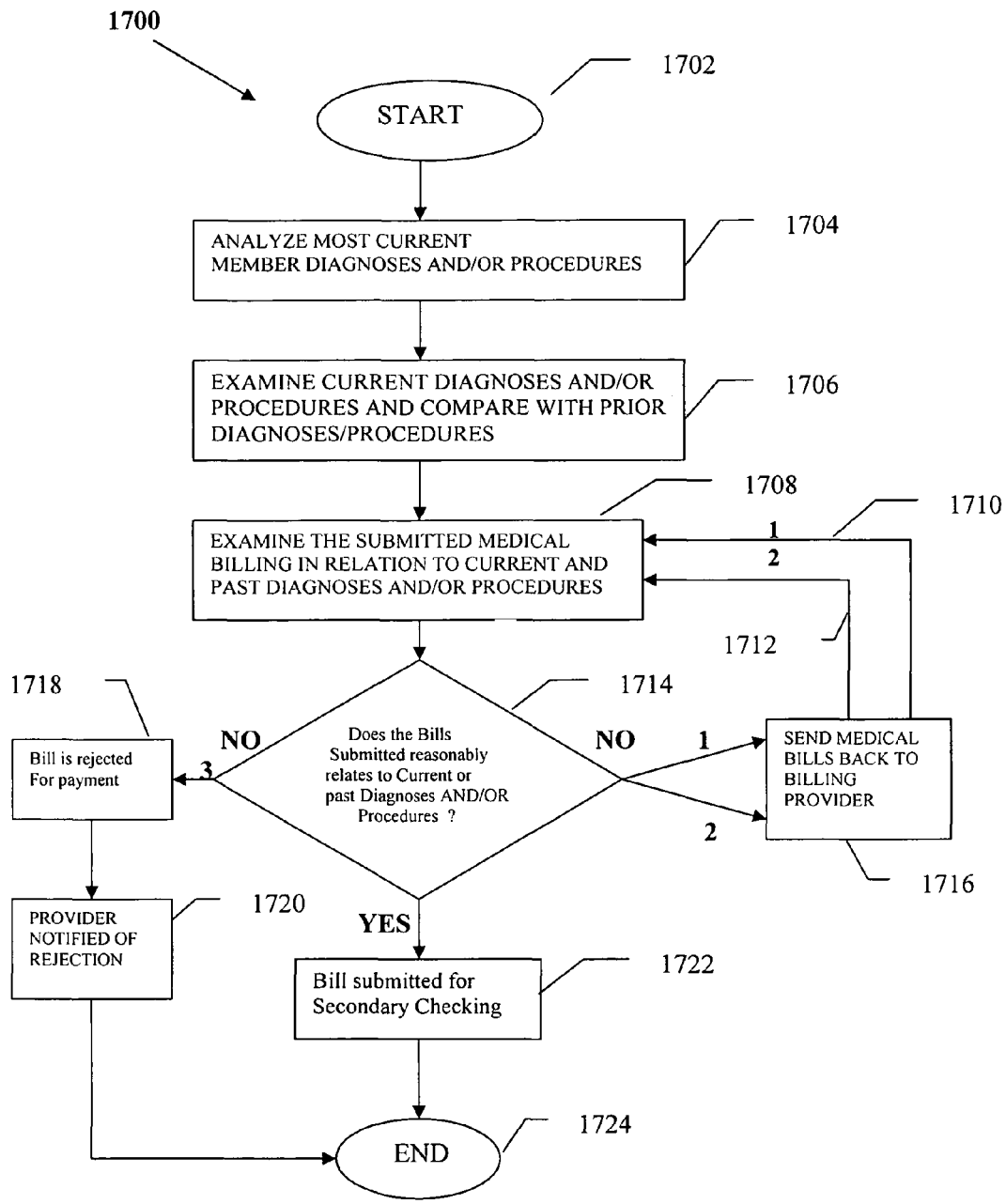
FIG. 17 is a flow diagram that illustrates an audit for submitted third party medication billed charges.

FIG. 17, according to an embodiment, is a flow diagram 1700 that illustrates a process for an audit for submitted third party medication billed charges. Third party is defined as any professional service organization or organizations provider that may include, but is not limited to physicians, pharmacies, physical therapies, laboratories, radiologists, oncologists, psychiatrists, medical equipment suppliers or the like. After starting in step 1702, in step 1704, provider 104 MedTrack analyzes the past and current member 102 diagnoses and/or procedures. A thorough analysis is performed by provider 104 to establish a base line protocol for each and every diagnoses or procedures that the member 102 had, the purpose of which is to make sure that all medical bills submitted by various third party providers are legitimate goods or services that are not only actually been delivered and services rendered but also necessary, and such submitted medication billed charges relate reasonably to one or more of the member 104 past or present diagnoses and/or procedures that had been done previously. For example, as a feature of MedTrack, for each diagnosis that a member 102 had, a corresponding list that may include, but is not limited to the approved medications, supplies, equipment, or a list of professional services rendered and other related items are automatically listed for easy auditing. The same way is true for member 102 past or present procedures done, where the corresponding list that may include but limited to the approved medications, supplies, equipment or a list of professional services rendered and other related items are automatically listed for easy auditing. In step 1706, provider 104 examines the member 102 current diagnoses and/or procedures and compare with the prior diagnoses or procedures.

In continuing step 1708, as previously described herein, provider 104 applies the "reasonableness test" of MedTrack to the medical billing charges submitted by any third party providers then in step 1714, a determination is made whether the medical billing charges submitted by third party providers meets "reasonableness test" relating to current or past diagnoses and/or procedures along with the approved required frequency, and if it does then in step 1722 the medical billing is submitted for secondary checking and the process is complete in step 1724.

If however, in step 1714, the submitted medical billed charges do not meet the required "reasonableness test", then in step 1716, as shown instep 1710 the first rejection of the submitted medical billing charges is sent back to the third party provider for additional information and upon resubmission of the medical bill charges for the second time, as shown in step 1712 then the control returns to step 1708. Provider 104 then applies the second "reasonableness test" and in step 1714, a second determination is made whether the re-submitted medical billing charges as shown in step 1712 now meets the "reasonableness test", and if it passes, then in step 1722, the bill is submitted for secondary checking and the process is complete in step 1724.

But if in step 1714, after a determination has been provided by provider 104 that the secondary medical bill re-submitted charges for the second time does not meet the reasonableness test", as shown in step 1712 then in step 1718 the medication billed charges is rejected for payment, then in step 1720, the third party provider is notified of the rejection and the process is then complete in step 1724. For example, a third party provider submitted a medical bill for a second a wheel chair, and after applying provider 104 "reasonableness test" the MedTrack notifies the provider 104 that the submitted medical billed charges do not pass its "reasonableness test", because another wheel chair has been paid to this third party provider a couple of months before. Upon examination by the MedTrack, it points out that based on the diagnoses and/or procedures (passed and present) establishes that member 102 will only be needing another wheel chair in the next three to five years period. As another example, the MedTrack could also have prevented the payment for another wheel chair, if the medical billed charges are submitted even without actual delivery of the second wheel chair to member 102, because MedTrack checks for delivery of items before approval is authorized for payment.

Figure 18:
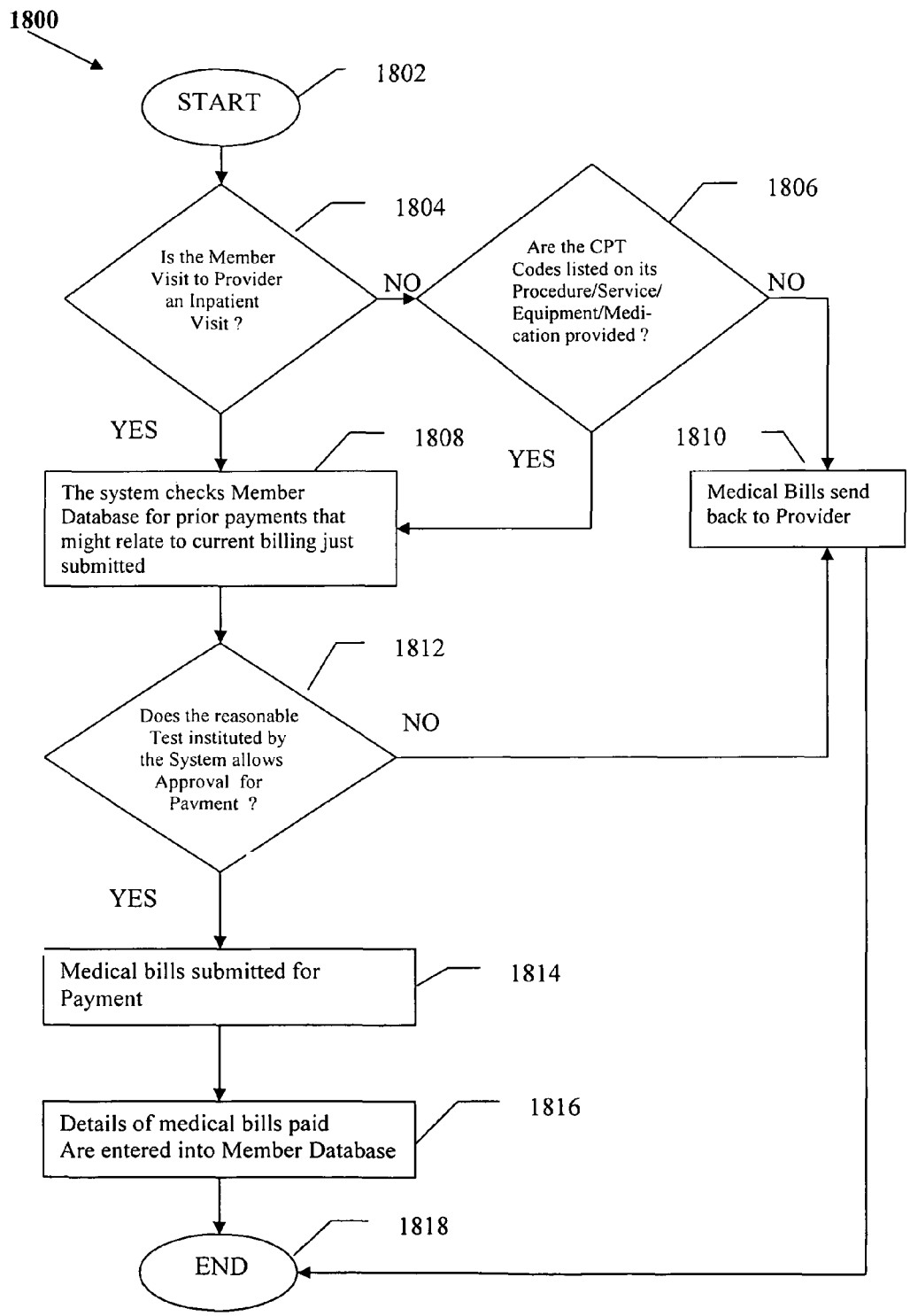
FIG. 18 is a flow diagram that illustrates a method for secondary checking of medication billed charges submitted by any third party providers before final approval for payment is authorized.

FIG. 18 is a flow diagram 1800 that illustrates the method for secondary checking of medication billed charges submitted by any third party providers before final approval for payment is authorized. The MedTrack classifies the member 102 submitted medication billed charges as either as an inpatient or outpatient medication billed charges. Inpatient medication billed charges is defined as billed charges incurred while a member 102 has been admitted to a hospital that lasted at least twenty four hours. Inpatient medication billed charges may include but not limited to hospital charges like room, laboratory, medication charges or the like, attending Doctors service fees or the like. Outpatient medication billed charges is defined as billed charges incurred by member 102, which may include, but is not limited to visiting a doctor's office for medical consultation or check up, physical therapies, medication purchases, laboratory visits, radiologic visits, medical equipment purchases, hospital visits where the member 102 check in the hospital and goes home same day and some other related charges.

According to another embodiment, after starting in step 1802, in step 1804, a determination is made as to whether member 102 visit is an inpatient or an outpatient, and if it is an inpatient, then in step 1808, the MedTrack checks member 102 database for prior payments made that may relate to current billing being submitted for payment, and after thorough evaluation then another determination is made in step 1812, there the MedTrack applies the reasonableness test by comparing the member 102 prior diagnoses and/or procedures, past or present in relation to the current billing submitted by any third party provider and if it passes the reasonableness test, then in step 1814, the bill is submitted for payment and in step 1816, the details of the medical bills that is being paid are entered into member 102 MedTrack and the process is complete in step 1818.

For example, if member 102 had visited a hospital as an inpatient with a chief complain of "Appendicitis", with an admitting diagnosis recorded of (541-Appendicitis Nos) that needed a surgical procedure done (47.01-Laparoscop Appendectomy) with a corresponding (CPT Code 44970-Laparoscopy, Appendectomy) will be the basis for reasonable medical charges billing. This medical charges billing may include incidentals like laboratory charges, room charges, medication charges or other reasonable charges that may seem to be appropriate. If, in step 1812, a determination is made that the medical bills submitted for payment does not meet the reasonableness test by MedTrack, then the control returns to step 1810, where the submitted medical billed invoice is sent back to the third party provider and the process is complete in step 1818.

If however, in step 1804, after a determination is made that member 102 is not an inpatient, then in step 1806, a determination is made to determine whether a CPT code is associated with the description of each line of each item billed charges and if it meets the requirement, the control transfers to step 1808, the MedTrack checks member 102 database for prior payments made that may relate to current billing being submitted for payment and after thorough evaluation then another determination is made in step 1812, where the MedTrack applies the reasonableness test by comparing the member 102 prior diagnoses and/or procedures, past or present in relation to the current billing submitted by any third party provider and if it passes the reasonableness test, then in step 1814, the bill is submitted for payment and in step 1816, the details of the medical bills that are being paid are entered in member 102 MedTrack database and the process is complete in step 1818. For example, if member 102 visits a doctor's office for an intolerable headache, and after the physician's medical diagnosis was done, it has been determined that primary diagnosis is (784.0-Headache). With this diagnosis of (784.0) a corresponding (CPT code 99282-Doctor visit) is generated. Any other medical bill charges submitted should be examined before authorizing payment.

If, in step 1812, a determination is made that the medical bills submitted for payment do not meet the reasonableness test by MedTrack, then the control returns to step 1810, where the submitted medical billed invoice is sent back to the third party provider and the process is complete in step 1818. If, in step 1806, a determination is made to determine whether a CPT code is associated with the description of each line of each item billed charges and if it does not meet the requirements, then the control goes to step 1810 where the medical bills submitted charged invoice is returned to the third party providers and the process is complete in step 1818.

Figure 19:
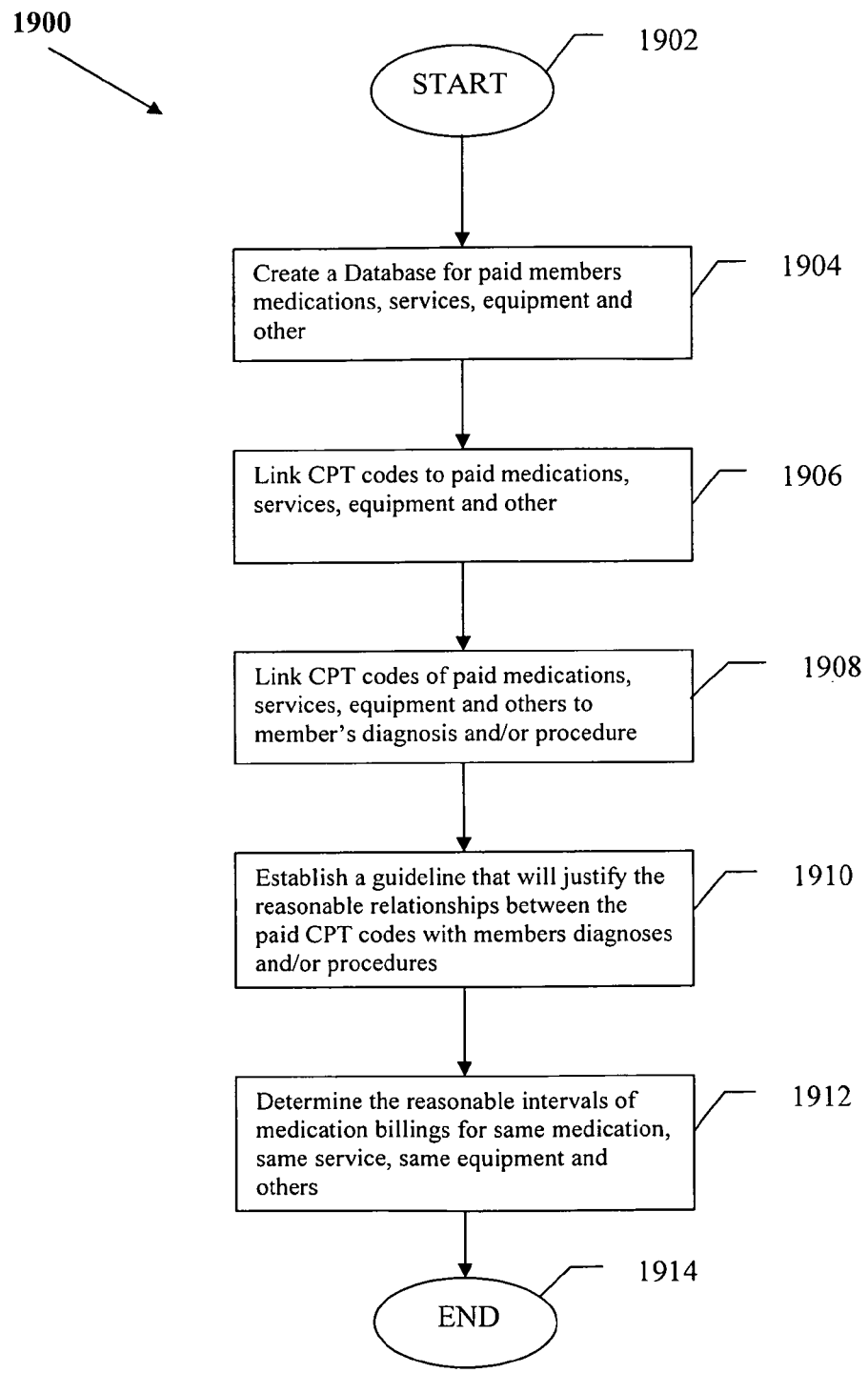
FIG. 19 is a flow diagram that illustrates elements and mechanism of a MedTrack in an embodiment of the invention.

FIG. 19 is a flow diagram 1900 that illustrates the contents and mechanism of MedTrack. The MedTrack is defined as the automated searching tool that warns and checks for drug interaction of a new medication with that of all other active medications, provides the instructions as to when is the best time to take a medication for member 102 or any other authorized user. The MedTrack is defined further as the tool that compiles listing and pairing of medication trade names with that of the its corresponding generic or brand names, collects and provide listing of allergies, which could be a drug or a medication allergy, links CPT codes to paid medications, services, equipment and others, links CPT codes of paid medications, services, equipment purchases and others with that of member 102 diagnoses and/or procedures (past and present). The MedTrack is further defined as "reasonableness test" in the examination of the details of submitted medical billing charges by any third party providers by following the established database guidelines developed by provider 104 which automatically lists all approved legitimate goods and/or services along with its reasonable frequencies that reasonably relates to a member 102 diagnosis or procedure past or present) or the combination thereof.

The MedTrack is being further defined as a warning and checking mechanism that analyzes medication, dose, route, frequency and purpose. For example, the MedTrack has a capability to forewarn member 102 or and partner/associate wholly-owned subsidiary 106 that the dose, route, frequency, and the like are not within a reasonable specification that has been established by the medication manufacturer, or other responsible authority. This process thus guides member 102, partner/associate wholly-owned subsidiary 106 or any other authorized user to enter the dose, route, frequency and the like correctly into provider 104 Level-1 Database using Password 1. Any entries that are not within the dose, route, frequency or the like guidelines will not be allowed to continue unless the entry or entries are corrected to within the guidelines, such as the manufacturer's established ranges. As an additional capability, member 102 or the wholly-owned subsidiary 106 would be able to double-check the dose, route, frequency and the like that has been provided by partner/associate physician or pharmacy 106. In situations where a conflict occurs between MedTrack and the new medication that had just been prescribed, provider 104 will research the issue and find out the true dose, route, frequency and the like, and make the necessary corrections if needed. A friendly reminder is then sent to member 102, partner/associate wholly-owned subsidiary 106, as to the true and correct dose, route, frequency or the like for the newly-prescribed medication. The aforementioned MedTrack is constantly being upgraded, corrected, adjusted and/or new items added or deleted as the need arises.

After starting in step 1902, in step 1904, provider 104 creates a member 102 database for paid medications, services rendered, equipment purchases or the like, along with their respective dates of payments, while in step 1906, the MedTrack links the CPT codes to each and every paid medications, services, equipment or the like. In step 1908, MedTrack also links the CPT codes of paid medications, services rendered, equipment purchases or others with member 102 respective diagnoses and/or procedures (past or present). This process is being done to assure that member 102 will only pay medical billed charges that are billed legitimately and without fraud, malice, erroneous billing, erroneous double billing or other non approved medical charges. In step 1910, MedTrack establishes a guideline that will justify the reasonable relationships between the paid CPT codes with that of member 102 diagnosed and/or procedures (past or present). An established protocol is followed, for example, by a member 102, visiting a hospital or a doctor office for a fever check up. The front office staff entered an admitting diagnosis of (780.6-Fever). The examining physician had determined that member 102 will have a final diagnosis of (487.1-Flu with respiratory manifest nec). Accordingly, based upon the final diagnosis of 487.1, billing charges that are allowable without questions refer to (CPT code J1885-Ketorolac injection) and a (CPT code 99282-Emergency visit charge). Any laboratory charges, medicinal equipment charges will now be questioned before payments are authorized. MedTrack will continue to update, change, add or delete items or process the protocol established for all diagnoses that have been identified and will be identified in the future.

Another important aspect of protecting member 102 against any fraudulent, erroneous, duplicated or any dubious medically billed charges presented for payment by any third party providers is shown in step 1912, where the MedTrack determines the reasonable intervals of medication billings for same medication, same service, same equipment or the like. For example, supposing member 102 previously ordered twenty four (24) "lipitor" tablets which has already been paid previously, and a month later the same third party provider sends another medication billing charge for twenty four (24) "atorvastatin" tablets which is the generic name for "lipitor". The "MedTrack" then based on its logarithmic capability will determine that the reasonable interval and the shipment of same medication having two different names triggers an email to send member 102 and provider 104, as a reminder to double check this medication billing charges for accuracy and legitimacy, then the process is complete in step 1914.

Figure 20:
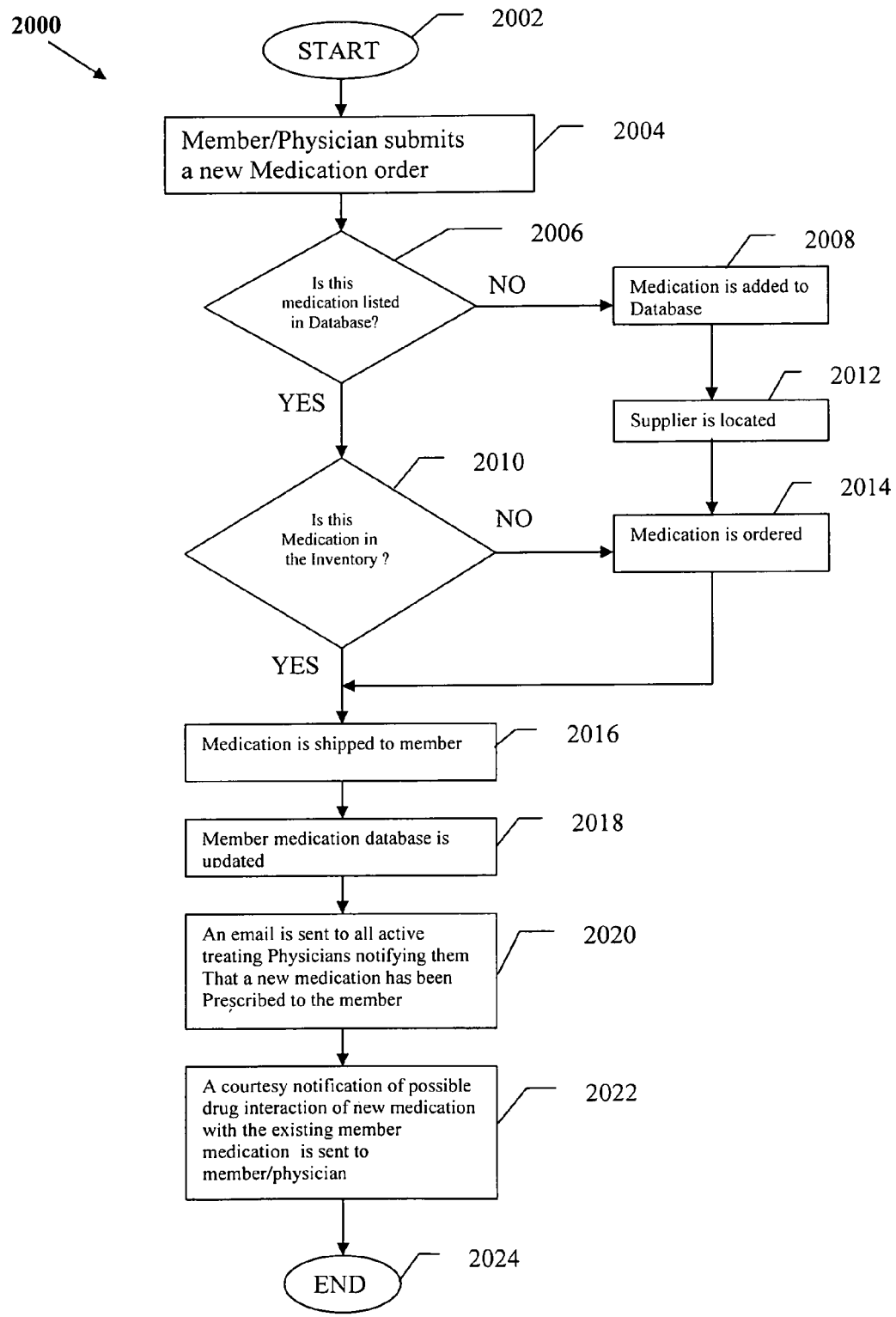
FIG. 20 is a flow diagram that illustrates prescription medication inventory control for a wholly owned subsidiary according to one embodiment of the invention.

FIG. 20 is a flow diagram 2000 that illustrates a process for prescription medication inventory control for a wholly owned subsidiary. The wholly owned subsidiary may be operated in the U.S.A or at any place in the world, or it can be centralized or distributed. In addition to providing member 102 the convenience of entering, adding, modifying, activating, deactivating medications and printing such home medication listing, can also authorized physicians, other authorized medical professionals or any other authorized users to view, print the listing of medications being taken from home by a member 102. Provider 104 may sell to member 102 any commercial products that may include but not limited to prescription medications, pharmaceutical supplies, over the counter medications, medical equipment and supplies or the like at wholesale price plus freight from any of the wholly owned subsidiary locations in the U.S.A. or any place in the world to any member 102 addresses that are located in U.S.A. or at any place in the world.

After starting in step 2002, in step 2004 a member 102 or a physician submits a new medication order for member 102. In step 2006, a determination is made whether the new medication order is in the database MedTrack. If it is then in step 2010, a determination is made whether the new medication on order is the inventory. In this situation, if the new medication on order is in the inventory, then in step 2016, the medication is shipped from the wholly owned subsidiary location in the U.S.A. or at any place in the world to member 102 address in the U.S.A. or any place in the world, then member 102 database is updated with new medication shipped in step 2018. In step 2020, an email is sent to all active treating physicians notifying them that a new medication has been prescribed and delivered to member 102, and in step 2022, a courtesy notification of sending a list of all possible drug or food interactions, drug or food allergies of the new medication with the existing active medication of member 102 is sent to the member and/or all active physicians and the process is complete in step 2024.

If however, in step 2006, after a determination is made that the new medication is not listed in MedTrack database, then in step 2008, the new medication is added to the database, in this case supplier is located in step 2012 then in step 2014, the medication is ordered. In this situation, upon receipt of new medication from the supplier, then in step 2016, the medication is shipped from the receiving wholly owned subsidiary location in the U.S.A. or at any place in the world to member 102 address in the U.S.A. or any place in the world, then member 102 database is updated with new medication shipped in step 2018. In step 2020, an email is sent to all active treating physicians notifying them that a new medication has been prescribed and delivered to member 102, and in step 2022, a courtesy notification of sending a list of all possible drug or food interactions, drug or food allergies of the new medication with the existing active medication of member 102 is sent to the member and/or all active physicians and the process is complete in step 2024.

If, in step 2010, after a determination is made that the new medication being ordered is not in the inventory, then medication is ordered in step 2014, and in this situation, upon receipt of new medication from the supplier, then in step 2016, the medication is then shipped from the receiving wholly owned subsidiary location in the U.S.A. or at any place in the world to member 102 address in the U.S.A. or any place in the world, then member 102 database is updated with new medication shipped in step 2018. In step 2020, an email is sent to all active treating physicians notifying them that a new medication has been prescribed and delivered to member 102, and in step 2022, a courtesy notification of sending a list of all possible drug or food interactions, drug or food allergies of the new medication with the existing active medication of member 102 is sent to the member and/or all active physicians and the process is complete in step 2024.

Figure 21:
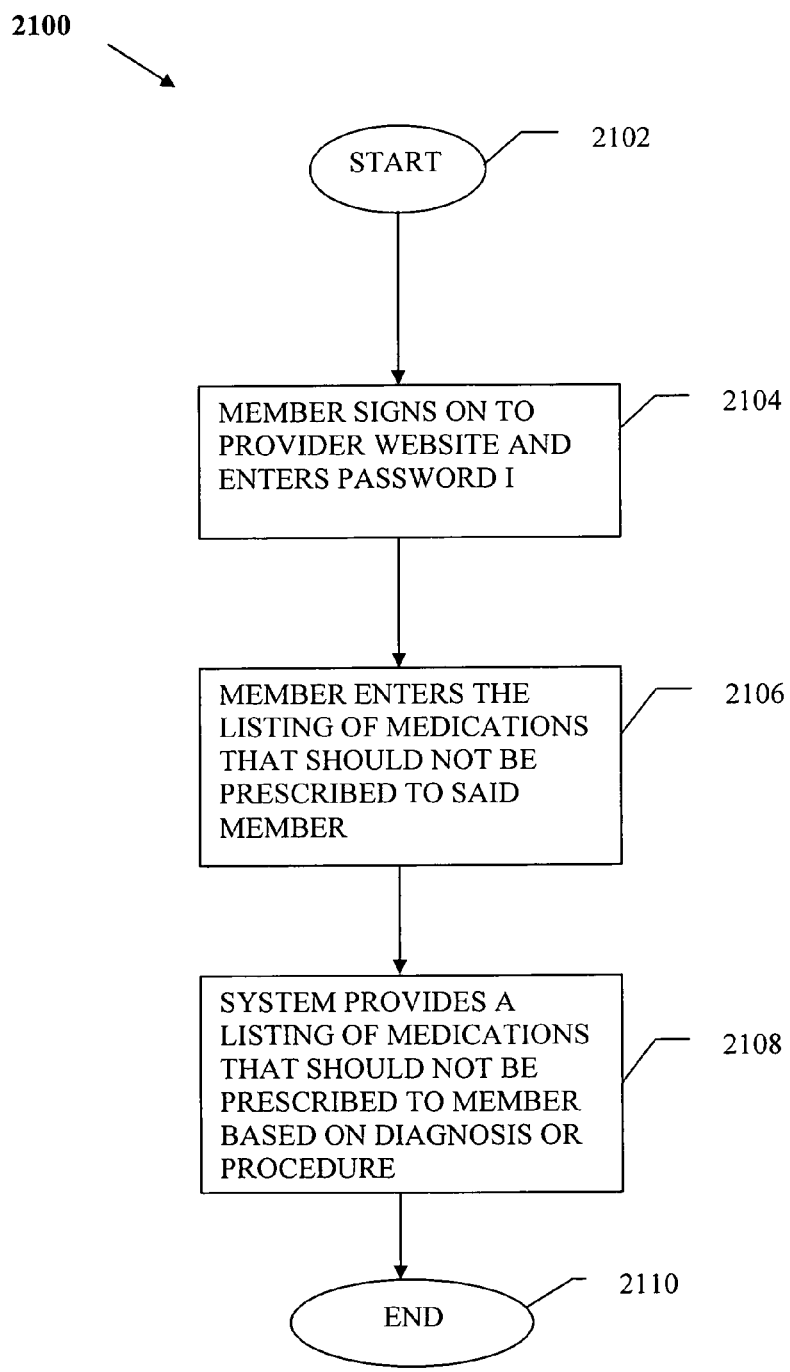
FIG. 21 is a flow diagram that illustrates a member enters the listing of medications that should not be prescribed and the providing a list of medications that should be avoided based on member's medical condition.

FIG. 21 is a flow diagram 2100 that illustrates a method by which a member 102 or any authorized representative enters the listing of medications that should not be prescribed to said member 102. This said listing of medications may include but not limited to trade or generic names, over the counter medications, dose, route, frequency, reason for not prescribing such medications, drug manufacturer, and the like. This restriction of not prescribing certain medication or medications to a member represents an important precautionary steps in preventing a severe drug interaction that may be due to member present health condition, member allergic reaction to certain medication, food or beverage and if not prevented may result in catastrophic injury and in some cases death to the member. For example, if a member has been diagnosed with renal insufficiency, this said member should not be given an "Ibuprofen" or "Advil" because this would results in gastric reaction that may be detrimental to member's health condition. As another example, if a member is having an open heart surgical procedure, the member cannot take any "Aspirin" as this may result in unnecessary bleeding.

After starting in step 2102, in step 2104 the member 102 signs on to provider 104 website and enters password I. In step 2106, member 102 or any authorized representative enters or edits the listing of medications that should not be prescribed or listing of some common food or beverages that should not be given to said member due to member current health condition or recent changes to member's allergic reaction. In step 2108, the MedTrack then provides the member 102 some listing of medications that should be avoided that based on established protocols that have been developed and approved by FDA (Federal Drug Administration) or any other known health group organization that are based on current diagnosis or procedure done and the process is then complete in step 2110.

Figure 22:
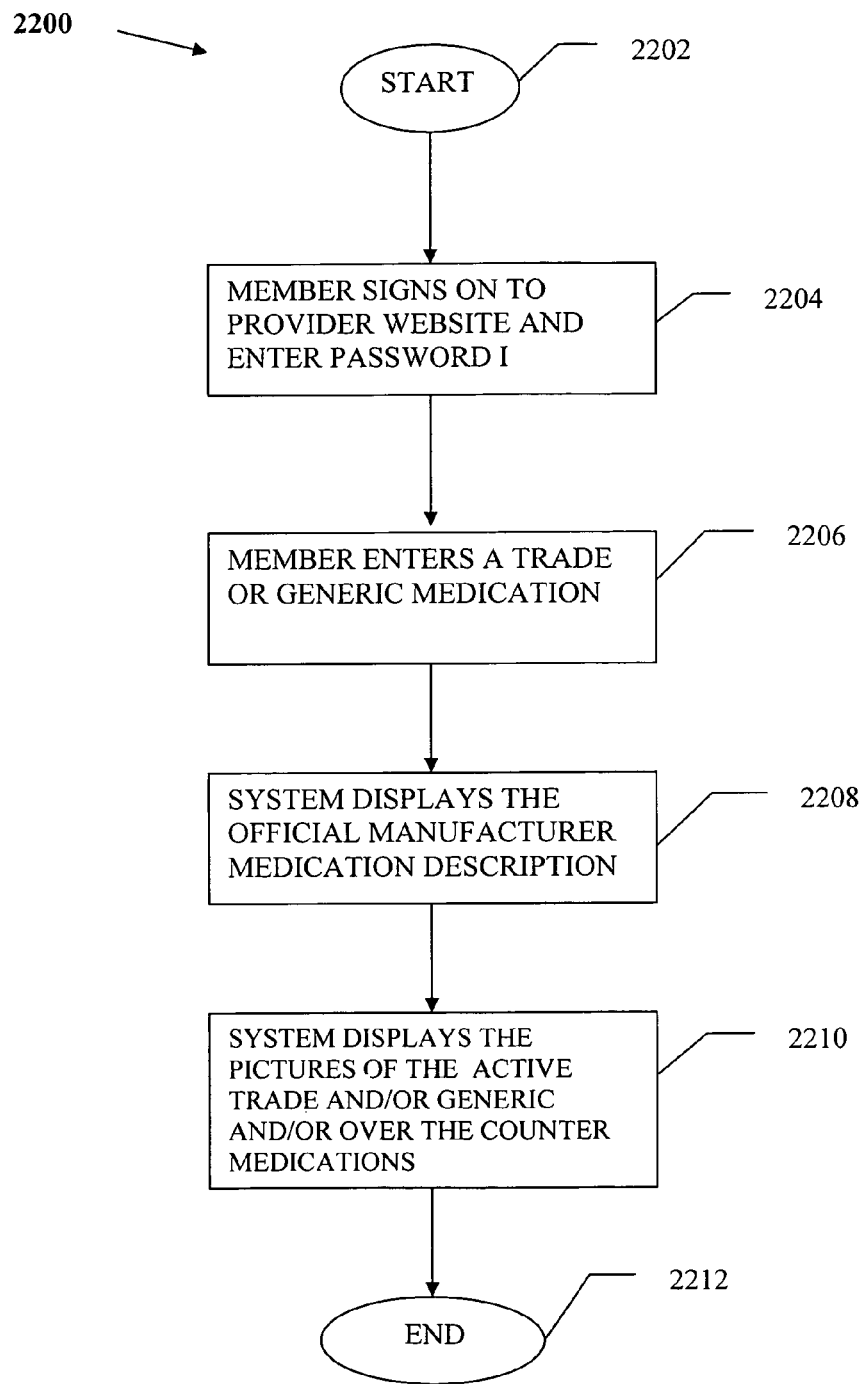
FIG. 22 is a flow diagram that illustrates a process by which the displays or prints the pictures of active medications and the medication manufacturer's description.

FIG. 22 is a flow diagram 2200 that illustrates the process of displaying or printing the official description of the medication as published by the medication manufacturer and also displays or prints the pictures of either trade, generic or over the counter medication. Member 102 may also has the option of displaying or printing all of the active medications that may include trade, generic or over the counter medications. In order to the assist the member 102 in providing them with the most accurate information on the medication or medications that have been prescribed, the MedTrack will not only displays or prints the medication official description but also provide the member 102 the display or picture of either trade or generic version of the medication or both or over the counter medications.

After starting in step 2202, in step 2204 member 102 signs on to provider 104 website using password I. In step 2206, member 102 enters a trade, a generic or over the counter medications. In step 2208, the MedTrack displays or prints the manufacturer's official medication description. In step 2210, the MedTrack displays or prints the picture of the chosen medication that can be either a trade or a generic or over the counter medication and as an option, the MedTrack can display all active medications along with the respective descriptions or pictures associated with each and every medication. This process may provide member 102 additional assurances that the medication that has been prescribed by a physician or any other authorized medical practitioner can be re-verified that they are the true medication that the member needs based on the presented official drug manufacturer's description and the ability of said member to see the actual picture of said medication both in trade or generic or over the counter and the process is then complete in step 2212.

Figure 23:
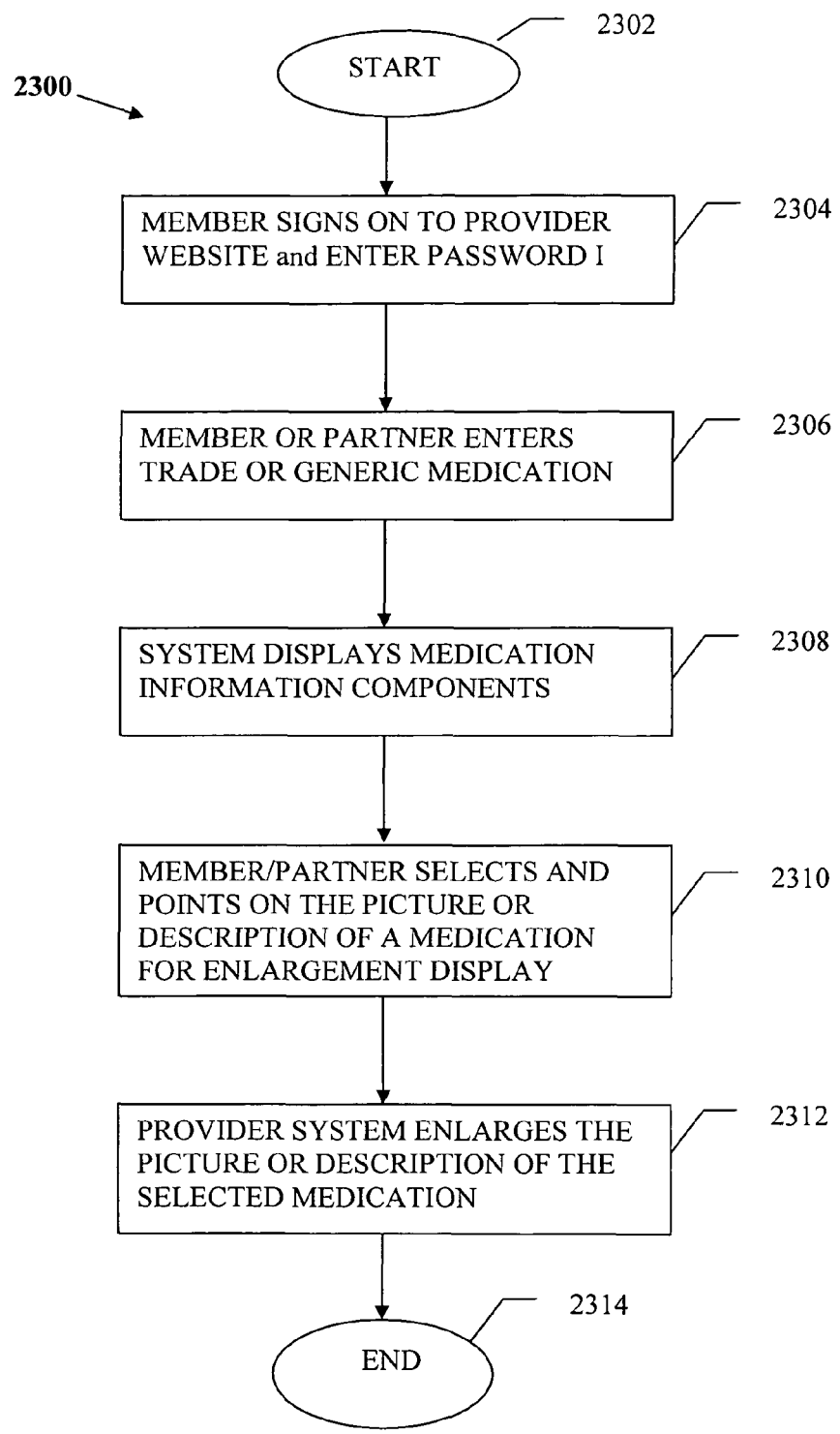
FIG. 23 is a flow diagram that illustrates the process of enlarging the size of the picture, or description of a medication.

FIG. 23 is a flow diagram 2300 that illustrates the process of enlarging the size of the picture or description of a medication. By providing member 102 and partner/associate 106 the capability of enlarging the picture or any of medication information components by pointing or clicking into such selected picture or any medication information components, the MedTrack provides the enlargement of such picture or any description thereby enhancing an easier and clearer understanding or identifying of what the member or partner/associate are actually seeing or reading in assisting them in making a better decision protocol processes. Medication information components may be defined which may include but not limited to the picture of a medication, the drug manufacturer official description of a medication, the listing of medications that the member is currently taking, the listing of medications that should not be prescribed to member, recommendation as to when is the best time to take this medication, the listing of foods that needed to be avoided, the listing of allergies that can be a concern if you take this medication, or the like.

After starting in step 2302, in step 2304 member 102 signs on to provider 104 website using password I. In step 2306, member 102 or physician/partner/associate 106 enters a trade, a generic or over the counter medications. In step 2308, the MedTrack displays the medication information components that may include but not limited to picture of the medication, its official description, the best time to take this medication, the listing of foods that needed to be avoided or the like. In step 2310, the member 102 or physician/partner/associate 106 points the mouse or other pointer mechanism to the picture or desired description of the medication, then in step 2312, the MedTrack enlarges the picture of the chosen medication that can be either a trade or a generic or over the counter medication or any selected medication description and as an option, the MedTrack can display all active medications along with the respective descriptions or pictures associated with each and every medication. This process provides member 102 additional assurances that the medication that has been prescribed by a physician or any other authorized medical practitioner can be re-verified that they are the true medication that the member needs based on the presented official drug manufacturer's description and the ability of said member to see the actual picture of said medication in an enlarged setting for both the trade or generic or over the counter medication and the process is then complete in step 2314.

Figure 24:
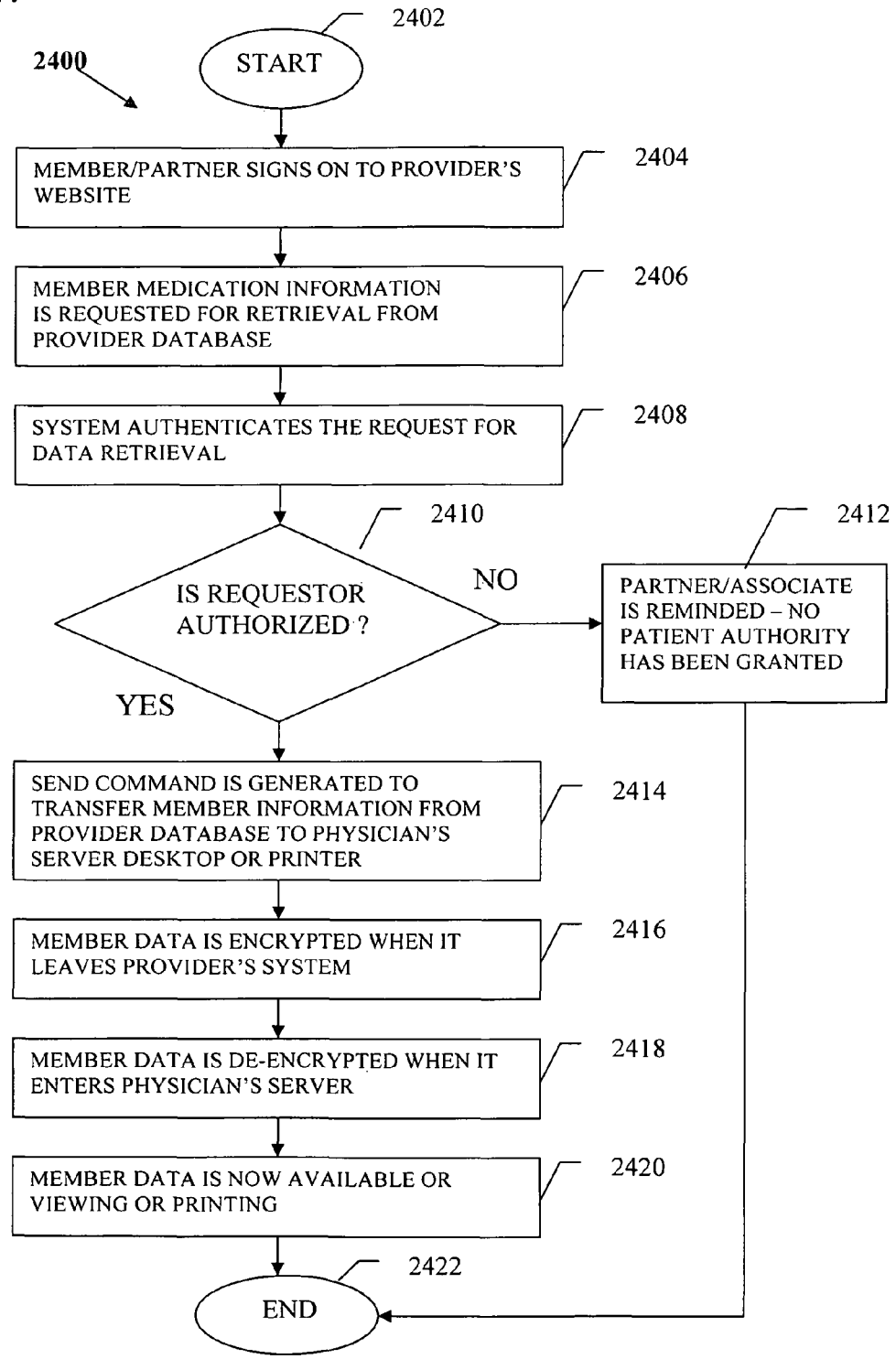
FIG. 24 is a flow diagram that illustrates the encrypted mechanism of data exchanges between the member, physician/associates or provider.

FIG. 24 is a flow diagram 2400 that illustrates the encrypted mechanism of data exchanges between the member 102, physician/partner/associate 106 or provider 104. A member or a physician/associate can also be defined or identified as the requestors. The MedTrack or the in order to protect the integrity and privacy of medical information data of each member 102 against any unauthorized viewing, tampering or the like, the will incorporate the latest innovation of data encryption. The will be adopting the Advance Encryption Standard (AES) or the Data Encryption Standard (DES) with at least the minimum of at least 64-bit block with a 256-bit key and will be meeting also the privacy and security rule requirements mandated by the Health Insurance Portability and Accountability Act (HIPAA) that was enacted by United States Congress in 1996.

After starting in step 2402, in step 2404 member 102 or partner/associate 106 signs on to provider 104 website using password I. In step 2406, member medication information that has been requested for retrieval from provider database by the member or partner/associate is set up by the for delivery to requestor member or partner/associates server, while in step 2408, the authenticates requestor's authorization. In step 2410 a determination is made as to whether the requestor is authorized to view, add or modify member's medication data then if is not, then in step 2412, the partner/associate or any other user is notified that the member has not granted any permission to view, add, modify or print the said member's medication data and the process is then complete in step 2422.

If however, in step 2410, a determination is made that the requestor is authorized to view, add, modify or print member's medication data then in step 2414, the then sends a command to generate the transfer of member's medication information from the 's database to requestor's server desktop or printer. In step 2416, the member's medication data packet is then encrypted when it leaves the provider 's database in order to protect the privacy and integrity of member's medication information components data as mandated by the Health Insurance Portability and Accountability Act (HIPAA) that was enacted by United States Congress in 1996, and while in step 2418, the member's medication data packet is then de-encrypted when it enters the partner/associate's server. The member's medication data is then becomes available for viewing or printing in step 2420, and the process is complete in step 2422.

Figure 25:
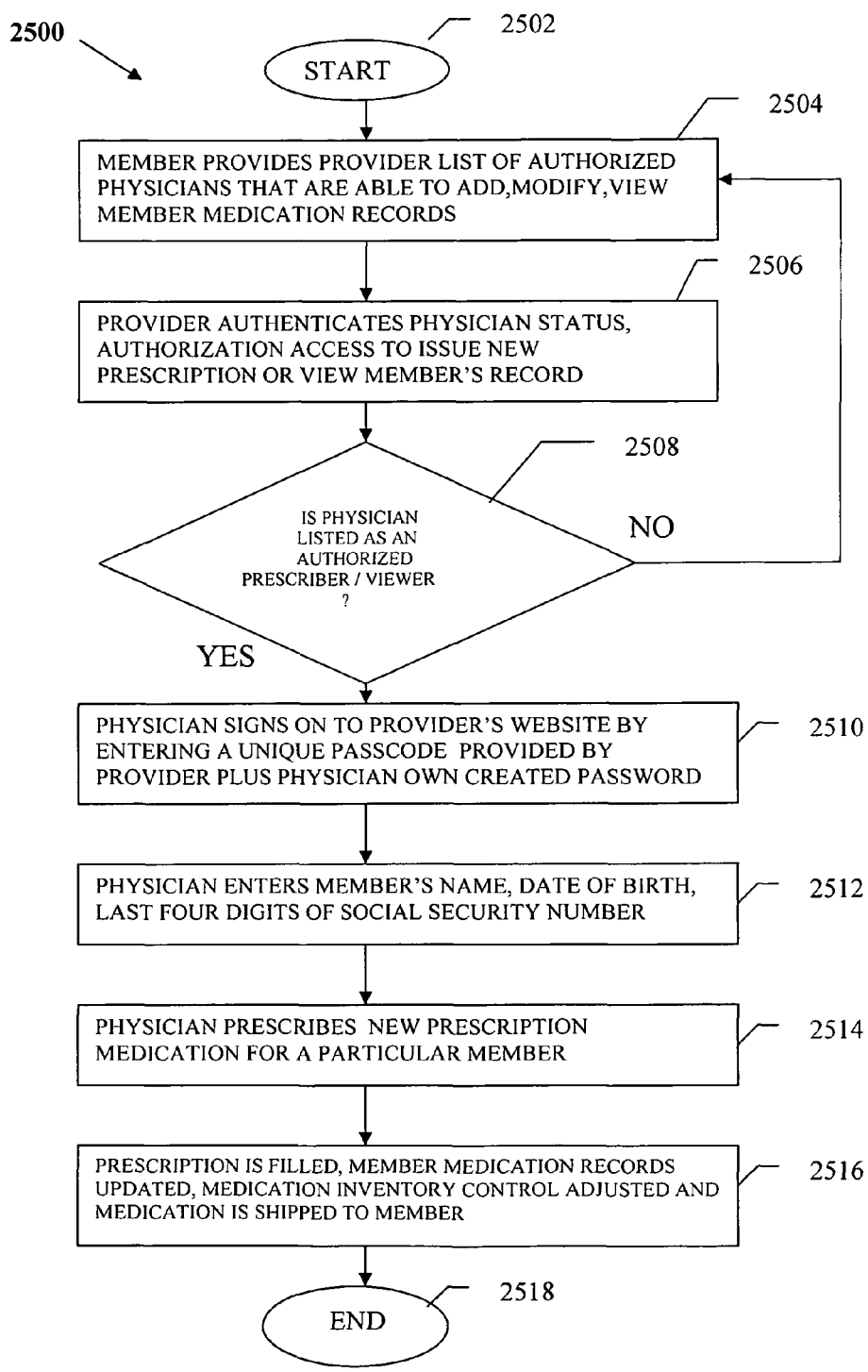
FIG. 25 is a flow diagram that illustrates the electronic medication ordering mechanism for member's physician issuing new medications.

FIG. 25 is a flow diagram 2500 that illustrates the electronic medication ordering mechanism for member's physician issuing new medications for the member. The provider 104 through the establishment of MedTrack or the may insure that the ordering of new medication for the member by any authorized physician could be securely processed by using at least two or more password combinations in addition to having been included in list of authorized new prescription issuer or viewer of the member medication data by the member before a new prescription or refilling of a prescription is done. For example, the adoption of an authentication tokens whereby the server produces a random number that is sent to any authorized physician 106 token's device and then entered this random number plus the chosen password created by individual physician for authentication at the provider 104 server will meet the Health Insurance Portability and Accountability Act (HIPAA) of 1996 requirement to protect the privacy and security of member 102 medication data information.

After starting in step 2502, in step 2504 member 102 provides provider 104 a listing of authorized physician or physicians 106 that may be able to add, modify or view member medication data records. In step 2506, the authenticates physician status as to whether said physician is in the active listing of physicians authorized by the American Medical Association (AMA) before they could prescribe a new or a refill of a prescription or view of member medication records. In step 2508, a determination is made whether the physician is listed as an authorized prescriber or viewer as mandated by the member and by the American Medical Association (AMA) or any of its equivalents, and it is not then the control returns to step 2504.

If however, if in step 2508, after a determination is made that the physician is authorized to prescribe or view member medication records then the process continue in step 2510. In step 2510, the physician then signs on to provider's website by entering the unique authentication token created password provided by the provider which may be in the form of a numeric, alphanumeric or any other combination thereof off of keyboard characters plus the physician's created own password. In step 2512, the physician enters the member's name, date of birth and the last four digits of member's social security number. This process protects the security and privacy of each member medical medication data information from any unauthorized user due to the layers of protection established by the. The layers of protection to the security and privacy of member's medication data fields may be applied but not limited to the prescribing physician, viewing physician or any other authorized user that meets the member's and the 's security authorizations protocol. In step 2514, the physician prescribes the new medication prescription for a particular member after meeting the requirements of having to know the name of the member, the date of birth of the member, the last four digits of the member social security number, being in the list of member authorized physicians and having received a token password from provider 104. In step 2516, the prescription is sent to provider 104 pharmaceutical subsidiary for prescription filling or to any other pharmaceutical organization, member medication record is updated, provider 104 subsidiary medication inventory control is adjusted and medication is shipped to the member and the process is complete in step 2518.

Figure 26:
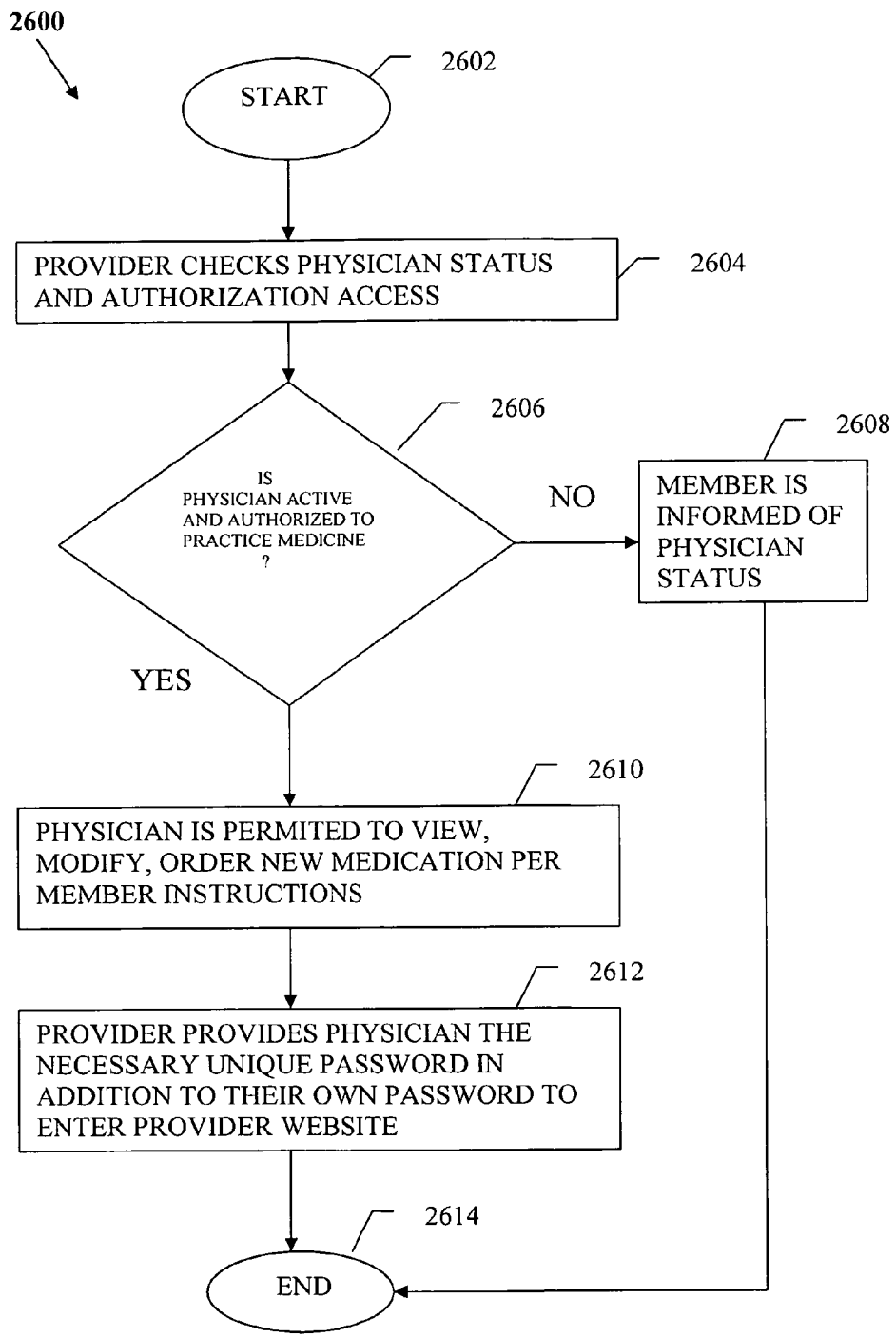
FIG. 26 is a flow diagram that illustrates the process of authenticating physicians status and authorization.

FIG. 26 is a flow diagram 2600 that illustrates the process of authenticating physician status and authorization. The MedTrack in order to assure its member 102 the protection against unauthorized and unneeded issuance of prescriptions or services has instituted a process whereby the physician/partner/associate 106 or any other authorized health care provider or a vendor are checked for their legitimate existence. For example, the physician's education, licensure status may be checked as whether they have the education and authorized currently by the State to practice medicine and making sure that such physician/partner/associate is still living. As another example, the MedTrack will try to prevent billing fraud for equipment purchases for the member, by making sure that the prescribing physician is alive and licensed by the government to practice medicine.

After starting in step 2602, in step 2604 provider 104 checks the physician 106 current status with the American Medical Association (AMA) membership active listing in which said (AMA) has committed to enhancing the quality of care and patient safety by taking lead in the development, testing and maintenance of evidence-based clinical practices. In step 2606, a determination is made whether the physician is active and authorized to practice medicine and if the response is no, then in step 2608 the member is then informed that the physician is not active and therefore not authorized by law to practice medicine and the process is complete in step 2614.

If however, if in step 2606, after a determination is made that the physician is active and authorized to practice medicine by the American Medical Association (AMA) then the process continue on to step 2610, where the physician is permitted to view, add, modify or place an order for a new medication prescription for the member. The provider 104 then in step 2612, provides the physician the necessary unique password that the physician needs to use in conjunction with the password of their own choosing to be able to sign on to provider website and access member medication database information. While the physician is connected with the provider website, the physician or its authorized representative will only be provided with the privilege to view, add, modify or place an order for a new prescription for certain member, if such member has provided the provider an authorization that this particular physician or its authorized representative is authorized to view, add, modify or prescribe a new medication for said member, and then the provider allows the physician or its authorized representative to access, view, add, modify or issue new prescription and only then that the member medication database information becomes accessible to such authorized physician or its authorized representative and the process is complete in step 2614.

Figure 27:
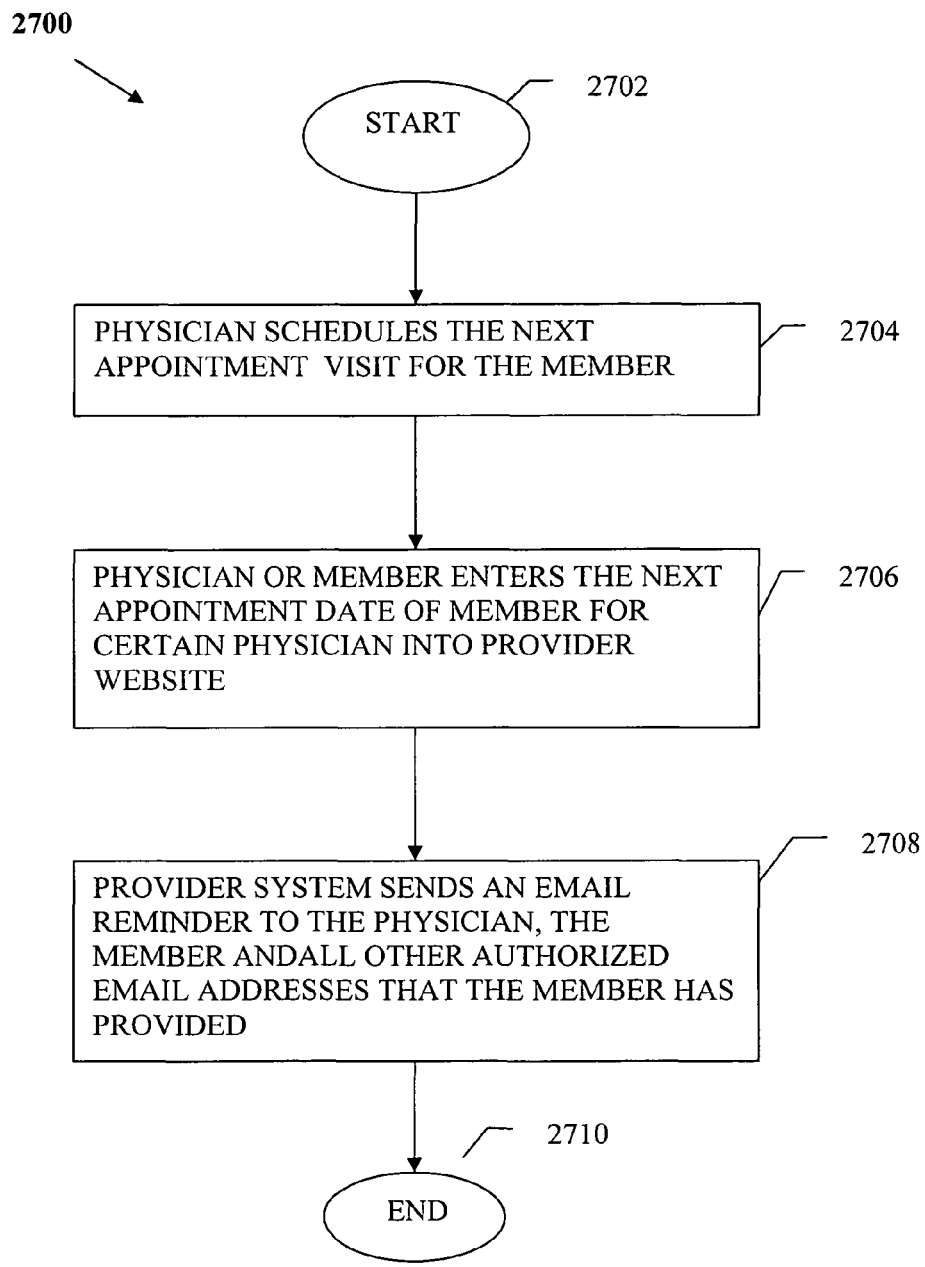
FIG. 27 is a flow diagram that illustrates the process of physician scheduling the next visit of a member that automatically sends an email to the member and to any of the member's authorized representatives.

FIG. 27 is a flow diagram 2700 that illustrates the process of physician/partner/associate 106 scheduling the next doctor visit appointment of member 102 that automatically sends an email to the member and to any of the member's authorized representatives. As a matter of providing an effective communication between the physician and the member, the provider 104 MedTrack provides a method that automatically sends an email notifying the member and its authorized representatives the date and time of the member next medical office visit. These upcoming office visit or visits in most cases are critical for the health and welfare of the member especially for those follow-up visits where the physician needs to know the results if a new prescription was prescribed, any allergic reactions or drug interactions if two or more medications are being taken within twenty-four hours period and to see if the new medication is working as intended or if a change in medication is warranted.

After starting in step 2702, in step 2704 the physician/partner/associate 106 schedules the next medical office visit of the member 102. One of the ways of implementing this process would be by electronically entering the future appointment date of the medical visit of the member into the provider 104 website. Another way would be the physician writing the next appointment date on a piece of paper and delivering such piece of paper to the member or to any of the member's authorized representatives then entering the next appointment date and time into provider 104 member's database.

In step 2706, the physician or the physician's authorized representative or the member or the member's authorized representative signs on to provider website using their respective password I as shown in one of previous embodiments and enters the member's future medical appointment date and time. In step 2708, the MedTrack or the sends a reminder email to the member, the physician's office of the physician who has scheduled the member and to all other authorized email addresses that the member has provided. For example, by using a triggering mechanism of identifying the future appointment date, the MedTrack would after sensing that a future date has been entered, the then uses this information of said future date to trigger the sending of automatic emails to the physician issuing the next future medical office visit, to the member who will be visiting the said next medical office visit and to all other active authorized representatives that the member has listed and are active in the provider database, and the process is complete in step 2710.

Figure 28:
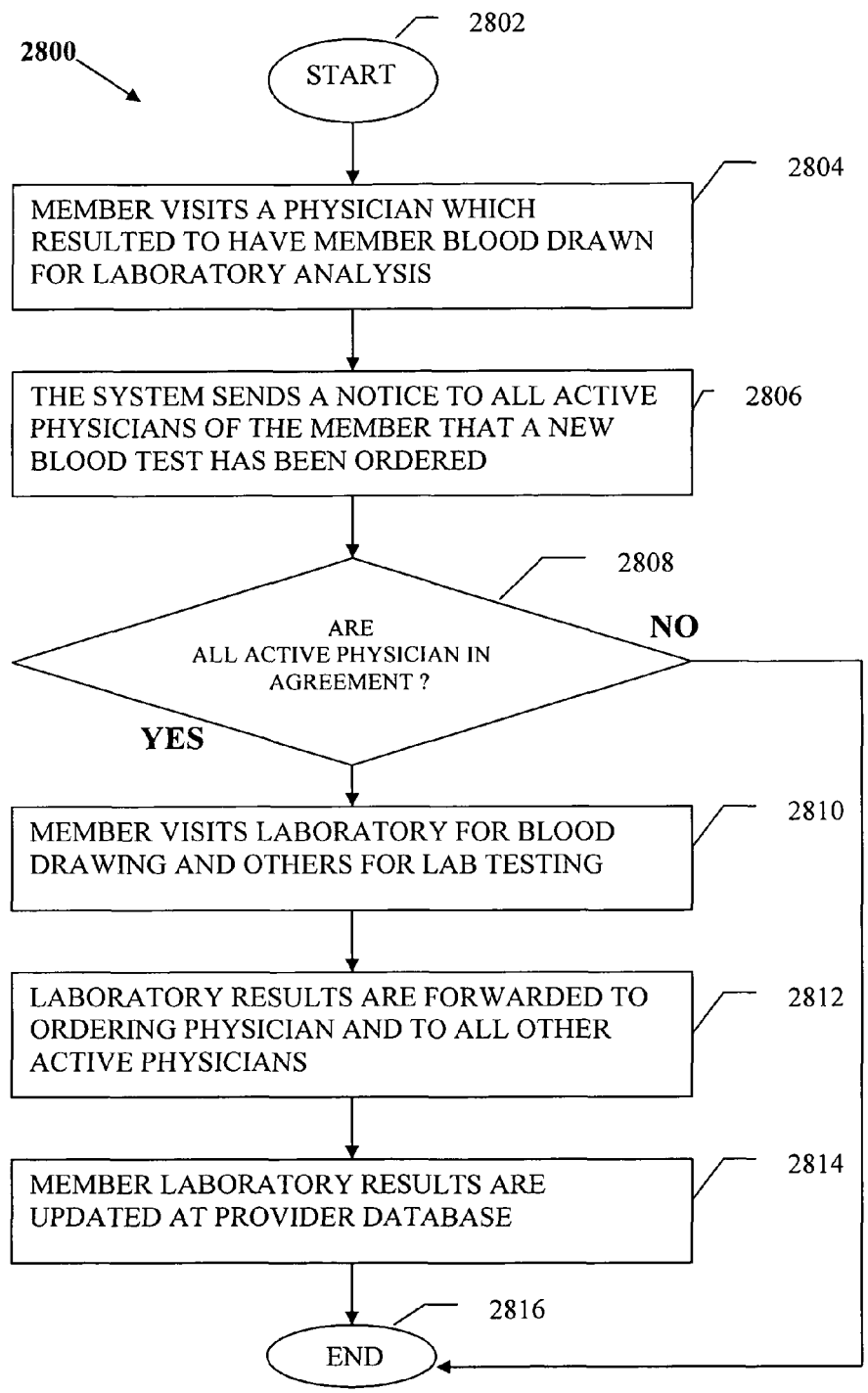
FIG. 28 is a flow diagram that depicts a feature for automatically sending an email to other active physicians of the member if a new laboratory tests are ordered.

FIG. 28 is a flow diagram 2800 that illustrates the process in which member 102 ordering of laboratory tests by physician 106 is properly managed. Laboratory tests include but not limited to blood, urine, stool or some other tests. With the lacking of active physicians communicating with one another in relation to the current treatment plans for the member that may include but not limited to laboratory testing, a need for complete coordination and communication must be established among the active physicians to protect the health and well being of the member.

For example, there has been established documented evidence to support that a member or patient encountered unnecessary blood drawing if, for instance physician 1 who previously ordered a serum, lipids, urinalysis or other tests does not inform the other active physicians of said member or patient of such laboratory tests that had been done recently or the other active physician or physician 2 needing the same or some of the test results that may have been done previously through the ordered test placed by physician 1, and the intervals would have been good enough to meet the need of physician 2 had been communicated among the active physicians that such test results has been in existence, then an unnecessary blood drawing and testing would have been eliminated, thus saving member or patient laboratory costs and pain and suffering at the same time. As another example, in a case where the member may be having a kidney failure, blood drawing should be limited to certain intervals by giving the patient or member's blood supply to recover at a safe level before another blood drawing could be done safely. This effective process applies if there are two or more active physicians that are currently treating the same member.

For reporting purposes, the MedTrack will display or print the laboratory results of a member either to a computer screen that the member or physician uses or print them directly to a printer. For example, the report can be presented as follows:

| Date of Test | Cholesterol | HDL | TRIG | PSA | ALT | AST | RBG |
|---|---|---|---|---|---|---|---|
| Aug. 01, 2008 | 200 | 34 | 101 | 1.16 | 30 | 24 | 108 |
| Jul. 25, 2008 | 243 | 37 | 89 | 1.10 | 29 | 23 | 106 |

The sample report above sorted descending order by date of test, by respective laboratory tests, by laboratory test results, presents an easy to read, easy to understand reporting mechanism for which the physicians could easily make a logical decision as to next appropriate step or steps for the member treatment protocols. The sorting or selecting of tests may include without limitation to date of test or type of test that a member may be required to undertake.

After starting in step 2802, in step 2804 the member 102 visits a physician 106 which resulted in having the member blood drawn for laboratory analyses, the results of which will be needed in the determining the best diagnosis of the member before an appropriate and effective treatments plans or goals are placed in order by the physician. In step 2806, the MedTrack sends an email notice to all active physicians informing them that a new blood test for the member has been ordered. In this situation, for example, an opportunity for the MedTrack to prevent an unnecessary blood drawing and testing especially if the member blood supply is becoming scarcer due to medical condition by sending the most recent laboratory test results via email to all other active physicians of the member and, if the said laboratory test results are within the time frame of any of the other active physicians need then an unnecessary blood drawing or other laboratory tests could have been prevented thus saving the member cost and unneeded pain and suffering. In step 2808, a determination is made whether all the active physicians are in agreement that a new laboratory testing for the member is needed, if they are not, then the active physician needing laboratory test results uses the most recent laboratory results posted to provider 104 member 102 medication database or use the most recent laboratory results that were emailed to all active physicians by the MedTrack and the process is complete in step 2816. If, however, in step 2808, a determination is made that all active physicians are in agreement that a new laboratory testing for the member is needed, then control goes to step 2810, where the member visits the laboratory for blood drawing or other laboratory testing. After the laboratory results become available, in step 2812 the results are forwarded to the ordering physician 106 and to all other active physicians. The member 102 laboratory results fields are updated and the laboratory reports are formatted in the provider 104 database of MedTrack and the process is then complete in step 2816.

Figure 29:
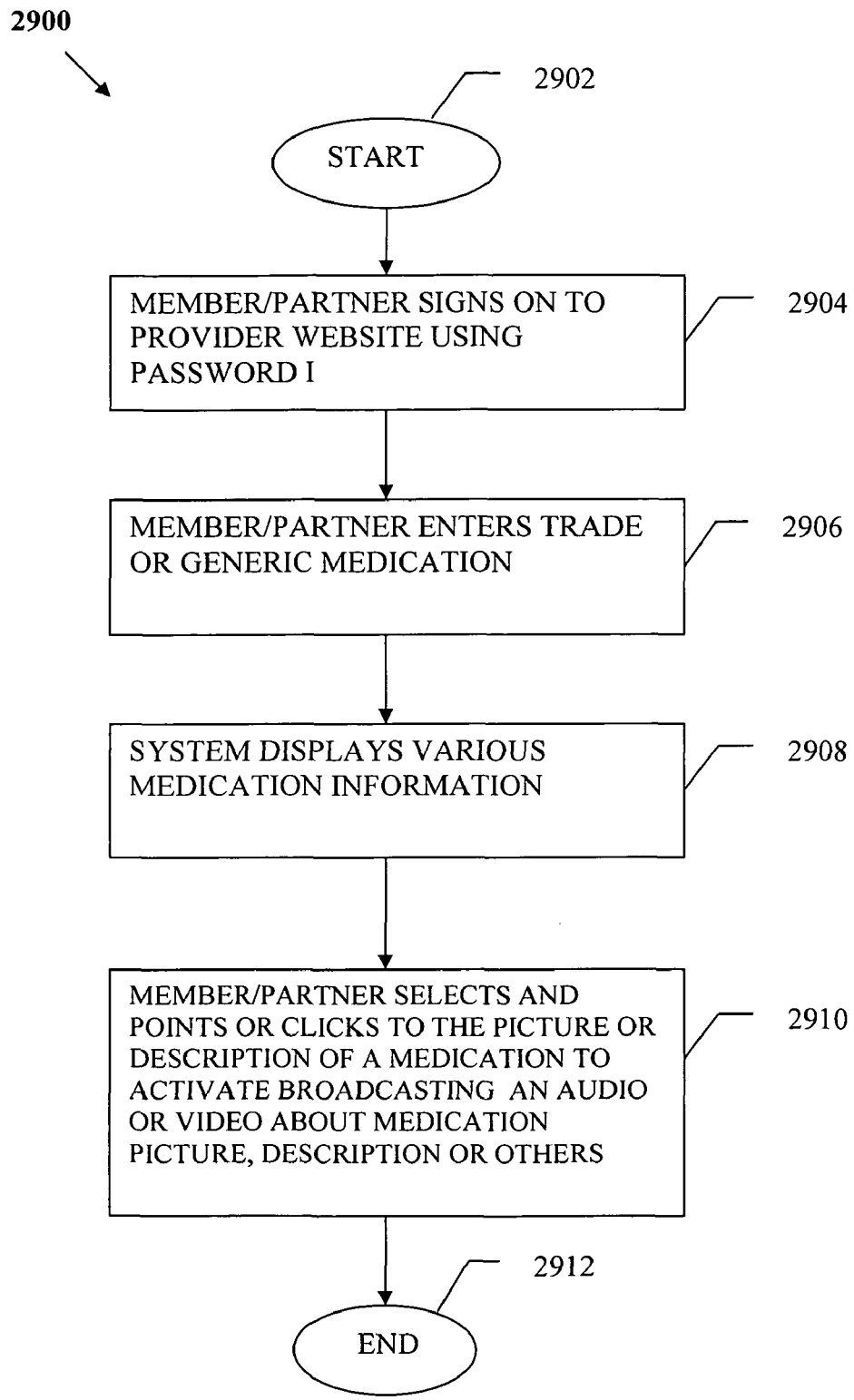
FIG. 29 is a flow diagram that illustrates the process by which the provides the audio or video option of broadcasting the medication information components.

FIG. 29 is a flow diagram 2900 in accordance with an embodiment that illustrates the process in which member 102 or partner/associate/physician 106 is provided with the additional capability of not only viewing the picture, but also enlarging such picture, viewing the description or enlarging such description or the like of a medication, or the medication information components which may include but not limited to the listing of member medications that are currently being taking from home, the listing of medication that should not be prescribed to said member, listing of allergies, listing of foods to avoid while taking this medication, the best time to take this medication, the official description of said medication or the like but also is provided with an audio or video capabilities for the member or partner/associate/physician to listen or view the video of the medication information components as previously mentioned or the like. The addition of audio and video capabilities of the MedTrack provides the member or physician an additional flexibility in delivering the medication information components in many ways aside from the mere reading of the medication information components as presented to them.

After starting in step 2902, in step 2904 the member 102 or physician/partner/associate 106 signs on to provider 104 website using password I. In step 2906, the member or physician/partner/associate or any other authorized user enters a trade or generic medication in which the MedTrack displays various medication information components as shown in step 2908. Medication information components may be defined to include but not limited to the listing of medication from home, the listing of medications that should not be prescribed to the member, listing of allergies, the picture of a medication, official description of a medication, laboratory results presented in an easy display comparative format, the best time to take a medication, listing of foods that needed to be avoided while taking such medication or the like. In step 2910, the member or physician/partner/associate selects and points the cursor or any other type of pointer to a particular medication picture or description and the MedTrack activates the audio or video mechanism that broadcast the information about the picture or description of the medication or any descriptive medication information components that may relate to a medication. For example, the member or physician/partner/associate or any other authorized user may listen to the broadcasting of medication's picture or watch the video that may describe or show the color, shape or manufacturer of said medication that may emanate from the user's computer speakers or computer monitor for the video or any other broadcasting devices that may be hardwired or wireless connected to said user computer or any other compatible media devices and the process is then complete in step 2912.

New Material

Figure 30:
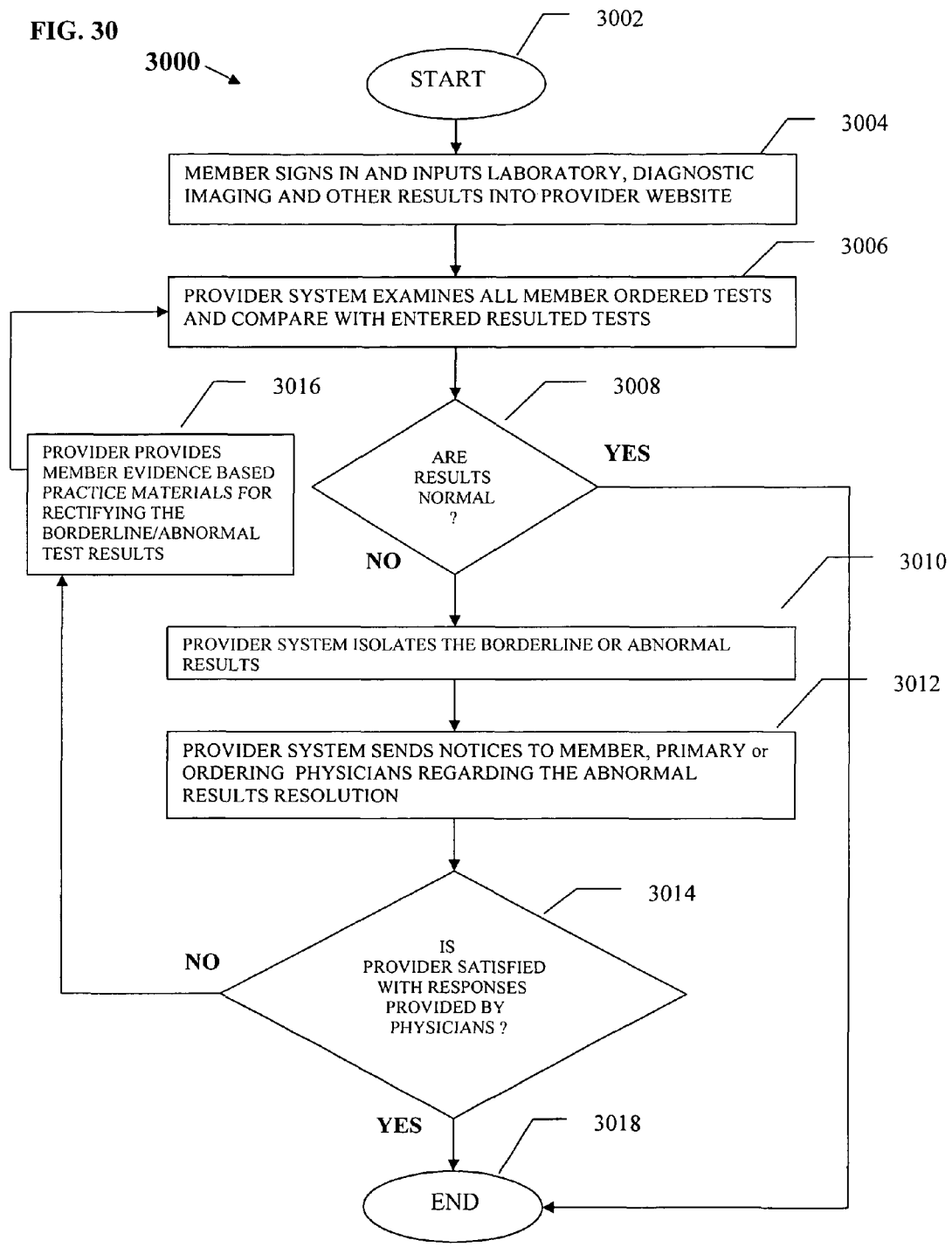
FIG. 30 is the flow diagram that illustrates the process of following up any abnormal test results that have been submitted by the members to provider.

FIG. 30 is a flow diagram 3000 in accordance with an embodiment that illustrates the process in which member 102 test results are analyzed by provider 104 MedTrackSystem and isolate the abnormal test results that may include but not limited to laboratory, diagnostic imaging and other test results so provided by member 102. Abnormal test results may be defined as any medical test results that are too low or too high and do not fall within an established and accepted ranges of numbers for a certain particular test result. For example, a cholesterol test has a normal range of 160-240 mg/dL. Any test results that are below 50 or over 240 mg/dL need physician attention especially, if the result is way over 240 mg/dL. Clinical studies have shown that having high cholesterol level raises the risk of heart diseases that can lead to heart attacks. As another example, (HealthDay News) has reported that people who visit their primary care physician for routine blood tests or screenings are often not informed of the results, a new study finds. The failure of doctors and medical facilities to follow-up and give people test results is "relatively common" even when the results are abnormal and potentially troublesome, and affects one of every fourteen tests.

In order to prevent this problem in happening, the MedTrack or MedTrackSystem not only exposes these abnormal results but also provides follow-up reminders to the member 102, their authorized representative, their primary physicians, ordering physicians and any other physicians through an open communication that may be via interne, telephone, personal visits, electronic monitoring system, faxing, any wireless appliances or any other types of communication devices or methods to making sure that member 102 and provider 104 are communicating openly are well established and implemented so as to assist the member in converting the abnormal results back to normal test results. As another example, provider 104 may suggest some life changing eating habits for the member 102 like eating more fruits and vegetables and eating less red meats, add exercise as part of a member's daily or weekly regimens would most likely helps in lowering said member cholesterol level naturally, meaning getting better without medicinal interventions. If, after trying the eating and exercise regimens for some time and after having taken another cholesterol blood test and the said cholesterol level is still elevated beyond normal, then the next logical step would be to take medication like "Lipitor" or any equivalent medication to stabilize the cholesterol level. Provider 104 will continually be sending reminders to member 102 and its authorized representative, primary or ordering physicians and will only stop sending these said reminders only and only after member 102 cholesterol test results reading turns back to its normal range.

After starting in step 3002, in step 3004 the member 102 signs on to provider 104 website using password I to enter any laboratory, diagnostic imaging or any other test results into provider 104 website which can be entered by the member 102, physician/partner/associate 106 or any other authorized users. Entries to provider 104 website could also be done through electronic transfers from any laboratory, diagnostic imaging or other sites in addition to manual entries. In step 3006, provider MedTrackSystem examines all member 102 ordered laboratory, diagnostic or other tests and compared them with that of tests resulted that have been entered into provider 104 database for same said member. Discrepancies between ordered and resulted tests are then reconciled by the MedTrackSystem. In step 3008, a determination is made whether a result submitted by the member is normal. If the result is normal, then the process is complete in step 3018. If however, in step 3008, after a determination is made that the resulted test submitted by said member is borderline or abnormal, then the control transfers to step 3010 where the MedTrackSystem isolates the borderline or abnormal result, then the process continues on to step 3012 where provider 104 sends notices to member 102 or its authorized representative, primary or ordering physicians regarding the said member resulted borderline or abnormal test result that has been forwarded to provider 104. At this juncture, provider 104 will not only will be sending the notice of borderline or abnormal results but also will be sending to said member recommendations as to the processes that could be done with the objective of turning any borderline or abnormal results back into normal result. The method of communication by provider 104 to the member 102 or its authorized representative, primary or ordering physicians may include but not limited to email, U.S.A. postal service, wireless telephone, land line telephone, personal courier service, commercial courier service, personal visit by provider 104 representative to member's residence or the like. For example, a member who had just been told that he or she may had converted into becoming a diabetic because of blood test RBG reading of 150 with normal ranges between 65-110 needs to have additional test to confirm of such a conversion. In accordance to an embodiment, the MedTrackSystem would recommend to member 102 that further test be done to make sure that the current prognosis is correct which may include but not limited to the following other tests: (1) Hemoglobin A1c blood test which will tell the member and the doctor how well diabetes is managed over time. It measures the member average blood sugar in the previous three months to see if it has stayed within a target range and should have a value below 7%; (2) Dilated Eye Exam—if the member has diabetes, the member ophthalmologist or optometrist should perform a dilated eye exam, in which the pupils are widened with drops, to check for signs of diabetic retinopathy. With diabetes, high blood sugar damages tiny blood vessels in the retina, the light-sensitive tissue at the back of the eye. Without treatment, these new vessels can bleed, blur vision, severely damage the retina, and lead to vision impairment or blindness; and (3) Foot Exam—Diabetes can cause nerve damage and numbness, as well as decreased circulation that makes it harder for the body to fight infection. Patients with numbness problems may not notice if they injure a foot. A resulting infection may not heal well, and skin and other tissue may die. In a small minority of cases, the problem progresses into a complication that requires amputation. In these examples, combinations of two or more positive results help confirm that the member is now a diabetic. In step 3014, a determination is made as to whether the response from the member 102 physician is satisfactory to provider 104 expectations and if it is then the process is complete in step 3018. If, in step 3014, after a determination is made that the physician response does not satisfied provider 104 expectations, then the process continues to step 3016 where provider 104 provides the member 102 a series of steps that are outlined based on evidence based practices in rectifying such member borderline/abnormal test results. Evidence based practices can be built in a library that can be sub-divided under different disease treatments or prevention topics ranging from a simple ailment to a more complicated diseases. Provider 104 may also provide protocols for selecting the most acceptable treatment or treatments from a group of interventions intended to treat the same problems. To be designated as "best practice", a treatment would need to have a sound theoretical base, general acceptance in clinical practice, and considerable anecdotal or clinical literature publications. Provider 104 expectation is defined as a series of processes or steps that are adopted for the purpose of turning borderline or abnormal test results into within the normal ranges of numbers that are defined by and based upon the scientific studies performed by experts on their respective fields of expertise. The process may involve series of steps and follow-ups that MedTrackSystem has designed for the purpose of reversing the borderline or abnormal test results into normal result of said member. As further example, as in a diabetic case, the first step would be for the member 102 to fill out a lifestyle survey that will help determine the most appropriate evidence based treatments that can be used in the reversal of said borderline or abnormal results of said member. MedTrackSystem will look into the member 102 height and weight (determines whether the member is obese or not), exercises routines adopted if any, types of food being ingested (meat, fruit, vegetables, type of breads), consumption of alcoholic beverages or the like. From this member surveyed data, MedTrackSystem provides a list of evidence based treatment or treatments to member 102 that may include suggestions that member could start eating more fruits, vegetables, whole wheat bread instead regular enriched bread, avoid drinking sodas or alcoholic beverages, drinking green tea instead, adopt exercise regimens daily or weekly and be re-tested again to see if any improvement in test results have occurred, then the process goes back up to step 3006, where provider 104 MedTrackSystem re-examines the test results again then the control moves down to step 3008 again until the processes finally ends in step 3018.

FIG. 31 is a flow diagram 3100 in accordance with an embodiment that illustrates the process by which member 102 is provided the complete control of viewing, printing or downloading all of the users who have viewed, printed, downloaded said member medical records off of provider 104 website via an icon off of any computer screen in which said member can click at any time to view, print or download the listing of said users who have viewed, printed or downloaded said member medical records information. Member medical record may be defined as a comprehensive lifetime medical record of a person that may include but not limited to allergies, diagnoses, procedures, visits history, diseases, medications, treatments, progress notes, consultations or the like. In order to simplify the identify of the users who viewed member 102 medical records history, easily, provider 104 for example assigns user's ID can be any one of the options as follows: (1) for employees of provider 104 the first letter of user ID may start with "*" followed by at least five alphabetic characters; (2) for partners/associates 106 the first letter of user ID may start with "@" followed by at least five alphabetic characters or can be created using any other type of alphabetic or alphanumeric combinations. This feature of the invention will not only makes it easier for both member 102 and provider 104 to clearly identify the users who are authorized and the users who are not authorized to view, print or download member 102 medical records information data, but also meets the requirements of HIPAA act of 1996 in regards to "Security Standards for the Protection of Electronic Protected Health Information" section of the act. To further assure the complete security of member 102 medical information, provider 104 will provide the member an audit trail for every changes made to every field of member medical history records in the system may include but not limited to user, date and time when said changes occurred, which part of member 102 records have been viewed, printed or downloaded or the like.

After starting in step 3102, in step 3104 the member 102 signs on to provider 104 website using password I. In step 3106 provider 104 provides an icon on an opened member 102 computer screen where a member can click that said icon at any time to view, print or download the listing of all users who have viewed, printed or downloaded his or her medical records information. The listing of users provided by MedTrackSystem in step 3108 may include but not limited to date and time when the viewing, printing or downloading occurred, the portion or portions of the member medical records that were viewed, printed or downloaded, the name, address and location of the computer that was used in viewing, printing or downloading said portion or portions of the member medical records or the like. In continuing the process, in step 3110 a determination is made as to whether the listing of users provided by MedTrackSystem who viewed, printed or downloaded member medical records data have all been authorized by the member 102 prior to said viewing, printing or downloading, and if said listing of users are authorized by the member then the process is complete in step 3114. If not, then the control returns to step 3112 wherein the provider 104 checks the member 102 authorization listing and compare that with said authorized listing that were provided by said member with that of the list of users who viewed, printed or downloaded said member medical record data. In situations where the users who have viewed, printed or downloaded the medical records data of a member are not authorized to view, print or download said medical records of a member, then provider 104 is mandated by HIPAA to report such violation to the member within 10 business days after learning about the breach, depending on the sensitivity of the data. However, if provider 104 believes that the unauthorized access may have been the result of a crime, this notification obligation may be delayed if a law enforcement agency first determines notification will impede a criminal investigation. In addition, provider 104 will investigate why the unauthorized users were able to penetrate the security parameters setup to protect member medical records data and then make the necessary changes to correct the weaknesses of the process, re-test the security system and then activate the new and improved secured system. Provider 104 then sends member 102 a complete report as to why the violations occurred and assuring said member that the provider website has now been fully secured, then the process is complete in step 3114.

FIG. 32 is a flow diagram 3200 in accordance with an embodiment that illustrates the process by which provider 104 MedTrackSystem identifies the member 102 medical condition. Medical condition may be defined as any illness, injury or disease that has been determined by any license physician through recorded diagnostic testing processes that may include but not limited to observation, answers to questions asked by a doctor and/or the resulted tests done that have been verified. For example, illness may include but not limited to diabetes, fever, depression, anorexia or the like, disease may include but not limited to forms of cancer, heart disease or the like, and injury may include but not limited to bruises, wounds, burns, fractures or the like. Because one of the objectives of this invention is to reduce the overall cost of health care, provider MedTrackSystem will provide a library of health care preventive and wellness programs to members 102. These so called health care preventive programs are specifically designed based on evidence based practices that have been developed and implemented that relates to certain specific illnesses and/or injuries. Wellness programs may include but not limited to different exercise programs, providing new discovered drug efficacy like, people who has been taking cholesterol-lowering statin drugs who develop pneumonia are less likely to die from it than those not on statin, people who eat the most red meat (averaging at least 5 ounces a day) are about one-third more likely to die prematurely than those eating little or no meat, that ounce for ounce, kiwifruit has more vitamin C than an orange and more potassium than a banana or the like. The process of communicating these health care materials by provider 104 to member 102 may be done via internet, telephone, personal visits, electronic monitoring system, faxing, any wireless appliances or any other types of communication devices or methods.

For example, a member who is overweight and has blood glucose, also called blood sugar, levels higher than normal but not high enough for a diagnosis of diabetes—a condition called pre-diabetes will be provided with preventive health care materials containing information like losing a modest amount of weight through dietary changes and increased physical activity sharply reduced their chances of developing diabetes. By eating less fat and fewer calories and exercising for a total of about 150 minutes a week, is estimated to lose about 7 percent of their body weight and maintain that loss which may reduce the chances of developing diabetes. The other option would be to check with the member 102 primary physician to see if the member can take 850 mg of metformin twice a day also adds in reducing risk of developing diabetes. Diabetes is the main cause of kidney failure, limb amputation, and new-onset blindness in American adults. People with diabetes are more likely than people without diabetes to develop and die from diseases of the heart and blood vessels, called cardiovascular disease. Adults with diabetes have heart disease death rates about two to four times higher than adults without diabetes, and the risk for stroke is two to four times higher among people with diabetes. As previously described, the preventive features of the invention puts emphasis on helping the members 102 who are on pre-diabetes stage not to develop that said disease into a full blown diabetes by providing them supports and assistance and directing them to a healthy life styles. Health care cost can be then be controlled by avoiding unnecessary physician's fees, possible hospitalization, pharmaceutical, laboratory, other ancillary costs and/or lost wages of the member or immediate family member.

After starting in step 3202, in step 3204 the provider 104 MedTrackSystem identifies the medical condition of member 102. In step 3206, after provider 104 has determined and analyzed the medical condition of member 102, provider 104 provides the necessary preventive programs, home health services, wellness programs, rehab programs, remote electronic medical monitoring system or the like that will support member 102 medical condition. For example, in a home heath services, skilled nursing services like patient education, family instruction, medication supervision, nutritional counseling, heart and blood pressure monitoring or the like may be provided member 102. As another example, in a cardiac rehabilitation under rehab program, provider 104 may provide a medically supervised program to help heart patients recover quickly and improve their overall physical, mental and social functioning. The goal is to stabilize, slowed or even reversed the progression of cardiovascular disease, thereby reducing the risk of heart disease, another cardiac event or death. Cardiac rehabilitation program may include but not limited to counseling so the patient can understand and manage the disease process, beginning an exercise program, appropriate use of prescribed medications or the like. As another example, provider 104 may offer a remote patient monitoring system which may be wireless, wired connected, via interne or the like to member 102 whereby the potential of not only reducing the cost of caring for members but also having the ability to measure member's physiologic progress and responses, and to communicate with the members the importance of behavior or diet changes in which real-time monitoring is implemented. Then in step 3208, provider 104 charts and records the progress of member 102 medical condition and makes continued follow-up if needed, then in step 3210 provider 104 provides progress reports of member 102 medical condition to the primary-ordering physician or any authorized representative of member 102. In step 3212, a determination is made as to whether the feedbacks from physicians regarding the medical condition of member 102 are favorable and if they are then the process continue in step 3214, where provider 104 establishes a follow-up schedules for the purpose of contacting member 102 on a periodic basis, to making sure that when the state or period during which the member symptoms of their disease is continuously abated is established. For example, provider 104 can check whether the established healthy eating habits, exercises that were put into placed, following-up the schedule of taking prescribed medications are done accordingly or the like, then the process is complete in step 3216. If however, in step 3212, after a determination is made that the physician feedbacks are not favorable, then the control returns back to step 3206, wherein the provider 104 programs are reviewed, make the necessary adjustments to the programs in which member 102 is currently participating in, then in step 3208, provider 104 continues to record the progress notes of member 102, and followed by step 3210, wherein provider 104 continues to report the progress of member medical condition to member 102 or the authorized representative, responsible physicians (primary or ordering physician) until provider 104 becomes satisfied with the favorable feedbacks from the responsible physicians in step 3212, then a follow up in step 3214, is scheduled to contact member 102 on a periodic basis for the purpose of monitoring said member medical condition and then the process is complete in step 3216.

The novel approached described herein for the members to be able to enter the list of their medications that are currently being taken from home or listing of medications that should not be prescribed to them and having the options of adding, modifying, retrieving, enlarging, listening, watching, transferring or printing such medications listing or other related medication information stored at Level I database provides several advantages over remembering such medication information from memory. Likewise, members are provided an alert system through a secondary storage Level II database in which other personal information can be stored safely, that may include but not limited to telephone numbers, birthdates, anniversary dates, addresses, secret recipes or the like, and only accessible by members through the activation of a secondary password. Partners like physicians would have the capability of updating members medication listings by either entering the new medications directly to provider's website, or sending the list of said medications to the provider via various delivery channels as previously described herein, in which provider updates members medication listing or the member signing on to provider website and update their respective medications listing. For example, if a member enters a hospital, it is now mandatory for a prospective patient to provide a list of current medications that said patient are taking from home.

More specifically, an attending physician needs to know the medications a patient are currently taking from home before prescribing a new one to make sure that there would be no medication interactions among the medications the patient are currently taking with that of the new ones that are about to be prescribed. Medication interactions which are sometimes referred to as "adverse drug events" have been documented to have resulted in some cases contributed into worsening of the patient conditions and in some events have resulted in patient death.

Furthermore, the subscribing members are afforded with purchase discounts for medication purchases from any partner/associates or from provider's wholly owned subsidiaries which can be located either in the U.S.A. or any place in the world. This said purchase discounts may also apply to any other commercial products or professional services that may be available from time to time at any participating partner/associates or wholly owned subsidiaries. Membership fees may be waived on some members who have met the minimum dollar volume requirements within a membership period.

In the forgoing specification, the invention has given the members the ability to enter, add, modify, activate, deactivate medications and print such home medication listing, the listing of medications that should not be prescribed, can authorize physicians, other authorized medical professionals or any other authorized users to view, print the listing of medications being taken from home, print or view the laboratory test results of the member in an easy to read and understandable format, to view or print the listing of medications that should not be prescribed to a member or the like. The provider may sell to member any commercial products that may include but not limited to prescription medications, pharmaceutical supplies, over the counter medications, medical equipment and supplies or the like at wholesale prices plus freight from any of the wholly owned subsidiary locations in the U.S.A. or any place in the world and ship such commercial products or the like to any member addresses that are located in U.S.A. or at any place in the world.

The development of MedTrackSystem provides the look-ups, printing or viewing of pictures or descriptions, or enlarging the pictures or descriptions or providing audio and video that describes the pictures or descriptions of trade, brand or generic names of prescription medications thus minimizes the error of prescribing duplicated medications to members and provides members better medication information that helps them understand as to the effectiveness in managing their medication protocols with ease and accuracy. The capability of the MedTrackSystem in providing members the instructions as to when is the best time to take each prescribed medication to take advantage of the full potency of the said medication if taken properly, the auto sending of email to all active physicians if a new medication has been prescribed so a heart specialists would know if the family physician has prescribed a new medication that may harm the member heart's condition, the auto sending of email to all active physicians announcing that a new laboratory tests have been ordered to prevent the unnecessary over drawing of members blood especially if the member has been diagnosed with a kidney failure where blood levels should be maintained at a certain level, the auto sending of email when a future physician appointment is scheduled not only being sent to the member but also to those who are authorized by the member to receive such new appointment email.

In addition, the MedTrackSystem provides a comparative descending order of laboratory results reporting where one of the most recent tests could easily be compared with all the other previous test results of same test which will aid the physician in determining the next effective series of treatments for the member. Additionally, MedTrackSystem provides listing of possible drug interactions or food interactions when a new medication is prescribed that could warn the prescribing physician or the member or the member authorized representative about the possible dangerous side effects of new medication in relation with those medications that are still active that the members are currently taking, the introduction of medication audit to protect members against fraud, erroneous billing, duplicate billings by utilizing the past and present diagnoses and/or procedures of said members. The ability of MedTrackSystem to provide a secondary medication billed charges checking by classifying member visits either inpatient or outpatient, and full utilization of using CPT codes, diagnosis code and procedure codes to link reasonably all medication billing charges with services provided to members before payment is authorized, the development of MedTrackSystem where logarithmic logical sequencing are used to establish different reasonable protocols that may apply to CPT codes, diagnosis codes and procedure codes, and providing members low cost of prescription medications, pharmaceutical supplies, over the counter medications, medical equipment or other supplies or the like at wholesale price plus freight from any partner or the wholly owned subsidiary locations in the U.S.A. or any place in the world and ship them to any member addresses that are located in U.S.A. or at any place in the world. The recent 60 minutes news broadcast showed an estimated 60 billion dollars fraudulent claims have been paid by medicare program could have possibly been prevented if the invention's medication audit system has been implemented.

In other situation, the MedTrackSystem provides interactive communications medium between the provider and the member, not only through the internet, email, telephone, postal mail or the like, but also and most importantly a person to person communication between the provider and the member notably in relation to various prevention and intervention programs, provides an alert system in connection with the prevention of a disease or diseases of coming back or preventing a disease or diseases on starting anew that are communicated by the provider to the members. For example, if a member had just been diagnosed as having a pre-diabetic medical condition, the provider can then recommend to the member to follow certain evidence based practices that relate to intervention programs that prevent the conversion of a pre-diabetic medical condition into either a diabetic type 1 or diabetic type 2 condition. As one of the prevention program may also include, but not limited to suggestion that member could start eating less red meat, eat more fruits, vegetables, whole wheat bread (instead of regular enriched bread), avoid drinking carbonated sodas and/or any alcoholic beverages (drinking green tea instead), adopt exercise regimens daily or weekly and with the provider proactively advocating that the member be re-tested periodically, for the very purpose of preventing the pre-diabetic condition developing into either a diabetes type 1 or type 2 real disease condition. As another example, would be the early detection of an esophageal cancer. The symptoms would include heartburn, coughing, tiredness, losing weight, difficulty swallowing and some others. If a member had consulted a physician numerous times regarding a heartburn condition that would not go away, even after taking different kinds of medications, then next preferred step would be for the member to request the primary physician to order an esophagogastroduodenoscopy which is a diagnostic endoscopic procedure that visualizes the upper part of the gastrointestinal tract up to the duodenum and if the results is showing something suspicious, then a CT scan is ordered to assure that an esophageal cancer is not present, and if there is one then hopefully will able to catch the disease at its earliest stage so appropriate treatments could be done right away before it becomes too late for all the treatments. Because the MedTrackSystem is programmed to continually analyze members physicians visits, on the third repeat reason for visit of heartburn, then the MedTrackSystem sends an alert to the provider and the member for the probable ordering of esophagogastroduodenoscopy procedure then followed by a CT scan examination if needed to rule out the possibility of an esophageal cancer. This is one of several preventive system programs that provider provides to members not only for the purpose of preventing a disease in getting into its worse condition but at the same time reduces our health care cost.

In the foregoing specification, the invention has been described as applicable to an implementation anticipating not only an Internet based processing system which may include the entering and retrievals by the subscribing members listing of their respective medications from home, the listing of medications that should not be prescribed to said members, their allergies or the like, sharing by said members their respective medical records to any authorized users so designated by said members, and the provider providing members the complete control of the viewing, retrieving or printing of users who have viewed, printed, downloaded their medical records along with the audit trail of who enter, modify, delete any member medication information components, the provider providing wallet size type printout of member allergies, active medication listings, or the like, and in time builds a complete electronic medical record history for each member, but also provides a person to person communication interaction between the provider and the member, especially in cases where the provider follow up with the members who have received any abnormal test results and continue follow-up with said members until such abnormal test results have been converted back to normal or any other acceptable ranges of results. Additionally, this invention provides the member special advantages of not only having a safety measures against adverse drug events that sometimes results in death, the member being provided prevention programs, wellness programs that are based on evidence based practices, the member being provided by an alerts system that may involved like providing a new discovered warning of medications side effects or new procedures that the member needs to be aware off, but also in effect reduces said member lifetime medication cost.

In the foregoing specification, the invention has been described with reference to specific embodiments thereof. However, various modifications and changes may be made thereto without departing from the broader spirit and scope of the invention. The specification and drawings are, accordingly, to be regarded in an illustrative sense rather than a restrictive sense, and the scope of the invention is limited only by the claims that follow.

I claim:

1. A health management system, comprising:
a computerized management site having a program stored on a non-transitory computer-readable medium statically embodied in and executable through one or more servers that stored multi-databases executing from a non-transitory computer-readable medium;
a data repository I for storing medical data regarding a member accessible only by primary password;
a data repository II for storing other personal data regarding a member accessible only by secondary password;
communication paths provided by the system at least between individual ones of registered partner entities and the data repository, wherein registered partner entities include physicians and medical facilities; and
an interactive interface to the system and accessible by the member through secure log-ins, including mechanisms enabling the member or its authorized representative to directly enter medical data or other personal data regarding the member and authorizations for use by individual ones of the partner entities of the data entered;
wherein, the member, through the interactive interface, is enabled to populate the data repository I with a list of medications and medication schedules for the member, and allergies to which the member may be subject, and, through authorizations, controls access to the medical data and/or to populate data repository II with other personal data by individual ones, the health management system further comprising:
(a) a health management screen display, allowing said enrolled members, members assigned authorized representative, associated physicians, and other partner entities data capture including:
  i. enrolled members identifying data;
  ii. allergies associated with said enrolled members;
  iii. medications associated with said enrolled members;
  iv. medications not to be prescribed with said enrolled members;
  v. other personal information entered and viewable only by said enrolled members; and
(b) an alert system is provided that sends notifications to all member's active physicians and member's authorized representatives if new medications are prescribed, new appointments are scheduled and new laboratory tests are ordered; and
(c) a person to member follow-up reminder communication system between said system and said enrolled members having received any abnormal test results is implemented and continues said follow-ups until said abnormal test results are converted back to any acceptable or allowable results; and
(d) a printer provided to the member configured to view or print the list of users who have viewed, printed, downloaded any part of said member's medical records data at any time at member's choosing via a provided icon; and
(e) a fraud billing prevention system whereby:
  i. members prior and current diagnoses are compared with that of the submitted third party billings;
  ii. members prior and current procedures are compared with that of the submitted third party billings;
  iii. members outpatient visits billed charges are checked for correct CPT codes assignments;
  iv. submitting physicians status are checked to make sure they are still living and are legally licensed and able to practice medicine in the country;
  v. create members paid database records comprising of paid medications, services rendered, equipment purchases which are then used to compare against a newer third party submitted billings;
  vi. checks for the reasonableness of medication billing intervals for same medication, same service, same equipment submitted by third party billers.

2. The system of claim 1 wherein the computerized management system is Internet-connected, and members and associate and partner entities interact with the service through encrypted Internet connection.

3. The system of claim 1 wherein physicians associated with enrolled members are enabled to edit and alter medications and medication schedules for individual enrolled members with whom they are associated in the system, and alterations will be published by the system, subject to authorization by the enrolled member, with other physicians and associate and partner entities each also associated with the enrolled member.

4. The system of claim 3 wherein the member is enabled to enter allergies in general and allergies to medications, as well as medication data.

5. The system of claim 4 wherein, in any transaction changing medication data for an enrolled member, allergy data is consulted, and participants are alerted to any potential problem.

6. The system of claim 3 wherein the data repository stores information regarding potential interactions between medications and between medications and common foods and beverages, and, in any transaction changing medication data for an enrolled member, the potential interaction data is consulted, and participants are alerted to any potential problem.

7. The system of claim 6 wherein new members enrolling in the service, after entering their medication data, are informed of potential interactions between medications and potential effects of such interactions.

8. The system of claim 1 wherein enrolled members are enabled to enter and view other personal information by utilizing a secondary password.

9. The system of claim 1 further comprising a mechanism, including interactive interface, for a enrolled members to purchase medications, products and services from enrolled partner firms.

10. The system of claim 9 wherein enrolled members are afforded discounts for purchases from enrolled partner firms.

11. The system of claim 1 wherein the service provides email service to enrolled members and partners and associates.

12. The system of claim 9 wherein enrollment provides membership requiring a periodic membership fee, and discounts on the membership fee are afforded to enrolled members as reward for exceeding pre-set thresholds in purchasing medications, products and services from enrolled partner firms.

13. The system of claim 1 wherein the system seeks sources for medications, products and services from other than enrolled partners and associates.

14. The system of claim 13 wherein the system seeks sources for generic versions of medications.

15. The system of claim 1 wherein information regarding best times and circumstances for taking medications is stored, and provided to enrolled members according to the enrolled member's medication data.

16. The system of claim 9 wherein the system provides accounting and billing services for enrolled members in the purchase of medications, products and services.

17. The system of claim 3 wherein a library of preventive medical and wellness programs are provided in assisting in the prevention of the recurrence of said enrolled members-medical conditions.

18. The system of claim 1 wherein the system provides the displaying, enlarging, audio or video of medication information components.

19. The system of claim 1 wherein the system authenticates physician status and requires the use of multiple passwords for prescribing new medications electronically.

20. The system of claim 1 wherein the system provides electronic monitoring system wireless or not, and wallet size print out of allergies and medication listing;
   whereby health care cost can be reduced systematically through the implementation of various preventive health care and wellness programs, discounted medication purchases provided, and effective prevention of fraud in medical billing reimbursement network.

* * * * *